(12) United States Patent
Malanson et al.

(10) Patent No.: US 12,312,394 B2
(45) Date of Patent: May 27, 2025

(54) METHODS OF PRODUCING ANTI-C5 ANTIBODIES

(71) Applicant: Alexion Pharmaceuticals, Inc., Boston, MA (US)

(72) Inventors: Hunter F. Malanson, Wallingford, CT (US); Kyle A. Zingaro, Southington, CT (US); Anjil Giri, Hamden, CT (US); Justin Weaver, Manchester, CT (US); Abraham Friedman, West Hartford, CT (US); Jeffrey William Hunter, Wallingford, CT (US); Saranya Sivanandam, Norwalk, CT (US); Jeffrey Zugates, Hamden, CT (US); Rahul Godawat, Woodbridge, CT (US)

(73) Assignee: Alexion Pharmaceuticals, Inc., Boston, MA (US)

(*) Notice: Subject to any disclaimer, the term of this patent is extended or adjusted under 35 U.S.C. 154(b) by 1087 days.

(21) Appl. No.: 17/254,508

(22) PCT Filed: Jun. 27, 2019

(86) PCT No.: PCT/US2019/039557
§ 371 (c)(1),
(2) Date: Dec. 21, 2020

(87) PCT Pub. No.: WO2020/006266
PCT Pub. Date: Jan. 2, 2020

(65) Prior Publication Data
US 2021/0122806 A1    Apr. 29, 2021

Related U.S. Application Data

(60) Provisional application No. 62/811,710, filed on Feb. 28, 2019, provisional application No. 62/691,428, filed on Jun. 28, 2018.

(51) Int. Cl.
*A61K 39/395*    (2006.01)
*B01D 15/36*    (2006.01)
*B01D 15/38*    (2006.01)
*C07K 16/06*    (2006.01)
*C07K 16/18*    (2006.01)

(52) U.S. Cl.
CPC .......... *C07K 16/065* (2013.01); *B01D 15/362* (2013.01); *B01D 15/363* (2013.01); *B01D 15/3809* (2013.01); *C07K 16/18* (2013.01); *C07K 2317/565* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 4,485,045 A | 11/1984 | Regen |
| 4,544,545 A | 10/1985 | Ryan et al. |
| 4,816,567 A | 3/1989 | Cabilly et al. |
| 4,863,457 A | 9/1989 | Lee |
| 4,868,116 A | 9/1989 | Morgan et al. |
| 4,980,286 A | 12/1990 | Morgan et al. |
| 5,013,556 A | 5/1991 | Woodle et al. |
| 5,308,341 A | 5/1994 | Chanoch |
| 5,443,505 A | 8/1995 | Wong et al. |
| 5,447,145 A | 9/1995 | Cappello et al. |
| 5,501,856 A | 3/1996 | Ohtori et al. |
| 5,624,821 A | 4/1997 | Winter et al. |
| 5,648,260 A | 7/1997 | Winter et al. |
| 5,773,019 A | 6/1998 | Ashton et al. |
| 5,997,848 A | 12/1999 | Patton et al. |
| 6,001,329 A | 12/1999 | Buchsbaum et al. |
| 6,001,386 A | 12/1999 | Ashton et al. |
| 6,005,079 A | 12/1999 | Casterman et al. |
| 6,019,968 A | 2/2000 | Platz et al. |
| 6,095,141 A | 8/2000 | Armer et al. |
| 6,146,361 A | 11/2000 | DiBiasi et al. |
| 6,170,717 B1 | 1/2001 | Di Giovanni et al. |
| 6,192,891 B1 | 2/2001 | Gravel et al. |

(Continued)

FOREIGN PATENT DOCUMENTS

| | | |
|---|---|---|
| AU | 2018201961 A1 | 4/2018 |
| EP | 430539 A2 | 6/1991 |

(Continued)

OTHER PUBLICATIONS

U.S. Appl. No. 18/219,138, filed Jul. 7, 2023, Bruce A. Andrien Jr.

(Continued)

*Primary Examiner* — Yunsoo Kim
(74) *Attorney, Agent, or Firm* — Nelson Mullins Riley & Scarborough LLP; Jane E. Remillard, Esq.; Jill Gorny Sloper, Esq.

(57) ABSTRACT

The present application relates to a method of producing an anti-C5 antibody (ravulizumab), wherein the method comprises: —culturing mammalian cells comprising a nucleic acid encoding the anti-C5 antibody in a cell culture production medium—Performing two or more steps selected from the group consisting of: a recovery step; purification by Protein A affinity chromatography, a low pH viral inactivation step; Purification by cation exchange chromatography; Purification by anion exchange chromatography; a virus reduction filtration step; and a concentration and diafiltration step.

27 Claims, 12 Drawing Sheets
Specification includes a Sequence Listing.

(56) References Cited

U.S. PATENT DOCUMENTS

| | | |
|---|---|---|
| 6,194,551 B1 | 2/2001 | Idusogie et al. |
| 6,200,296 B1 | 3/2001 | Dibiasi et al. |
| 6,277,099 B1 | 8/2001 | Strowe et al. |
| 6,277,375 B1 | 8/2001 | Ward |
| 6,300,064 B1 | 10/2001 | Knappik et al. |
| 6,302,855 B1 | 10/2001 | Lav et al. |
| 6,355,245 B1 | 3/2002 | Evans et al. |
| 6,737,056 B1 | 5/2004 | Presta |
| 6,933,368 B2 | 8/2005 | Co et al. |
| 7,112,341 B1 | 9/2006 | Nagarajan et al. |
| 7,371,826 B2 | 5/2008 | Presta |
| 7,390,786 B2 | 6/2008 | Warne et al. |
| 7,556,615 B2 | 7/2009 | Pettis et al. |
| 7,670,600 B2 | 3/2010 | Dall'Acqua et al. |
| 7,704,497 B2 | 4/2010 | Dall'Acqua et al. |
| 8,088,376 B2 | 1/2012 | Chamberlain et al. |
| 8,323,962 B2 | 12/2012 | Dall'Acqua et al. |
| 8,367,805 B2 | 2/2013 | Chamberlain et al. |
| 8,802,820 B2 | 8/2014 | Chamberlain et al. |
| 9,079,949 B1 | 7/2015 | Andrien, Jr. et al. |
| 9,107,861 B1 | 8/2015 | Andrien, Jr. et al. |
| 9,206,251 B2 | 12/2015 | Andrien, Jr. et al. |
| 9,371,377 B2 | 6/2016 | Andrien, Jr. et al. |
| 9,447,176 B2 | 9/2016 | Rother et al. |
| 9,556,263 B2 | 1/2017 | Zhou et al. |
| 9,663,574 B2 | 5/2017 | Andrien, Jr. et al. |
| 9,771,418 B2 | 9/2017 | Rother et al. |
| 9,803,007 B1 | 10/2017 | Andrien, Jr. et al. |
| 10,227,400 B2 | 3/2019 | Andrien, Jr. et al. |
| 10,584,164 B2 | 3/2020 | Andrien, Jr. et al. |
| 11,365,241 B2 | 6/2022 | Ortiz et al. |
| 11,434,280 B2 | 9/2022 | Andrien, Jr. et al. |
| 12,012,448 B2 | 6/2024 | Ortiz et al. |
| 2002/0026176 A1 | 2/2002 | Varner et al. |
| 2005/0271660 A1 | 12/2005 | Wang |
| 2006/0141456 A1 | 6/2006 | Edwards et al. |
| 2007/0172483 A1 | 7/2007 | Schwaeble et al. |
| 2007/0235029 A1 | 10/2007 | Zhu et al. |
| 2008/0202513 A1 | 8/2008 | Birchall et al. |
| 2008/0241223 A1 | 10/2008 | Nivaggioli et al. |
| 2009/0110679 A1 | 4/2009 | Li et al. |
| 2010/0098730 A1 | 4/2010 | Lowman et al. |
| 2011/0111406 A1 | 5/2011 | Igawa et al. |
| 2012/0225056 A1 | 9/2012 | Rother et al. |
| 2012/0230982 A1 | 9/2012 | Zhou et al. |
| 2013/0344088 A1 | 12/2013 | Cosenza et al. |
| 2014/0056888 A1 | 2/2014 | Zhou et al. |
| 2015/0299305 A1 | 10/2015 | Andrien, Jr. et al. |
| 2016/0108115 A1 | 4/2016 | Andrien, Jr. et al. |
| 2016/0251433 A1 | 9/2016 | Andrien, Jr. et al. |
| 2016/0272700 A1 | 9/2016 | Zhou et al. |
| 2016/0355579 A1 | 12/2016 | Rother et al. |
| 2016/0355580 A1 | 12/2016 | Rother et al. |
| 2017/0298123 A1 | 10/2017 | Andrien, Jr. et al. |
| 2017/0355757 A1 | 12/2017 | Hu et al. |
| 2017/0369562 A1 | 12/2017 | Rother et al. |
| 2018/0009885 A1 | 1/2018 | Andrien, Jr. et al. |
| 2018/0311299 A1 | 11/2018 | Griffin et al. |
| 2018/0311345 A1 | 11/2018 | Pober et al. |
| 2019/0263897 A1 | 8/2019 | Andrien, Jr. et al. |
| 2019/0276524 A1 | 9/2019 | Griffin et al. |
| 2020/0140531 A1 | 5/2020 | Rother et al. |
| 2020/0157200 A1 | 5/2020 | Andrien, Jr. et al. |
| 2020/0254092 A1 | 8/2020 | Payton et al. |
| 2020/0369751 A1 | 11/2020 | Ortiz et al. |
| 2021/0187054 A1 | 6/2021 | Griffin et al. |
| 2021/0214425 A1 | 7/2021 | Payton et al. |
| 2021/0332147 A1 | 10/2021 | Payton et al. |
| 2023/0002482 A1 | 1/2023 | Philominathan et al. |
| 2023/0106734 A1 | 4/2023 | Ortiz et al. |
| 2023/0257456 A1 | 8/2023 | Ortiz et al. |
| 2024/0141024 A1 | 5/2024 | Andrien, Jr. et al. |

FOREIGN PATENT DOCUMENTS

| | | |
|---|---|---|
| EP | 0488401 A1 | 6/1992 |
| EP | 2006381 A1 | 12/2008 |
| EP | 1610820 B1 | 9/2010 |
| EP | 2275443 A1 | 1/2011 |
| EP | 3095795 A1 | 11/2016 |
| JP | 2002-500164 A | 1/2002 |
| JP | 2010-215674 A | 9/2010 |
| JP | 2010-529999 A | 9/2010 |
| JP | 2015-536930 A | 12/2015 |
| JP | 2017-095440 A | 6/2017 |
| JP | 2018-503620 A | 2/2018 |
| WO | 8902468 A1 | 3/1989 |
| WO | 8905345 A1 | 6/1989 |
| WO | 8907136 A2 | 8/1989 |
| WO | 9207573 A1 | 5/1992 |
| WO | 94/02559 A1 | 2/1994 |
| WO | 94/04678 A1 | 3/1994 |
| WO | 94/28027 A1 | 12/1994 |
| WO | 9734631 A1 | 9/1997 |
| WO | 98/23289 A1 | 6/1998 |
| WO | 98/47531 A2 | 10/1998 |
| WO | 9919343 A1 | 4/1999 |
| WO | 0061178 A1 | 10/2000 |
| WO | 0069887 A2 | 11/2000 |
| WO | 0178693 A2 | 10/2001 |
| WO | 2002/013859 A1 | 2/2002 |
| WO | 2003/074679 A2 | 9/2003 |
| WO | 03105757 A2 | 12/2003 |
| WO | 2004024156 A1 | 3/2004 |
| WO | 2004026380 A2 | 4/2004 |
| WO | 2004029207 A2 | 4/2004 |
| WO | 2004060407 A1 | 7/2004 |
| WO | 2004073551 A2 | 9/2004 |
| WO | 2004091658 A1 | 10/2004 |
| WO | 2005011735 A1 | 2/2005 |
| WO | 2005040217 A2 | 5/2005 |
| WO | 2005/077981 A2 | 8/2005 |
| WO | 2005092925 A2 | 10/2005 |
| WO | 06/031994 A2 | 3/2006 |
| WO | 2006/053301 A2 | 5/2006 |
| WO | 2006094234 A1 | 9/2006 |
| WO | 2006/105338 A2 | 10/2006 |
| WO | 2006/122257 A2 | 11/2006 |
| WO | 2007041635 A2 | 4/2007 |
| WO | 2007/103134 A2 | 9/2007 |
| WO | 2007/106585 A1 | 9/2007 |
| WO | 2007114319 A1 | 10/2007 |
| WO | 08/043822 A2 | 4/2008 |
| WO | 2008048545 A2 | 4/2008 |
| WO | 2008092117 A2 | 7/2008 |
| WO | 2008/157356 A2 | 12/2008 |
| WO | 2009/041643 A1 | 4/2009 |
| WO | 2009058492 A2 | 5/2009 |
| WO | 2009086320 A1 | 7/2009 |
| WO | 2009125825 A1 | 10/2009 |
| WO | 2010/127069 A1 | 11/2010 |
| WO | 2010/151526 A1 | 12/2010 |
| WO | 2011/104381 A2 | 9/2011 |
| WO | 2011111007 A2 | 9/2011 |
| WO | 2011/122011 A2 | 10/2011 |
| WO | 2011/137362 A1 | 11/2011 |
| WO | 2012/073992 A1 | 6/2012 |
| WO | 2012133782 A1 | 10/2012 |
| WO | 2013046704 A2 | 4/2013 |
| WO | 2013047748 A1 | 4/2013 |
| WO | 2014/068021 A1 | 5/2014 |
| WO | 2015/134894 A1 | 9/2015 |
| WO | 2016/098356 A1 | 6/2016 |
| WO | 2016/106291 A1 | 6/2016 |
| WO | 2016/160756 A2 | 10/2016 |
| WO | 2016/209956 A1 | 12/2016 |
| WO | 2017/044811 A1 | 3/2017 |
| WO | 2017/051273 A1 | 3/2017 |
| WO | 2017/123636 A1 | 7/2017 |
| WO | 2017/218515 A1 | 12/2017 |
| WO | 2018/109588 A2 | 6/2018 |
| WO | 2019/023564 A1 | 1/2019 |

(56) References Cited

FOREIGN PATENT DOCUMENTS

| | | |
|---|---|---|
| WO | 2019/084438 A1 | 5/2019 |
| WO | 2019/231983 A1 | 12/2019 |
| WO | 2019/236345 A1 | 12/2019 |
| WO | 2020/006266 A1 | 1/2020 |
| WO | 2020/092549 A1 | 5/2020 |
| WO | 2020/154626 A1 | 7/2020 |
| WO | 2021/091937 A1 | 5/2021 |

OTHER PUBLICATIONS

Junghans, R. et al., "The protection receptor for IgG catabolismis the beta2-microglobulin-containing neonatal intestinal transport receptor," PNAS, USA, vol. 93(11):5512-5516 (1996).
Jungi and Pepys, Immunology 43(2): 271-279 (1981).
Kaszubska et al., Protein Expression and Purification 18: 213-220 (2000).
Kay et al., Human Gene Therapy 3: 641-647 (1992).
Kim et al., Ophthalmic Res 39: 244-254 (2007).
Kinstler et al., Advanced Drug Deliveries Reviews 54: 477-485.
Klein et al., Proc. Natl Acad Sci USA 78: 524-528 (1981).
Kroshus et al., Transplantation 60: 1194-1202 (1995).
Lee, CV., et al., "High-affinity human antibodies from phage-displayed synthetic Fab libraries with a single framework scaffold," J. Molecular Biology, vol. 340 (5):1073-1093 (2004).
Lee, et al., Bioconjug Chem 10(6): 973-81 (1999).
Lee, J-W et al., "Results from a Phase 3, Multicenter, Noninferiority Study of Ravulizumab (ALXN1210) Versus Eculizumab in Adult Patients with Paroxysmal Nocturnal Hemoglobi-nuria (PNH) Naïve to Complement Inhibitors," (2018), XP055550310, Retrieved from the Internet: URL:https://learningcenter.ehaweb.org/eha/2018/stockholm/218885/jong.wook.lee.results.from.a.phase.3.multicenter.noninferiority.study.of.html?f=media=1 [retrieved on Jan. 31, 2019].
Lee, J-W et al., "Ravulizumab (ALXN1210) vs eculizumab in adult patients with PNH naive to complement inhibitors: the 301 study," Blood, (2018) ISSN: 0006-4971, DOI: 10.1182/blood-2018-09-876136.
Lee, J-W. et al., "2428 Immediate, Complete, and Sustained Inhibition of C5 with ALXN1210 Reduces Complement-Mediated Hemolysis in Patients with Paroxysmal Noctur-nal Hemoglobinuria (PNH): Interim Analysis of a Dose-Escalation Study," Internet Ci-Tation, Dec. 4, 2016 (Dec. 4, 2016), XP002768543, Retrieved from the Internet: URL:https://ash.confex.com/ash/2016/webprogram/Paper90053.html [retrieved on Mar. 23, 2017].
Legendre, CM, et al., "Terminal Complement Inhibitor Eculizumab in Atypical Hemolytic-Uremic Syndrome," N Engl J Med., vol. 368:2169-2181 (2013).
Levy and Ladda, Nat New Biol 229(2): 51-52 (1971).
Licht, C., et al., "The global aHUS registry: methodology and initial patient characteristics," BMC Nephrology, vol. 16 (207) 8 pages (2015) DOI 10.1186/s12882-015-0195-1.
Lodmell et al., Vaccine 18:1059-1066 (2000).
Loirat, C. et al., "Plasmatherapy in Atypical Hemolytic Uremic Syndrome," Seminars in Thrombosis and Hemostasis, vol. 36(6): 673-681 (2010).
Loirat, C. et al., "An international consensus approach to the management of atypical hemolytic uremic syndrome in children," Pediatr Nephrol., vol. 31:15-39 (2016).
Loirat, C. et al., "Atypical hemolytic uremic syndrome," Orphanet Journal of Rare Diseases, vol. 6:60: 30 pages (2011).
Lusky and Botchan, Nature 293: 79 (1981).
Malina, M. et al., "Peripheral Gangrene in Children With Atypical Hemolytic Uremic Syndrome," Pediatrics, vol. 131: e331-e335 (2013).
McLaughlin et al., J Virol 62: 1963-1973 (1988).
Medicus et al., J Exp Med 144: 1076-1093 (1976).
Mihu et al., J Gastrointestin Liver Dis 16(4): 4034-4034 (2007).
Moongkarndi et al. Immunobiol 165: 323 (1983).
Moongkarndi et al., Immunobiol 162: 397 (1982).
Morell et al., J Clin Invest 49(4): 673-680 (1970).
Mueller et al., Mol Immunol 34(6): 441-452 (1997).
Muller-Eberhard, Ann Rev Biochem 57: 321-347 (1988).
Mullett et al., Methods 22: 77-91 (2000).
Mulligan and Berg Proc Natl Acad Sci USA 78: 2072 (1981).
Mullinax et al., BioTechniques 12(6): 864-869 (1992).
Muyldermans et al., Molecular Biotechnology 26: 230-235 (2001).
Newkirk et al., Clin Exp Immunol 106(2): 259-264 (1996).
Noris, M. et al., "STEC-HUS, atypical HUS and TTP are all diseases of complement activation," Nat. Rev. Nephrol., vol. 8: 622-633 (2012).
Nuttall et al., Curr Pharm Biotech 1: 253-263 (2000).
Park et al., Anesth Analg 99(1): 42-48 (1999).
Pavisic et al., Int J Pharm 387(1-2)L 110-119 (2010).
Petkova et al., Int Immunol 18(12): 1759-69 (2006).
Poljak, Structure 2(12): 1121-1123 (1994).
Pollock et al., J Immunol Methods 231(1-2): 147-157 (1999).
Qiao et al., Proc Natl Acad Sci USA 105(27): 9337-9342 (2008).
Rabinovici et al., J Immunol 149 1744-1750 (1992).
Raju, BioProcess International 1(4): 44-53 (2003).
Ranta and Uritti, Adv Drug Delivery Rev 58(11): 1164-1181 (2006).
Rawal and Pangburn, J Immunol 166(4): 2635-2642 (2001).
Reiss, U. et al., "Efficacy and safety of eculizumab in children and adolescents with paroxysmal nocturnal hemoglobinuria," Pediatric Blood and Cancer, vol. 61(9):1544-1550 (2014).
Rich et al., Curr Opin Biotechnol 11: 54-61 (2000).
Riechmann et al., J Immunol Meth 231: 25-38 (1999).
Wang W., "Instability, stabilization and formulation of liquid protein pharmaceuticals," International Journal of Pharmaceutics, vol. 185(2): 129-188 (1999) doi:10.1016/s0378-5173(99)00152-0.
Wang, W. et al., "Antibody Structure, Instability, and Formulation," Journal of Pharmaceu-tical Sciences, American Chemical Society and American Pharmaceutical Association, vol. 96(1):1-26 (2007).
Ward and Zvaifler, J Clin Invest 50(3): 606-16 (1971).
Waters, A. et al., "aHUS caused by complement dysregulation: new therapies on the horizon," Pediatr Nephrol., vol. 26:41-57 (2011).
Weisman et al., Science 249: 146-151 (1990).
Wetsel et al., J Biol Chem 265: 2435-2440 (1990).
Wigler et al., Cell 16: 777-785 (1979).
Wilson et al., Proc Natl Acad Sci USA 85: 3104-3018 (1988).
Wong, E. et al., "Anticomplement C5 therapy with eculizumab for the treatment of parox-ysmal nocturnal hemoglobinuria and atypical hemolytic uremic syndrome," Translational Research, vol. 165 (2): 306-320 (2015) XP055358380, NL ISSN: 1931-5244, DOI:10.1016/j.trsl.2014.10.010.
Wright et al., EMBO J 10(10): 2717-2723 (1991).
Wurzner et al., Complement Inflamm 8: 328-340 (1991).
Xu et al, Cell Immunol 200: 16-26 (2000).
Yuksel, S. et al., "First-Line, Early and Long-Term Eculizumab Therapy in Atypical Hemolytic Uremic Syndrome: A Case Series in Pediatric Patients," Pediatr Drugs, vol. 18:413-420 (2016) DOI 10.1007/s40272-016-0194-0.
Zalevsky et al., Nat Biotech 28: 157-159 (2010).
Zuber, J. et al., "new insights into postrenal transplant hemolytic uremic syndrome," Nat. Rev. Nephrol., vol. 7: 23-35 (2011).
U.S. Appl. No. 17/865,681, filed Jul. 15, 2022, Bruce A. Andrien.
U.S. Appl. No. 16/750,173, filed Jan. 23, 2020, Bruce A. Andrien, U.S. Pat. No. 11,434,280.
U.S. Appl. No. 16/246,842, filed Jan. 14, 2019, Bruce A. Andrien, U.S. Pat. No. 10,584,164.
U.S. Appl. No. 15/708,658, filed Sep. 19, 2017, Bruce A. Andrien, U.S. Pat. No. 10,227,400.
U.S. Appl. No. 15/492,622, filed Apr. 20, 2017, Bruce A. Andrien, U.S. Pat. No. 9,803,007.
U.S. Appl. No. 15/160,364, filed May 20, 2016, Bruce A. Andrien, U.S. Pat. No. 9,663,574.
U.S. Appl. No. 14/923,879, filed Oct. 27, 2015, Bruce A. Andrien, U.S. Pat. No. 9,371,377.
U.S. Appl. No. 14/641,026, filed Mar. 6, 2015, Bruce A. Andrien, U.S. Pat. No. 9,079,949.
U.S. Appl. No. 14/727,313, filed Jun. 1, 2015, Bruce A. Andrien, U.S. Pat. No. 9,107,861.
U.S. Appl. No. 14/789,329, filed Jul. 1, 2015, Bruce A. Andrien, U.S. Pat. No. 9,206,251.

(56) References Cited

OTHER PUBLICATIONS

U.S. Appl. No. 17/738,131, filed May 6, 2022, Stephan Ortiz.
U.S. Appl. No. 16/633,930, filed Jan. 24, 2020, Stephan Ortiz, U.S. Pat. No. 11,365,241.
U.S. Appl. No. 17/773,941, filed May 3, 2022, Leena Philominathan.
International Preliminary Report on Patentability, PCT/US2019/039557, dated Dec. 29, 2020, 8 pages.
International Search Report and Written Opinion, PCT/US2019/039557, dated Nov. 11, 2019, 12 pages.
Liu, et al., "Recovery and purification process development for monoclonal antibody production," MABS, vol. 2(5) 480-499 (2010).
Ambati and Adamis, Prog Retin Eye Res 21(2): 145-151 (2002).
Amsterdam et al., Am J Physiol 268: H448-H457 (1995).
Anonymous, "Highlights of Prescribing Information —Ultomiris (ravulizumab-cwvz) injection, for intravenous use Initial U.S. Approval: 2018", (Oct. 1, 2019), URL: Ultomiris (ravulizumab-cwvz) injection, for intravenous use Initial U.S. Approval: 2018.
Anonymous, "Recipe: Sodium phosphate", doi:10.1101/PDB. REC8303, ISSN 1559-6095, pp. 1-3, Cold Spring Harbor Protocols, URL: http://cshprotocols.cshlp.org/content/2006/1/pdb.rec8303.full?text_only=true, (Mar. 20, 2015), XP002737558.
Anonymous: "Alexion Receives FDA Approval for Ultomiris (ravulizumab-cwvz) for Atypical Hemolytic Uremic Syndrome (aHUS)," Oct. 18, 2019.
Anonymous: "Assessment report Soliris /Eculizumab," pp. 1-28,Mar. 21, 2013, Retrieved from the Internet:URL: https://www.ema.europa.eu/en/documents/variation-report/soliris-h-c-791-ii-0050-epar-assessment-report-variation_en.pdf [retrieved on Aug. 7, 2019].
Anonymous: "Ravulizumab for atypical haemolytic uraemic syndrome in adults and children—first line," Aug. 1, 2018, pp. 1-10.
Anonymous: "Single Arm Study of ALXN1210 in Complement Inhibitor Treatment—Naive Adult and Adolescent Patients With Atypical Hemolytic Uremic Syndrome (aHUS)," pp. 1-6 (2016) XP055619305,Retrieved from the Internet:URL: https://clinicaltrials.gov/ct2/show/NCTO2949128?term=alxn1210&rank=8 [retrieved on Sep. 6, 2019].
Anonymous: "Study of Ravulizumab in Children and Adolescents With Atypical Hemolytic Uremic Syndrome (aHUS)", Apr. 27, 2017 (Apr. 27, 2017), pp. 1-6, XP055619309,Retrieved from the Internet: URL:https://clinicaltrials.gov/ct2/show/NCTO3131219?term=alxn1210&rank=5 [retrieved on Sep. 6, 2019].
Appel et al., J Am Soc Nephrol 16: 1392-1404 (2005).
Armentano et al., Proc Natl Acad Sci USA 87: 6141-6145 (1990).
Baldridge et al., Methods 19: 103-107 (1999).
Barocas and Balachandran, Expert Opin Drug Delivery 5(1): 1-10 (10) (2008).
Baudino et al.I, J Immunol 181: 6664-6669 (2008).
Berge et al., J Phar4m Sci 66: 1-19 (1977).
Berkner et al., BioTechniques 6: 616 ( 1988).
Better et al., Science 240: 1041-1043 (1988).
Bieg et al., Autoimmunity 31(1): 15-24 (1999).
Bless et al., Am J Physiol 276(1): L57-L63 (1999).
Brodsky, R. et al., "Complement in hemolytic anemia," Blood, vol. 126(22):2459-2465 (2015).
Burmeister et al., Nature 372: 379-383 (1994).
Burton et al., Adv Immun 51:1-18 (1992).
Burton et al., Adv Immun 51:52 pages (1992).
Campistol, J., et al., "An update for atypical haemolytic uraemic syndrome: diagnosis and treatment. A consensus document," Nefrologia, vol. 33(1):27-45 (2013).
Canfield et al., J Exp Med 173: 1483-1491 (1991).
Caron et al., J Exp Med 176: 1191-1195 (1992).
Chaparro-Riggers, Biol Chem 287: 11090-11097 (2012).
Chothia et al., Nature 342: 877-883 (1989).
Chowdhury et al., Science 254: 1802-1805 (1991).
Christmann, M., et al., "Eculizumab as First-Line Therapy for Atypical Hemolytic Uremic Syndrome," Pediatrics, vol. 133, e1759: 7 pages (2014).
Co et al., Mol Immunol 30: 1361 (1993).
Co et al., Mol Immunol 30: 1361, 6 pages (1993).
Cooper et al., J Exp Med 132: 775-793 (1970).
Crocker et al., J Clin Pathol 27(2): 122-124 (1974).
Dai et al., Proc Natl Acad Sci USA 89: 10892-10895 (1992).
Dall'Acqua et al., J Biol Chem 281: 23514-23524 (2006).
Dall'Acqua et al., J Immunol 117: 1129-1138 (2006).
Danos and Mulligan, Proc Natl Acad Sci USA 85; 6460-6464 (1988).
Datta-Mannan et al., J Biol Chem 282(3): 1709-1717 (2007).
Daugherty, A., et al., "Formulation and delivery issues for monoclonal antibody thera-peutics," Current Trends in Monoclonal Antibody Development and Manufacture, Chapter 8:103-129 (2010).
Deans et al., Proc Natl Acad Sci USA 81: 1292 (1984).
Dong et al, Reviews in Mol Biotech 82: 303-323 (2002).
Duncan and Winter Nature 322: 738-40 (1988).
Eglitis et al., Science 230: 1395-1398 (1985).
Eppstein et al., Proc Natl Acad Sci USA 82: 3688, 5 pages (1985).
Epstein et al., Proc Natl Acad Sci USA 82: 3688 (1985).
European Search Report, EP Application No. 161776562, dated Aug. 8, 2016, 6 pages.
Evans, et al., Mol Immunol 32(16): 1183-95 (1995).
Fakhouri, F. et al., "Terminal Complement Inhibitor Eculizumab in Adult Patients With Atypical Hemolytic Uremic Syndrome: A Single-Arm, Open-Label Trial," Am J Kidney Dis., vol. 68(1):84-93 (2016).
Fearon et al., J Exp Med 142: 856-863 (1975).
Riechmann et al., Nature 332: 323-327 (1988).
Rinder et al., J Clin Invest 96: 1564-1572 (1995).
Roberts et al., Proc. Natl. Aca. Sci., 54: 459-476 (2002).
Roeth, A. et al., "Optimization of Dose Regimen for ALXN1210, a Novel Complement C5 Inhibitor, in Patients with Paroxysmal Nocturnal Hemoglobinuria (PNH):Results of 2 Phase 1/2 Studies," Blood,vol. 130:3482 (2017).
Rogers et al., J Nucl Med 38: 1221-1229 (1997).
Rondeau, E. et al., "The long-acting C5 inhibitor, Ravulizumab, is effective and safe in adult patients with atypical hemolytic uremic syndrome naive to complement inhibitor treatment," Kidney International, Mar. 6, 2020, pp. 1-10.
Rondon and Marasco, Annual Review of Microbiology 51: 257-284 (1997).
Roopenian et al., Methods Mol Biol 602: 93-104 (2010).
Roopenian, DC, et al., "FcRn: the neonatal Fc receptor comes of age," Nature Reviews Immunology, vol. 7(9): 715-725 (2007).
Rosenfeld et al., Cell 68: 143-155 (1992).
Roth, A. et al., "Ravulizumab (ALXN1210) in patients with paroxysmal nocturnal hemo-globinuria: results of phase lb/2 studies", Blood Adv., vol. 2 (17): 2176-2185 (2018).
Rother , R. et al.,"Discovery and development of the complement inhibitor eculizumab for the treatment of paroxysmal nocturnal hemoglobinuria," Nature Biotechnology, 25 (11): 1256-1264 (1488 Supp) (2007).
Rother et al., Nature Biotechnology 25 (11): 1256-1263 (2007).
Saland, J. et al., "Liver-kidney transplantation to cure atypical HUS: still an option post-eculizumab?," Pediatr Nephrol., DOI 10.1007/s00467-013-2722-2, 4 pages (2013).
Salvadori, M. et al., "Update on hemolytic uremic syndrome: Diagnostic and therapeutic recommendations," World J Nephrol., vol. 2(3): 56-76 (2013).
Samulski et al., J Virol 63: 3822-3828 (1989).
Sarkar, C.,A., et al., "Rational cytokine design for increased lifetime and enhanced potency using pH-activated histidine switching," Nature Biotechnology, vol. 20(9):908-913 (2002).
Sarver et al., Proc Natl Acad Sci USA 79: 7147 (1982).
Sawai et al., Am J Repr Immunol 34: 26-34 (1995).
Schmid et al., Schock 8(2): 119-124 (1997).
Schoonbroodt et al., Nucleic Acids Res 33(9): e81 (2005).
Schreiber et al., Proc Natl Acad Sci USA 75: 3948-3952 (1978).
Scully, M. et al., "Systemic Involvement at Entry into the Global Atypical Hemolytic Uremic Syndrome (aHUS) Registry," Blood, vol. 128:3729 6 pages (2016).
Second Written Opinion, PCT/US2015/019225, dated Feb. 5, 2016, 10 pages.

(56) References Cited

OTHER PUBLICATIONS

Sharma, V.K. et al., "The formulation and delivery of monoclonal antibodies", Therapeutic Monoclonal Antibodies, Chapter 30: 675-711 (2009).
Sheerin, N.S. et al., "A national specialized service in England for atypical haemolytic uraemic syndrome-the first year's experience," QJM: An International Journal of Medicine, 27-33: 7 pages (2016).
Sheridan, D. et al., "Design and preclinical characterization of ALXN1210: A next generation anti-C5 monoclonal antibody with improved pharmacokinetics and duration of action," Immunobiology, vol. 221(Issue 10): 1158, 1 page (2016).
Sheridan, D. et al., "Design and preclinical characterization of ALXN1210: A novel anti-C5 antibody with extended duration of action," PLoS ONE 13(4): e0195909, 15 pages (2018).
Shields et al., J Biol Chem 276(9): 6591-6604 (2001).
Shields et al., J Biol Chem 277(30): 26733-26740 (2002).
Shire, S. et al., "High-concentration antibody formulations," Formulation and Process De-velopment Strategies for Manufacturing Biopharmaceuticals, Chapter 15: 349-381 (2010).
Shopes, Immunol 148: 2918-2922 (1992).
Shu et al., Proc Natl Aced Sci USA 90: 7995-7999 (1993).
Sissons et al., Proc Natl Acad Sci USA 77: 559-562 (1980).
Skerra et al., Science 240: 1038-1040 (1988).
Southern and Berg, Mol Appl Genet 1:327 (1982).
Wang et al.,Proc Natl Acad Sci USA 92: 8955-8959 (1995).
Staelens et al., Mol Immunol 43: 1243-1257 (2006).
Tabrizi, Ma et al., "Elimination mechanisms of therapeutic monoclonal antibodies," Drug Discovery Today, vol. 11 (1-2):81-88 (2006).
Thomas et al., Mol Immunol 33(17118): 1389-1401 (1996).
Todorovska et al., J Immunol Methods 248(1): 47-66 (2001).
Tofukuji et al., J Thorac Cardiovasc Surg 116 (6): 1060-1068 (1998).
Tsai, H. et al., "A Mechanistic Approach to the Diagnosis and Management of Atypical Hemolytic Uremic Syndrome," Transfusion Medicine Reviews, vol. 28:187-197 (2014).
Van Beusechem et al., Proc Natl Acad Sci USA 89: 7640-7644 (1992).
Van Gurp et al., Am J Transplantation 8(8): 1711-1718 (2008).
Van Kuik-Romeijn et al., Transgenic Res 9(2): 155-159 (2000).
Verhoeyen et al., Science 239: 1534-1536 (1988).
Wang et al., "Minireview Antibody Structure, Instability and Formulation," Journal of Pharmaceutical Sciences, v.96(1): 1-26 (2007).
Wang et al., Proc Natl Acad Sci USA 93: 8563-8568 (1996).
Ferry et al., Proc Natl Acad Sci USA 88: 8377-8381 (1991).
Fivash et al., Curr Opin Biotechnol 9: 97-101 (1998).
Flotte et al., Am J Respir Cell Mol Biol 7: 349-356 (1992).
Ghetie et al., Nat Biotech 15: 637-640 (1997).
Gulsen and Chauhan, Business Wire, 45: 2342-2347 (2004).
Gupta et al., Vaccine 13(14): 1263-1276 (1995).
Hanauske et al., Clin Cancer Res., NHS/NIHR, 13(2, part 1): 523-531 (2007).
Heinen, S. et al., "Monitoring and modeling treatment of atypical hemolytic uremic syndrome," Molecular Immunology, vol. 54: 84-88 (2013).
Jonsson et al., Biotechniques 11: 620-627 (1991).
Hetherington et al., Antimicrobial Agents and Chemotherapy 50(10): 3499-3500 (2006).
Hezareh et al., J Virol 75: 12161-12168 (2001).
Hillmen et al., N. Engl J Med 350(6): 552-559 (2004).
Hillmen, P. et al., "Long-term safety and efficacy of sustained eculizumab treatment in patients with paroxysmal nocturnal haemoglobinuria," British Journal of Haematology doi:10.1111/bjh.12347, 12 pages (2013).
Hinton et al., J Biol Chem 279: 6213-6216 (2004).
Hinton et al., J Immunol 176: 346-356 (2006).
Hirt-Minkowski, P., "Atypical Hemolytic Uremic Syndrome: Update on the Complement System and What Is New," Nephron Clin Pract., 114:c219-c235 (2010).
Holers and Thurman, Molecular Immunology 41: 147-152 (2004).
Holers et al., Immunological Reviews 223: 300-316 (2008).
Homeister et al., J Immunol 150: 1055-1064 (1993).
Hou et al., Cytokine 10: 319-30 (1998).
Houdebine, Curr Opin Biotechnol 13(6): 625-629 (2002).
Huber et al., Proc Natl Acad Sci USA 88: 8039-8043 (1991).
Hudson and Kortt, J Immunol Methods 231: 177-189 (1999).
Huston et al., Methods in Enzymology 203: 46-88 (1991).
Hwang et al., Proc Natl Acad Sci USA 77: 4030 (1980).
Hwu et al., J Immunol 150: 4104-4115 (1993).
Igawa et al., "Antibody recycling by engineered pH-dependent antigen binding improves the duration of antigen neutralization," Nat. Biotechnol. 28(11):1203-1207 (2010).
International Preliminary Report on Patentability, PCT/US2018/044071, dated Jan. 28, 2020, 8 pages.
International Preliminary Report on Patentability, PCT/US2018/057760, dated Apr. 28, 2020 2019, 9 pages.
International Preliminary Report on Patentability, PCT/US2019/034293, dated Dec. 1, 2020, 9 pages.
International Preliminary Report on Patentability, PCT/US2019/034297, dated Dec. 8, 2020, 10 pages.
International Preliminary Report on Patentability, PCT/US2020/058779, dated May 10, 2022, 12 pages.
International Search Report and Written Opinion for Application No. PCT/US2015/019225, dated May 18, 2015.
International Search Report and Written Opinion, PCT/US2018/044071, dated Oct. 2, 2018, 12 pages.
International Search Report and Written Opinion, PCT/US2018/057760, dated Mar. 21, 2019, 13 pages.
International Search Report and Written Opinion, PCT/US2020/014998, dated Jun. 22, 2020, 13 pages.
International Search Report and Written Opinion, PCT/US2021/040802, dated Oct. 18, 2021, 9 pages.
International Search Report and Written Opinion, PCT/US2020/058779, dated Feb. 18, 2021, 16 pages.
Isaacs et al., J Immunol 161: 3862-3869 (1998).
Isenman et al., J Immunol 124: 326-331 (1980).
Ishii-Watabe, A. et al., "Molecular Design of Therapeutic Antibodies," Pharmaceutics 74 (1): 4-11: 17 pages (2014).
Israel et al, Immunology 89(4): 573-578 (1996).
Ito, W. et al., "The His-probe method: effects of histidine residues introduced into the complementarity-determining regions of antibodies on antigen-antibody interactions at different pH values," FEBS Letter, vol. 309(1): 85-88(1992).
Janda A., et al., "Ig Constant Regions Effects on Variable Region Structure and Function," Frontiers in Microbiology, vol. 7 (22):10 pages. doi:10.3389/fmicb.2016.00022 (2016).
Johne et al., J Immunol Meth 160: 191-198 (1993).
Jorgensen L., et al., "Recent trends in stabilizing peptides and proteins in pharmaceutical formulation—considerations in the choice of excipients," Expert Opinion on Drug Delivery, vol. 6 (11): 1219-1230 (2009) doi:10.1517/17425240903199143.
Jones et al., Nature 321: 522-525 (1986).
Jonsson et al., Ann Biol Clin 51: 19-26 (1993).
Caravaca-Fontán, F. et al., "Update on C3 Glomerulopathy: A Complement-Mediated Disease," Nephron, vol. 144(6):272-280 (2020).
U.S. Appl. No. 18/086,031, filed Dec. 21, 2022, Stephan Ortiz, U.S. Pat. No. 12,012,448.

Purification Process and Bulk Fill (Continued)

High concentration UF/DF Process Diagram

Prediction Profiler for DoE Exp 02 Using JMP

SEQUENCE LISTING

<160> NUMBER OF SEQ ID NOS: 50

<210> SEQ ID NO 1
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 1

Gly Tyr Ile Phe Ser Asn Tyr Trp Ile Gln
1               5                   10

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Glu Ile Leu Pro Gly Ser Gly Ser Thr Glu Tyr Thr Glu Asn Phe Lys
1               5                   10                  15

Asp

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Tyr Phe Phe Gly Ser Ser Pro Asn Trp Tyr Phe Asp Val
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Ala Ser Glu Asn Ile Tyr Gly Ala Leu Asn
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ala Thr Asn Leu Ala Asp
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6
```

```
Gln Asn Val Leu Asn Thr Pro Leu Thr
1               5
```

```
<210> SEQ ID NO 7
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120
```

```
<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8
```

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105
```

```
<210> SEQ ID NO 9
<211> LENGTH: 326
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 10
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 11
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
             35                  40                  45

Gly Glu Ile Leu Pro Gly Ser Gly His Thr Glu Tyr Thr Glu Asn Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser
            115                 120

<210> SEQ ID NO 13
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr

```
                   260                 265                 270
Thr Pro Pro Val Leu Asp Ser Asp Gly Ser Phe Phe Leu Tyr Ser Arg
            275                 280                 285

Leu Thr Val Asp Lys Ser Arg Trp Gln Glu Gly Asn Val Phe Ser Cys
        290                 295                 300

Ser Val Leu His Glu Ala Leu His Ser His Tyr Thr Gln Lys Ser Leu
305                 310                 315                 320

Ser Leu Ser Leu Gly Lys
                325

<210> SEQ ID NO 14
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285
```

```
Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
        435                 440                 445
```

<210> SEQ ID NO 15
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 15

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Tyr Ile Thr Arg Glu Pro Glu Val Thr Cys Val Val Val Asp
130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 16
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Thr Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys

```
                210                 215                 220
Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
                260                 265                 270

Glu Val Gln Phe Asn Trp Tyr Val Asp Gly Met Glu Val His Asn Ala
                275                 280                 285

Lys Thr Lys Pro Arg Glu Glu Gln Phe Asn Ser Thr Phe Arg Val Val
                290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Glu Asn Ile Tyr His Ala Leu Asn
1               5                   10

<210> SEQ ID NO 18
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Glu Ile Leu Pro Gly Ser Gly His Thr Glu Tyr Thr Glu Asn Phe Lys
1               5                   10                  15

Asp

<210> SEQ ID NO 19
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gly His Ile Phe Ser Asn Tyr Trp Ile Gln
1               5                   10

<210> SEQ ID NO 20
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
```

```
                    290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Tyr Ala Ile Ser
1               5

<210> SEQ ID NO 22
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Gly Pro Phe Phe Gly Thr Ala Asn Tyr Ala Gln Lys Phe Gln
1               5                   10                  15

Gly

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Thr Pro Tyr Phe Asp Tyr
1               5

<210> SEQ ID NO 24
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Gly Asp Ser Ile Pro Asn Tyr Tyr Val Tyr
1               5                   10

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Asp Ser Asn Arg Pro Ser
1               5

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gln Ser Phe Asp Ser Ser Leu Asn Ala Glu Val
1               5                   10

<210> SEQ ID NO 27
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Val Trp Arg Gln Ala Pro Gly Gln Gly Leu Glu Trp Met
            35                  40                  45

Gly Gly Ile Gly Pro Phe Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Tyr Phe Asp Tyr Trp Gly Gln Gly Thr Leu Val
                100                 105                 110

Thr Val Ser Ser
            115
```

```
<210> SEQ ID NO 28
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Glu Leu Thr Gln Pro Pro Ser Val Ser Val Ala Pro Gly Gln
1               5                   10                  15

Thr Ala Arg Ile Ser Cys Ser Gly Asp Ser Ile Pro Asn Tyr Tyr Val
            20                  25                  30

Tyr Trp Tyr Gln Gln Lys Pro Gly Gln Ala Pro Val Leu Val Ile Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Phe Asp Ser Ser Leu Asn Ala
                85                  90                  95

Glu Val Phe Gly Gly Gly Thr Lys Leu Thr Val Leu
            100                 105

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asn Tyr Ile Ser
1

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ile Ile Asp Pro Asp Asp Ser Tyr Thr Glu Tyr Ser Pro Ser Phe Gln
1               5                   10                  15

Gly

<210> SEQ ID NO 31
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Glu Tyr Gly Gly Phe Asp Ile
1               5
```

```
<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Gly Asp Asn Ile Gly Asn Ser Tyr Val His
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Asp Asn Asp Arg Pro Ser
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Thr Tyr Asp Ile Glu Ser Tyr Val
1               5

<210> SEQ ID NO 35
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Ile Ser Trp Val Arg Gln Met Pro Gly Lys Gly Leu Glu Trp Met Gly
        35                  40                  45

Ile Ile Asp Pro Asp Asp Ser Tyr Thr Glu Tyr Ser Pro Ser Phe Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg Tyr Glu Tyr Gly Gly Phe Asp Ile Trp Gly Gln Gly Thr Leu Val
            100                 105                 110

Thr Val Ser Ser
```

<210> SEQ ID NO 36
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Ser Tyr Val
            20                  25                  30

His Trp Tyr Gln Gln Lys Pro Gly Gln Ala Pro Val Leu Val Ile Tyr
        35                  40                  45

Lys Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Tyr Asp Ile Glu Ser Tyr Val
                85                  90                  95

Phe Gly Gly Gly Thr Lys Leu Thr Val Leu
            100                 105
```

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

```
Ser Ser Tyr Tyr Val Ala
1               5
```

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

```
Ala Ile Tyr Thr Gly Ser Gly Ala Thr Tyr Lys Ala Ser Trp Ala Lys
1               5                   10                  15

Gly
```

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Asp Gly Gly Tyr Asp Tyr Pro Thr His Ala Met His Tyr
1               5                   10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gln Ala Ser Gln Asn Ile Gly Ser Ser Leu Ala
1               5                   10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Ala Ser Lys Thr His Ser
1               5

<210> SEQ ID NO 42
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gln Ser Thr Lys Val Gly Ser Ser Tyr Gly Asn His
1               5                   10

<210> SEQ ID NO 43
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Ser His Ser Ser
            20                  25                  30

Tyr Tyr Val Ala Trp Val Arg Gln Ala Pro Gly Lys Gly Leu Glu Trp
        35                  40                  45

Val Gly Ala Ile Tyr Thr Gly Ser Gly Ala Thr Tyr Lys Ala Ser Trp
    50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Gly Gly Tyr Asp Tyr Pro Thr His Ala Met His Tyr

```
                     100                 105                 110

Trp Gly Gln Gly Thr Leu Val Thr Val Ser Ser
            115                 120

<210> SEQ ID NO 44
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110

<210> SEQ ID NO 45
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
        435                 440                 445

Leu Ser Pro
    450

<210> SEQ ID NO 46
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

```
Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

<210> SEQ ID NO 47
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
                100                 105                 110

Gly Thr Leu Val Thr Val Ser Ser
            115                 120
```

<210> SEQ ID NO 48
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Ala Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys
                100                 105

<210> SEQ ID NO 49
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 50
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

-continued

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

METHODS OF PRODUCING ANTI-C5 ANTIBODIES

CROSS-REFERENCE TO RELATED APPLICATIONS

This application is a 35 U.S.C. 371 national stage filing of International Application No. PCT/US2019/039557, filed on Jun. 27, 2019, which claims the benefit of U.S. Provisional Application Ser. No. 62/691,428, filed on Jun. 28, 2018 and U.S. Provisional Application Ser. No. 62/811,710, filed on Feb. 28, 2019. The entire contents of the above-referenced patent applications are incorporated herein by reference.

SEQUENCE LISTING

The instant application contains a Sequence Listing that has been submitted electronically in ASCII format and is hereby incorporated by reference in its entirety. Said ASCII copy, created on Dec. 21, 2020, is named AXJ-250_Sequence_Listing.txt and is 58,869 bytes in size.

BACKGROUND

Antibodies are heavily utilized in diagnostic, therapeutic and biological research applications. Antibody stability, however, presents a challenge in the purification and formulation of these proteins. Antibody instability leads to high levels of aggregation in protein formulations, which can have several disadvantages, including changes in protein activity and potentially undesirable immunological responses in patients. There is, accordingly, a longstanding need for improved techniques to enhance the production and purification processes and increase product recovery. The present disclosure addresses this need and provides additional benefits.

SUMMARY

Provided herein are methods for producing an anti-C5 antibody (e.g., ravulizumab).

In one embodiment, the methods described herein comprising culturing mammalian cells (e.g., Chinese Hamster Ovary (CHO) cells) comprising a nucleic acid encoding the anti-C5 antibody (e.g., ravulizumab) in a cell culture production medium, such that the anti-C5 antibody is produced in said cell culture production medium, followed by one or more (e.g., one, two, three, four, five, six, seven, or eight) steps selected from the group consisting of: a recovery step; purification by Protein A affinity chromatography; a low pH viral inactivation step; purification by cation exchange chromatography (CEX); purification by anion exchange chromatography (AEX); a virus reduction filtration step; a concentration and diafiltration step; and a bulk filtration step.

In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by purification by Protein A affinity chromatography. In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by a low pH viral inactivation step. In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by purification by CEX. In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by purification by AEX. In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by a virus reduction filtration step. In another embodiment, the method comprises culturing mammalian cells comprising a nucleic acid encoding the anti-C5 antibody (e.g., ravulizumab) in a cell culture production medium, such that the anti-C5 antibody is produced in said cell culture production medium, followed by concentration and a diafiltration/ultrafiltration step.

In another embodiment, the methods described herein comprising culturing mammalian cells comprising a nucleic acid encoding the anti-C5 antibody (e.g., ravulizumab) in a cell culture production medium, such that the anti-C5 antibody is produced in said cell culture production medium, followed by one or more (e.g., one, two, three, four, five, six, seven, or eight) steps, including purification by CEX and/or AEX.

In another embodiment, the methods described herein comprising culturing mammalian cells comprising a nucleic acid encoding the anti-C5 antibody (e.g., ravulizumab) in a cell culture production medium, such that the anti-C5 antibody is produced in said cell culture production medium, followed by one or more (e.g., one, two, three, four, five, six, seven, or eight) steps, including a single diafiltration/ultrafiltration step (i.e., no more than one diafiltration/ultrafiltration step).

Also provided are methods of producing an anti-C5 antibody, wherein the method comprises:
    a. culturing mammalian cells comprising a nucleic acid encoding the anti-C5 antibody in a cell culture production medium, such that the anti-C5 antibody is produced in said cell culture production medium;
    b. a recovery step;
    c. purification by Protein A affinity chromatography;
    d. a low pH viral inactivation step;
    e. purification by CEX;
    f. purification by AEX;
    g. a virus reduction filtration step; and
    h. a concentration and diafiltration step.

In another embodiment, the method further comprises a bulk filtration step.

In another embodiment, the method consists of:
    a. culturing mammalian cells comprising a nucleic acid encoding the anti-C5 antibody in a cell culture production medium, such that the anti-C5 antibody is produced in said cell culture production medium;
    b. a recovery step;
    c. purification by Protein A affinity chromatography;
    d. a low pH viral inactivation step;
    e. purification by CEX;
    f. purification by AEX;
    g. a virus reduction filtration step; and
    h. a concentration and diafiltration step.

In another embodiment, the method further comprises a bulk filtration step.

In one embodiment, steps (a)-(h) are performed sequentially in order. For example, in one embodiment, the method comprises (a) culturing mammalian cells comprising a nucleic acid encoding the anti-C5 antibody in a cell culture production medium, such that the anti-C5 antibody is produced in said cell culture production medium, followed by (b) a recovery step, followed by (c) purification by Protein A affinity chromatography, followed by (d) a low pH viral inactivation step, followed by (e) purification by CEX, followed by (f) purification by AEX, followed by (g) a virus reduction filtration step, followed by (h) a concentration and diafiltration step, and optionally followed by a bulk filtration step.

In another embodiment, steps (a)-(h) are performed in any order and/or in any combination. For example, in one embodiment, purification by AEX is performed before purification by CEX. In another embodiment, any and/or all of the purification steps are performed before the low pH viral inactivation and/or virus reduction filtrations step(s).

In another embodiment, the method includes no more than ten steps. In another embodiment, the method includes no more than nine steps. In another embodiment, the method includes no more than eight steps. In another embodiment, the method includes no more than seven steps. In another embodiment, the method includes no more than six steps. In another embodiment, the method includes no more than five steps.

The methods described herein can also include a recovery step that comprises filtering the cell culture production medium. In one embodiment, the cell culture production medium is a commercially available cell culture medium (e.g., from Life Technologies). In another embodiment, the cell culture production medium is not a custom made cell culture production medium. In another embodiment, the cell culture production medium is a protein free and chemically defined cell culture production medium. In another embodiment, the cell culture production medium does not include bovine serum albumin.

In one embodiment, the cell culture medium is filtered by depth filtration. In another embodiment, the cell culture medium is filtered through a depth filtration train (e.g., a two-step depth filtration train), followed by additional filtration (e.g., through two 0.5/0.2 μm filters in series) into a container (e.g., a 2,000 L single-use mixing bioprocess container). In another embodiment, the depth filtration train is flushed with WFI and equilibrated with a buffer prior to use. In another embodiment, the equilibration buffer and/or chasing buffer comprises Tris (e.g., 20 mM or about 20 mM) and sodium chloride (e.g., 65 mM or about 65 mM) at a pH of about 7.6 (e.g., pH of 7.4, 7.5, 7.6, 7.7 or 7.8). In another embodiment, the equilibration buffer comprises 20 mM Tris (pH 7.6) and 65 mM sodium chloride. In another embodiment, the cell culture production medium is chased (e.g., flushed) through the two-step depth filtration train with a buffer, e.g., a buffer comprising 20 mM Tris (pH 7.6) and 65 mM sodium chloride. In another embodiment, the recovery step yields clarified harvest material.

In another embodiment, the processing conditions for the recovery step include one or more (e.g., one, two, three, four, five, six, seven, eight, nine or ten), of the following: a D0HC depth filter load of ≤100 L/m$^2$ in the NOR and ≤100 L/m$^2$ in the PAR; an A1HC depth filter load of ≤200 L/m$^2$ in the NOR and ≤200 L/m$^2$ in the PAR; a 0.5/0.2 μm filter load of ≤800 L/m$^2$ in the NOR and ≤800 L/m$^2$ in the PAR; a harvest load temperature of 18-37° C. in the NOR and 15-37° C. in the PAR; a buffer chase volume of 20-25 L/m$^2$ in the NOR and 0-30 L/m$^2$ in the PAR; a clarified harvest hold time (start of harvest filtration through end of final Pro A cycle load) of ≤10 days in the NOR and ≤16 days in the PAR; a yield of ≥70%; a total filtration time (start through end of harvest filtration, excluding flush and equilibration) of <3.3 hours; a bioburden of <3 CFU/10 mL; and/or an endotoxin concentration of <5 EU/mL.

In one embodiment, material from a previous step (e.g., clarified harvest material from the recovery step) is loaded onto a Protein A column through a filter (e.g., 0.5/0.2 μm filter).

In another embodiment, the Protein A affinity chromatography step includes the use of one or more (e.g., one, two, three, four, five, six, seven, eight, or nine) buffers, including, but not limited to: (a) sodium hydroxide, (b) tris and sodium chloride, (c) sodium phosphate, sodium chloride, and arginine hydrochloride, (d) sodium acetate, (e) acetic acid, (f) Water For Injection (WFI), and (g) ethanol. In one embodiment, the Protein A affinity chromatography step includes 0.1 N sodium hydroxide for sanitization. In another embodiment, the Protein A affinity chromatography step includes 20 mM tris and 65 mM sodium chloride at a pH of about 7.6 for equilibration and post-load wash 1. In another embodiment, the Protein A affinity chromatography step includes 50 mM sodium phosphate, 100 mM sodium chloride, and 300 mM arginine hydrochloride at a pH of 6.0 for post-load wash 2. In another embodiment, the Protein A affinity chromatography step includes 20 mM tris and 65 mM sodium chloride at a pH of about 7.6 for post-load wash 3. In another embodiment, the Protein A affinity chromatography step includes 25 mM sodium acetate at a pH of 3.75 for elution. In another embodiment, the Protein A affinity chromatography step includes 100 mM acetic acid for stripping. In another embodiment, the Protein A affinity chromatography step includes WFI for flushing. In another embodiment, the Protein A affinity chromatography step includes 20% ethanol for storage.

In another embodiment, the processing conditions for the Protein A affinity chromatography include one or more (e.g., one, two, three, four, five, six, seven, or eight) of the following:

a. a pre-batch sanitization hold time of 30-60 minutes in the Normal Operating Range (NOR) and 30-75 minutes in the Proven Acceptable Range (PAR);
b. a post-batch sanitization hold time of 30-60 minutes in the Normal Operating Range (NOR) and 30-75 minutes in the Proven Acceptable Range (PAR);
c. column cycles of ≤100 in the Normal Operating Range (NOR) and ≤100 in the Proven Acceptable Range (PAR);
d. an eluate hold time (end of filtration through start of low pH acidification) of ≤7 days in the Normal Operating Range (NOR) and ≤10 days in the Proven Acceptable Range (PAR);
e. a step yield of ≥70%;
f. an eluate pre-filtration bioburden of <50 CFU/10 mL
g. an eluate post-filtration bioburden of <3 CFU/10 mL; and/or
h. an eluate post-filtration endotoxin of <5 EU/mL.

The methods described herein can also include a low pH viral inactivation step. In one embodiment, the direct vation step comprises treating material from the previous step (e.g., an eluated pool from the Protein A affinity chromatography purification) with acetic acid, confirming low pH (e.g., within a pH of 3.60 to 3.75), increasing the pH, and then filtering out neutralized viral inactivated material. In another embodiment, the low pH viral inactivation step comprises (a) treating material from the previous step (e.g., an eluated pool from the Protein A affinity chromatography purification) with acetic acid (e.g., 1 M acetic acid at a pH range of 3.60-3.70), (b) transferring the pool to a second vessel and incubating it at ambient temperature for a minimum of 60 minutes without mixing and confirming pH range to be within 3.60 to 3.75; (c) increasing to pH 5.0 (e.g., using 1M Tris) and incubating at ambient temperature for a minimum of 60 minutes without mixing; (d) pre-filtering (e.g., 0.5/0.2 µm filter) neutralized viral inactivated material; and storing the filtered product.

In another embodiment, the processing conditions for the low pH viral inactivation step include one or more (e.g., one, two, three, four, five, six, seven, eight, nine, or ten) of the following:
a. an acidification pH immediately after titration of 3.60-3.70 in the Normal Operating Range (NOR) and 3.55-3.80 in the Proven Acceptable Range (PAR);
b. an acidification pH immediately after hold time of 3.60-3.75 in the Normal Operating Range (NOR) and 3.55-3.80 in the Proven Acceptable Range (PAR);
c. a hold time at low pH of 60-120 minutes in the Normal Operating Range (NOR) and ≥60-360 minutes in the Proven Acceptable Range (PAR);
d. a hold time at neutralized pH prior to 0.5/0.2 µm filtration of 60-120 minutes in the Normal Operating Range (NOR) and ≥60 minutes in the Proven Acceptable Range (PAR);
e. a filtered neutralized product hold time (end of filtration through end of CEX load) of ≤7 days;
f. in the Normal Operating Range (NOR) and ≤7 days in the Proven Acceptable Range (PAR);
g. a yield of ≥90%;
h. a neutralized pre-filtration pool bioburden of <50 CFU/10 mL;
i. a neutralized post-filtration pool bioburden of <3 CFU/10 mL; and/or
j. a neutralized post-filtration pool endotoxin of <5 EU/mL.

The methods described herein can also include a cation exchange chromatography (CEX) step. For example, in one embodiment, the methods described herein comprising culturing mammalian cells comprising a nucleic acid encoding the anti-C5 antibody (e.g., ravulizumab) in a cell culture production medium, such that the anti-C5 antibody is produced in said cell culture production medium, followed by one or more (e.g., one, two, three, four, five, six, seven, or eight) steps, including purification by CEX and/or AEX.

In one embodiment, material from the previous step (e.g., neutralized filtrate from the low pH viral inactivation step) is loaded onto a cation exchange column (e.g., a POROS HS50 cation exchange column), for example, through a 0.5/0.2 µm filter. In one embodiment, the CEX step includes the use of one or more (e.g., one, two, three, four, five, six, seven, eight, or nine) buffers, including, but not limited to: (a) sodium acetate, (b) sodium chloride, (c) sodium hydroxide, (d) sodium acetate and sodium chloride, and (e) sodium acetate, sodium chloride, and arginine hydrochloride. In another embodiment, the CEX buffer comprises 50 mM Sodium Acetate at a pH of 5.0 for equilibration and post-load wash 1. In another embodiment, the CEX buffer comprises 50 mM sodium acetate and 60 mM sodium chloride at a pH of 4.9 for post-load wash 2. In another embodiment, the CEX buffer comprises 50 mM sodium acetate, 90 mM arginine hydrochloride, and 30 mM sodium chloride at a pH of 5.0 for elution. In another embodiment, the CEX buffer comprises 2.0 M sodium chloride for stripping. In another embodiment, the CEX buffer comprises 1.0 N sodium hydroxide for sanitization. In another embodiment, the CEX buffer comprises 0.1 N sodium hydroxide for storage.

In another embodiment, the processing conditions for the CEX include one or more (e.g., one, two, three, four, five, six, seven, eight, nine, ten, or 11) of the following:
a. a load capacity of 22-45 g/L in the Normal Operating Range (NOR) and 15-50 g/L in the Proven Acceptable Range (PAR);
b. a temperature of 15-25° C. in the Normal Operating Range (NOR) 13-27° C. in the Proven Acceptable Range (PAR);
c. an elution buffer pH of 4.90-5.10 in the Normal Operating Range (NOR) and 4.90-5.10 in the Proven Acceptable Range (PAR);
d. an elution buffer conductivity of 11.1-13.6 mS/cm in the Normal Operating Range (NOR) and 11.1-13.6 mS/cm in the Proven Acceptable Range (PAR);
e. an elution flow rate of 150-300 cm/hr in the Normal Operating Range (NOR) and 120-330 cm/hr in the Proven Acceptable Range (PAR);
f. an eluate hold time (start of eluate collection through end of AEX load adjustment) of ≤7 days in the Normal Operating Range (NOR) and ≤10 days in the Proven Acceptable Range (PAR);
g. column cycles of ≤100 in the Normal Operating Range (NOR) and ≤100 in the Proven Acceptable Range (PAR);
h. an eluate post-filtration bioburden of <3 CFU/10 mL;
i. an eluate post-filtration endotoxin of <5 EU/mL;
j. a step yield of ≥58%; and/or
k. an eluate volume of 2.3-5.0 column volumes.

The methods described herein can also include an AEX step. In one embodiment, material from the previous step (e.g., an eluated pool from the CEX step) is pH adjusted prior to loading on to an AEX column. In another embodiment, material from the previous step (e.g., the eluated pool from the CEX step) is pH adjusted using tris, arginine, and WFI. In another embodiment, material from the previous step (e.g., the eluated pool from the CEX step) is adjusted to a pH of approximately 8.0. In another embodiment, material from the previous step (e.g., the eluated pool from the CEX step) is adjusted to a conductivity of 8.5 mS/cm. In another embodiment, material from the previous step (e.g., the eluated pool from the CEX step) is adjusted to a pH of 8.00 and a conductivity of 8.5 mS/cm with 100 mM Tris at 180 mM Arginine at a pH of 9.0 and WFI.

In another embodiment, the AEX column is a POROS HQ50 AEX column. In another embodiment, the AEX column is a POROS HQ50 AEX column operated in flow-through mode. In another embodiment, material from the previous step (e.g., the adjusted eluated pool) is loaded on to an AEX column within 24 hours (e.g., within 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, or 23 hours) of the adjustment. In another embodiment, material from the previous step (e.g., the adjusted eluated pool) is loaded on to an AEX column through a filter (e.g., 0.5/0.2 µm filter) and the resulting product is chased (e.g., flushed) from the AEX column, e.g., using buffer filtered through an filter (e.g., 0.5/0.2 µm filter) into a filtrate vessel.

In another embodiment, the AEX step includes the use of one or more (e.g., one, two, three, four, five, six, seven, eight, or nine) buffers, including, but not limited to: (a) tris and arginine, (b) WFI, (c) sodium chloride, (d) tris and sodium chloride, and (e) sodium hydroxide. In another embodiment, the AEX step includes the use of 100 mM Tris and 180 mM Arginine at a pH of 9.0 for load pH adjustment. In another embodiment, the AEX step includes the use of WFI for load conductivity adjustment and flush. In another embodiment, the AEX step includes the use of 2 M Sodium Chloride for conditioning. In another embodiment, the AEX step includes the use of 20 mM Tris and 65 mM Sodium Chloride at a pH of 7.6 for equilibration and post-load chase. In another embodiment, the AEX step includes the use of 2 M Sodium Chloride for post-load elution stripping. In another embodiment, the AEX step includes the use of 1.0 N Sodium Hydroxide for sanitization. In another embodiment, the AEX step includes the use of 0.1 N Sodium Hydroxide for storage.

In another embodiment, the processing conditions for the AEX include one or more (e.g., one, two, three, four, five, six, seven, eight, nine, ten, or 11) of the following:
 a. a load pH of 7.90-8.10 in the Normal Operating Range (NOR) and 7.80-8.20 in the Proven Acceptable Range (PAR);
 b. a load conductivity of 8.0-9.0 mS/cm in the Normal Operating Range (NOR) and 7.0-10.0 mS/cm in the Proven Acceptable Range (PAR); and
 c. a load capacity pH of 25-90 g/L in the Normal Operating Range (NOR) and 25-100 g/L in the Proven Acceptable Range (PAR);
 d. a hold time (AEX load adjustment through start of AEX Load) of ≤1 day in the Normal Operating Range (NOR) and ≤4 days in the Proven Acceptable Range (PAR);
 e. a product hold time (end of AEX load adjustment through end of UF/DF) of ≤4 days in the Normal Operating Range (NOR) and ≤6 days in the Proven Acceptable Range (PAR);
 f. column cycles of ≤100 in the Normal Operating Range (NOR) and ≤100 in the Proven Acceptable Range (PAR);
 g. an eluate bioburden (post-filtration) of <3 CFU/10 mL; and/or
 h. an eluate Endotoxin (post-filtration) of <5 EU/mL; and a yield of ≥67%.

The methods described herein can also include a filtration step to remove viruses or virus-like particles. In one embodiment, the filters are flushed prior to use (e.g., using WFI and buffer). In another embodiment, flow through filtrate from the AEX is filtered through a virus filter (e.g., 0.5/0.2 μm), followed by filtration through a virus filter (e.g., 20 nm).

In another embodiment, the filtration step to remove viruses or virus-like particles includes the use of one or more (e.g., one, two, three, four, five, six, seven, eight, or nine) buffers, including, but not limited to: (a) tris and sodium chloride and (b) WFI. In another embodiment, the filtration step to remove viruses or virus-like particles includes the use WFI as a pre-use flush. In another embodiment, the filtration step to remove viruses or virus-like particles includes the use of 20 mM Tris and 65 mM Sodium Chloride at a pH of 7.6 for equilibration and post-loading chase.

In another embodiment, the filtration step to remove viruses or virus-like particles includes one or more (e.g., one, two, three, four, five, six, seven, eight, nine, ten, eleven, or twelve) of the following:
 a. a virus filter Differential Pressure During Load and Chase of 21-32 psid in the Normal Operating Range (NOR) and 21-35 psid in the Proven Acceptable Range (PAR);
 b. a Total Pause Time during Load and Chase of 0 minutes in the Normal Operating Range (NOR) and ≤120 minutes in the Proven Acceptable Range (PAR);
 c. a chase volume of ≤15 L/m$^2$ in the Normal Operating Range (NOR) and ≤20 L/m$^2$ in the Proven Acceptable Range (PAR);
 d. pass a post-use integrity test;
 e. a load concentration of 3.0-6.0 g/L in the Normal Operating Range (NOR) and ≤6.7 g/L in the Proven Acceptable Range (PAR);
 f. a shield H pre-filter load of ≤700 L/m$^2$ in the Normal Operating Range (NOR) and ≤1200 L/m$^2$ in the Proven Acceptable Range (PAR);
 g. a virus filter load of ≤700 L/m$^2$ in the Normal Operating Range (NOR) and ≤700 L/m$^2$ in the Proven Acceptable Range (PAR);
 h. a product hold time (end of AEX load adjustment through end of UFDF) of ≤4 days in the Normal Operating Range (NOR) and ≤6 days in the Proven Acceptable Range (PAR);
 i. a bioburden (pre-filtration viral filter load) of <3 CFU/10 mL;
 j. an endotoxin (viral filtrate) of <2 EU/mL;
 k. pass a pre-use integrity test; and/or
 l. a processing time (start of load to end of load) of ≤12 hours; and/or a step yield of ≥90%.

The methods described herein can also include a concentration and diafiltration step. For example, in one embodiment, the methods described herein comprising culturing mammalian cells comprising a nucleic acid encoding the anti-C5 antibody in a cell culture production medium, such that the anti-C5 antibody is produced in said cell culture production medium, followed by one or more (e.g., one, two, three, four, five, six, seven, or eight) steps, including a single diafiltration/ultrafiltration step (i.e., no more than one diafiltration/ultrafiltration step).

In one embodiment, material from the previous step (e.g., a pool from the virus filtration step) is ultrafiltrated and concentrated. In another embodiment, the pool is further diafiltered. In another embodiment, the concentration of the product is measured and diluted (e.g., to 10.0 g/L or 100 g/L). In another embodiment, material from the previous step (e.g., a pool from the virus filtration) is (a) ultrafiltrated and concentrated, e.g., to 55 g/L using 30 kDa MWCO UF membranes, (b) diafiltered (e.g., with 6 diafiltration volumes) into a formulation buffer and the product concentration is measured and diluted (e.g., to 10.0 g/L or 100 g/L). In another embodiment, the formulation buffer comprises 10 mM sodium phosphate and 150 mM sodium chloride at a pH of 7.0. In another embodiment, the diluted product is filtered (e.g., through a 0.5/0.2 μm filter) and Polysorbate 80 is added to a diluted product pool to achieve a final concentration of 0.02% (w/v) Polysorbate 80.

In another embodiment, the concentration and/or diafiltration steps include the use of one or more (e.g., one, two, three, four, five, six, seven, eight, or nine) buffers, including, but not limited to: (a) WFI, (b) sodium hydroxide, (c) sodium phosphate and 150 mM sodium chloride, and (d) polysorbate 80. In another embodiment, the concentration and/or diafiltration steps include the use of WFI as a flush. In another embodiment, the concentration and/or diafiltration steps include the use of 0.5 M sodium hydroxide for sanitization. In another embodiment, the concentration and/or diafiltration steps include the use of 10 mM Sodium Phosphate and 150 mM Sodium Chloride at a pH of 7.0 for equilibration, diafiltration, chase, and/or pool dilution. In another embodiment, the concentration and/or diafiltration steps include the use of 0.1 M sodium hydroxide for storage.

In another embodiment, the concentration and/or diafiltration steps include the use of 10% (w/v) Polysorbate 80 for excipient.

In another embodiment, the concentration and/or diafiltration steps include one or more (e.g., one, two, three, four, five, six, seven, eight, nine, ten, eleven, twelve, thirteen, fourteen, fifteen, sixteen, seventeen, eighteen, or nineteen) of the following:
a. a dilution of within 1% of calculated volume in the Normal Operating Range (NOR) and within 3% of calculated volume in the Proven Acceptable Range (PAR);
b. 10% (w/v) Polysorbate 80 is 0.19-0.21% (w/v) of diluted UF/DF product in the Normal Operating Range (NOR) and 0.17-0.23% (w/v) of diluted UF/DF product in the Proven Acceptable Range (PAR);
c. an un-formulated drug substance pH of 6.5-7.5;
d. a diluted UF/DF product concentration of 9.0-11.0 mg/mL;
e. passing a pre-use integrity test;
f. a membrane loading of 100-500 g/m$^2$ in the Normal Operating Range (NOR) and within 50-600 g/m$^2$ in the Proven Acceptable Range (PAR);
g. a feed flux of 240-420 LMH in the Normal Operating Range (NOR) and within 180-440 LMH in the Proven Acceptable Range (PAR);
h. a transmembrane pressure of 10-30 psi in the Normal Operating Range (NOR) and within 8-35 psi in the Proven Acceptable Range (PAR);
i. a pressure of 15-25° C. in the Normal Operating Range (NOR) and within 12-30° C. in the Proven Acceptable Range (PAR);
j. a fed batch ratio of 1-3 in the Normal Operating Range (NOR) and within 1-5 in the Proven Acceptable Range (PAR);
k. a concentration at end of ultrafiltration target of 13-17 g/L in the Normal Operating Range (NOR) and within 12-20 g/L in the Proven Acceptable Range (PAR);
l. a diavolume of 5.5-7.0 in the Normal Operating Range (NOR) and within 4.5-7.0 in the Proven Acceptable Range (PAR);
m. an unformulated ultrafiltration and diafiltration retentate hold of ≤4 days in the Normal Operating Range (NOR) and within ≤6 days in the Proven Acceptable Range (PAR);
n. a product hold (diluted ultrafiltrated/diafiltrated product) of ≤7 days in the Normal Operating Range (NOR) and within ≤14 days in the Proven Acceptable Range (PAR);
o. a step yield of ≥90%;
p. a processing time (start of initial concentration through end of diafiltration) of ≤11.1 hours;
q. a post-use NWP of 75-125% of initial;
r. a diluted ultrafiltrated/diafiltrated pre-filtration pool bioburden of <10 CFU/10 mL; and/or
s. a diluted ultrafiltrated/diafiltrated post-filtration pool bioburden of <3 CFU/10 mL; and/or a diluted ultrafiltrated/diafiltrated post-filtration pool endotoxin of <2 EU/mL.

In another embodiment, the concentration and/or diafiltration steps include one or more (e.g., one, two, three, four, five, six, seven, eight, nine, ten, eleven, twelve, thirteen, fourteen, fifteen, sixteen, seventeen, eighteen, nineteen, or twenty) of the following:
a. an initial concentration target of 40-60 g/L;
b. a final concentration target (140-160 g/L) (includes 1.07 recovery factor);
c. a diavolume of 4.5-7.5, with a target of 6.0;
d. an undiluted ultrafiltrated/diafiltrated product hold of ≤24 hours);
e. a diluted ultrafiltrated/diafiltrated product hold of ≤24 hours);
f. use of a Millipore Pellicon 3 Ultracel C screen 30 kDa MWCO filter;
g. a flush WFI≥20 L/m$^2$;
h. an equilibrium of 50 mM NaPO$_4$ (pH 7.4), 25 mM L-Arg (≥20 L/m$^2$)
i. a membrane load of ≤600 L/m$^2$;
j. a target feed flow rate for all product steps of 360 LMH;
k. a target transmembrane pressure for all product steps of 15 psi;
l. a feed pressure or ≤50 psi (can be increased);
m. a diafiltration buffer that is the same as equilibrium;
n. a final concentration that can be controlled by feed pressure (not TMP or Feed Flow Rate);
o. a temperature or 15-35° C.;
p. a recovery with ≤1× system hold-up volume (calculation required per CSD);
q. a dilution to target 120 g/L with DF/equilibrium buffer;
r. 0.1919-0.2393 kg/kg addition of excipient addition buffer (EAB—50 mM NaPO$_4$ (pH 7.4), 25 mM L-Arg, 30% Sucrose 0.30% (w/v), PS 80) to 120 g/L UF/DF product for final formulation;
s. membrane re-use up to 20 cycles;
t. sanitization with 0.5 M NaOH.
u. storage with 0.1 M NaOH;
v. a yield of >60% (expected over 90%);
w. express SHC filterability 120 g/L UF/DF product: ≤40 L/m$^2$; and
x. express SHC filterability BDS of ≤3045 L/m$^2$.

An exemplary anti-C5 antibody is ravulizumab (also known as ALXN1210 and antibody BNJ441) comprising the heavy and light chains having the sequences shown in SEQ ID NOs:14 and 11, respectively, or antigen binding fragments and variants thereof. In other embodiments, the antibody comprises the heavy and light chain complementarity determining regions (CDRs) or variable regions (VRs) of ravulizumab. Accordingly, in one embodiment, the antibody comprises the CDR1, CDR2, and CDR3 domains of the heavy chain variable (VH) region of ravulizumab having the sequence shown in SEQ ID NO:12, and the CDR1, CDR2 and CDR3 domains of the light chain variable (VL) region of ravulizumab having the sequence shown in SEQ ID NO:8. In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively.

In another embodiment, the antibody comprises VH and VL regions having the amino acid sequences set forth in SEQ ID NO:12 and SEQ ID NO:8, respectively.

In another embodiment, the antibody comprises a heavy chain constant region as set forth in SEQ ID NO:13.

In another embodiment, the antibody comprises a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434, each in EU numbering.

In another embodiment, the antibody comprises CDR1, CDR2 and CDR3 heavy chain sequences as set forth in SEQ ID NOs:19, 18, and 3, respectively, and CDR1, CDR2 and CDR3 light chain sequences as set forth in SEQ ID NOs:4, 5, and 6, respectively and a variant human Fc constant region that binds to human neonatal Fc receptor (FcRn), wherein the variant human Fc CH3 constant region comprises Met-429-Leu and Asn-435-Ser substitutions at residues corresponding to methionine 428 and asparagine 434, each in EU numbering.

In another embodiment, the antibody competes for binding with, and/or binds to the same epitope on C5 as, the above-mentioned antibodies. In another embodiment, the antibody has at least about 90% variable region amino acid sequence identity with the above-mentioned antibodies (e.g., at least about 90%, 95% or 99% variable region identity with SEQ ID NO:12 and SEQ ID NO:8).

In another embodiment, the antibody binds to human C5 at pH 7.4 and 25° C. with an affinity dissociation constant ($K_D$) that is in the range 0.1 nM≤$K_D$≤1 nM. In another embodiment, the antibody binds to human C5 at pH 6.0 and 25° C. with a $K_D$≥10 nM. In yet another embodiment, the [($K_D$ of the antibody or antigen-binding fragment thereof for human C5 at pH 6.0 and at 25° C.)/($K_D$ of the antibody or antigen-binding fragment thereof for human C5 at pH 7.4 and at 25° C.)] of the antibody is greater than 25.

In another embodiment, the anti-C5 antibody comprises the heavy and light chain CDRs or variable regions of the BNJ421 antibody (described in PCT/US2015/019225 and U.S. Pat. No. 9,079,949). In another embodiment, the anti-C5 antibody comprises the heavy and light chain CDRs or variable regions of the 7086 antibody (see U.S. Pat. Nos. 8,241,628 and 8,883,158). In another embodiment, the anti-C5 antibody comprises the heavy and light chain CDRs or variable regions of the 8110 antibody (see U.S. Pat. Nos. 8,241,628 and 8,883,158). In another embodiment, the anti-C5 antibody comprises the heavy and light chain CDRs or variable regions of the 305LO5 antibody (see US2016/0176954A1). In another embodiment, the anti-C5 antibody comprises the heavy and light chain CDRs or variable regions of the SKY59 antibody (see Fukuzawa T. et al., Rep. 2017 Apr. 24; 7(1):1080). In another embodiment, the anti-C5 antibody comprises the heavy and light chain CDRs or variable regions of the REGN3918 antibody (see US20170355757).

In one embodiment, the anti-C5 antibody produced according to the methods disclosed herein is formulated in a 10 mg/mL solution. In another embodiment, the anti-C5 antibody is formulated in a sterile, preservative-free 10 mg/mL solution e.g., which is suitable for IV administration. In another embodiment, the anti-C5 antibody is supplied in 20 mL single-use vials. In another embodiment, each vial contains 150 mg of ravulizumab in 10 mM sodium phosphate, 150 mM sodium chloride, 0.02% polysorbate 80, and water for injection at a pH of 7.0.

In another embodiment, the anti-C5 antibody produced according to the methods disclosed herein is formulated in a 100 mg/mL solution. In another embodiment, the anti-C5 antibody is formulated in a sterile, preservative-free 100 mg/mL solution e.g., which is suitable for subcutaneous administration. In another embodiment, the anti-C5 antibody is supplied in 2 mL single-use vials. In another embodiment, each vial contains 100 mg/mL of ravulizumab in 50 mM sodium phosphate, 25 mM arginine, 5% sucrose, and 0.05% polysorbate 80, and water for injection at a pH of 7.4.

DETAILED DESCRIPTION

Methods

Figure 1:
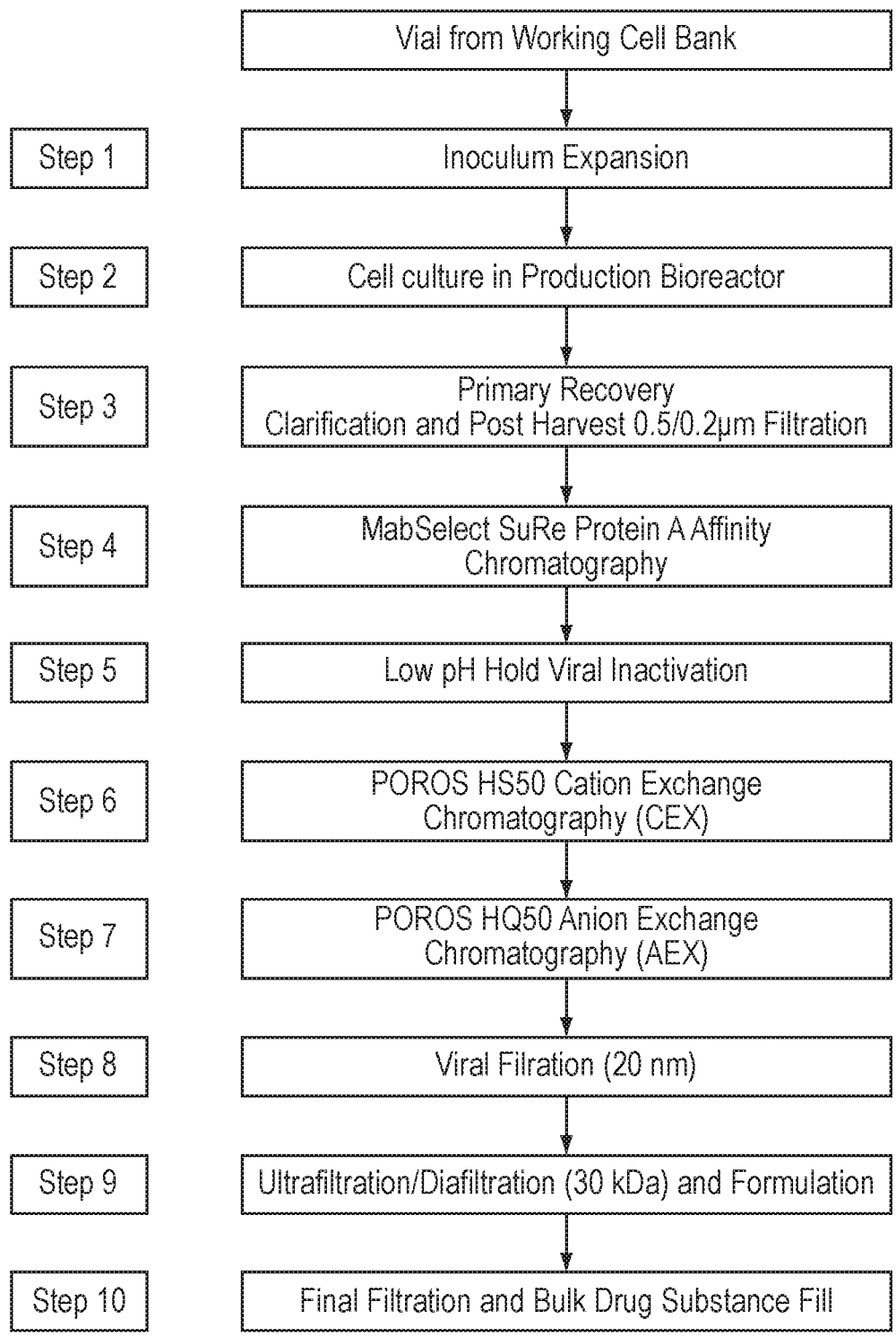
FIG. 1 is a flow diagram of the manufacturing process for ravulizumab.

Provided herein are methods for producing an antibody that binds to complement component C5 (an "anti-C5 antibody," e.g., ravulizumab).

As used herein, the terms "purifying" and "separating" are used interchangeably, and refer to the removal of contaminants from a mixture containing a protein of interest (e.g., an anti-C5 antibody).

As used herein, a "mixture" comprises a protein of interest (for which purification is desired) and one or more other components, sometimes, for example, contaminants, i.e., impurities. In one embodiment, a mixture is produced from a host cell that expresses the protein of interest (either naturally or recombinantly). Such mixtures include, for example, cell cultures, cell lysates and clarified bulk (e.g., clarified cell culture supernatant).

As used herein, the term "contaminant" is used in its broadest sense to cover any undesired component or compound within a mixture. In cell cultures, cell lysates or clarified bulk (e.g., cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants (e.g., truncated and aggregated versions of the protein of interest).

As used herein, "washing" or "chasing" refers to passing an appropriate buffer through or over a cation exchange resin or buffer.

As used herein, "eluting" refers to removing a protein of interest (e.g., an anti-C5 antibody) from a resin or column.

As used herein, a "cell culture" refers to cells in a liquid medium that produce a protein of interest (e.g., an anti-C5 antibody). The cells can be from any organism including, for example, bacteria, fungus, mammals or plants. Suitable liquid media include, for example, nutrient media and nonnutrient media. In one embodiment, the cell culture production medium is a commercially available cell culture medium (e.g., from Life Technologies). In another embodiment, the cell culture production medium is not a custom made cell culture production medium. In another embodiment, the cell culture production medium is a protein free and chemically defined cell culture production medium. In another embodiment, the cell culture production medium does not include bovine serum albumin.

As used herein, the term "clarified bulk" refers to a mixture from which particulate matter (e.g., cells) has been substantially removed. Clarified bulk includes cell culture supernatant, or cell lysate from which cells or cell debris have been substantially removed by, for example, filtration or centrifugation.

As used herein the term "chromatography" refers to the process by which a solute of interest, e.g., an anti-C5 antibody, in a mixture is separated from other solutes in the mixture by percolation of the mixture through an adsorbent, which adsorbs or retains a solute more or less strongly due to properties of the solute, such as, for example, pI, hydrophobicity, size and structure, under particular buffering conditions of the process.

The terms "ion-exchange" and "ion-exchange chromatography" refer to a chromatographic process in which an ionizable solute of interest (e.g., an anti-C5 antibody in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange (CEX), anion exchange (AEX) and mixed mode chromatographies (e.g., the combined use of two (or more) retention mechanisms in a single chromatographic system).

The term "resin" refers to an organic polymer. The polymer may be naturally occurring or synthetic. Resins are often used as solid phase support materials for chromatography.

In one embodiment, the methods described herein comprising culturing mammalian cells comprising a nucleic acid encoding, for example, an anti-C5 antibody (e.g., ravulizumab) in a cell culture production medium, such that the anti-C5 antibody is produced in the cell culture production medium, followed by one or more (e.g., one, two, three, four, five, six, seven or eight) steps selected from the group consisting of: a recovery step; purification by Protein A affinity chromatography, a low pH viral inactivation step; purification by CEX, purification by AEX; a virus reduction filtration step, and a concentration and diafiltration step.

Any suitable mammalian cell can be used for the culture step. Exemplary mammalian cells include, but are not limited to murine myeloma cells (NS0), murine hybridomas, chinese hamster ovary cells (CHO), and PER.C6 human cells. In a particular embodiment, the mammalian cells are CHO cells. In another embodiment, the mammalian cells are not NS0 cells.

In one embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by purification by Protein A affinity chromatography. In another embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by a low pH viral inactivation step. In another embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by purification by CEX. In another embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by purification by AEX. In another embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by a virus reduction filtration step. In another embodiment, the method comprises culturing mammalian cells comprising a nucleic acid encoding the anti-C5 antibody (e.g., ravulizumab) in a cell culture production medium, such that the anti-C5 antibody is produced in the cell culture production medium, followed by concentration and diafiltration step.

Also provided are methods of producing an anti-C5 antibody, wherein the method comprises culturing mammalian cells comprising a nucleic acid encoding the anti-C5 antibody in a cell culture production medium, such that the anti-C5 antibody is produced in said cell culture production medium; a recovery step; purification by Protein A affinity chromatography; a low pH viral inactivation step; purification by CEX; purification by AEX; a virus reduction filtration step; and a concentration and diafiltration step. In another embodiment, the method consists of culturing mammalian cells comprising a nucleic acid encoding the anti-C5 antibody in a cell culture production medium, such that the anti-C5 antibody is produced in said cell culture production medium; a recovery step; purification by Protein A affinity chromatography; a low pH viral inactivation step; purification by CEX; purification by AEX; a virus reduction filtration step; and a concentration and diafiltration step.

In one embodiment, purification steps are performed sequentially in the order described. In another embodiment, the purification steps are performed in any order and/or in any combination. For example, in one embodiment, purification by AEX is performed before purification by CEX. In another embodiment, any and/or all of the purification steps are performed before the low pH viral inactivation and/or virus reduction filtrations step(s).

In another embodiment, the method includes no more than ten steps. In another embodiment, the method includes no more than nine steps. In another embodiment, the method includes no more than eight steps.

Recovery Step

The methods described herein can include a recovery step that comprises centrifugation and/or filtering the cell culture production medium. In one embodiment, the cell culture medium is centrifuged. In another embodiment, the cell culture medium is filtered through depth filtration. In another embodiment, the cell culture medium is centrifuged and depth filtered. Depth filters are filters that use a porous filtration medium to retain particles throughout the medium, rather than just on the surface of the medium. These filters are commonly used when the fluid to be filtered contains a high load of particles because, relative to other types of filters, they can retain a large mass of particles before becoming clogged (Shukla, A. & Kandula, J., *Bio Pharm International*, 21:34-45, 2008).

Depth filtration is widely used for the clarification of cell culture. Cell culture systems can contain yeast, bacterial and other contaminant cells, and, hence, an efficient clarification stage is vital to separate the cells and other colloidal matter to produce a particle free cell system. Most depth filters used in pharmaceutical processes, such as cell system harvesting are composed of cellulose fibers and filter aids. The direct flow design of depth filters provides a financially suitable solution of trapping contaminants within the filter channel while ensuring the maximum recovery rate of the product. The other advantages of this system includes its low power costs, since the pumps utilized during depth filtration require minimal power input due to the low pressure within the system. Depth filtration is also flexible in terms of being able to scale up or down while outputting a high yield (>95%). For cell culture applications, depth filtration trains (e.g., two, three, four or more stage filter systems) are often used and result in more efficient processing.

In one embodiment, depth filtration is used. In another embodiment, a two-step depth filtration train is used. In another embodiment, the depth filtration train is flushed with Water For Injection (WFI) and equilibrated with a buffer prior to use. In another embodiment, the cell culture production medium is chased (e.g., flushed) through the two-step depth filtration train with a buffer. In another embodiment, the equilibration buffer and/or chasing buffer comprises Tris (e.g., 20 mM or about 20 mM), about pH 7.6 (e.g., pH of 7.4, 7.5, 7.6, 7.7. or 7.8), and sodium chloride (e.g., 65 mM or about 65 mM).

In another embodiment, additional filtration is performed after the depth filtration. In another embodiment, the additional filtration is performed through one or more 0.5/0.2 μm filters (e.g., one, two, three or four 0.5/0.2 μm filters). In another embodiment, additional filtration is performed through two 0.5/0.2 μm filters in series into a container. In one embodiment, filtration is performed into a bioprocess container (e.g., a 2,000 L single-use mixing bioprocess container). In another embodiment, the recovery step yields clarified harvest material.

In another embodiment, the processing conditions for the recovery step include one or more (e.g., one, two, three, four, five, six, seven, eight, nine or ten), of the following: a D0HC depth filter load of ≤100 L/m$^2$ in the Normal Operating Range (NOR) and ≤100 L/m$^2$ in the Proven Acceptable Range (PAR); an A1HC depth filter load of ≤200 L/m$^2$ in the NOR and ≤200 L/m$^2$ in the PAR; a 0.5/0.2 μm filter load of ≤800 L/m$^2$ in the NOR and ≤800 L/m$^2$ in the PAR; a harvest load temperature of 18-37° C. in the NOR and 15-37° C. in the PAR; a buffer chase volume of 20-25 L/m$^2$ in the NOR and 0-30 L/m$^2$ in the PAR; a clarified harvest hold time (start of harvest filtration through end of final Pro A cycle load) of ≤10 days in the NOR and ≤16 days in the PAR; a yield of ≥70%; a total filtration time (start through end of harvest filtration, excluding flush and equilibration) of <3.3 hours; a bioburden of <3 CFU/10 mL; and/or an endotoxin concentration of <5 EU/mL.

Protein A Affinity Chromatography Step

The methods described herein can include a Protein A affinity chromatography step. "Protein A affinity chromatography" refers to the separation or purification of substances and/or particles using protein A, where the protein A is generally immobilized on a solid phase. Protein A is a 40-60 kD cell wall protein originally found in *Staphylococcus aureas*. The binding of antibodies to protein A resin is highly specific. Protein A binds with high affinity to the Fc region of immunoglobulins. It binds with high affinity to human IgG1 and IgG2 as well as mouse IgG2a and IgG2b. Protein A binds with moderate affinity to human IgM, IgA and IgE, as well as to mouse IgG3 and IgG1. A protein comprising a CH2/CH3 region may be reversibly bound to, or adsorbed by, the protein A.

Protein A resins are known in the art and suitable for use in the invention. Non-limiting examples of commercially available Protein A resins include MabSelect®, MabSelect Xtra®, MabSelect SuRe®, rProtein A Sepharose® FF, rmp-Protein A Sepharose® FF, Protein A Sepharose® CL-4B and nProtein A Sepharose® 4 FF (all commercially available from GE Healthcare); ProSep® A, ProSep®-vA High Capacity, ProSep®-vA Ultra and ProSep®-Va Ultra Plus (all commercially available from Millipore); Poros® A and Mabcapture® A (both commercially available from Poros); IPA-300, IPA-400 and IPA-500 (all commercially available from RepliGen Corp.); Affi-Gel® protein A and Affi-Prep® protein A (both commercially available from Bio-Rad); Protein A Ceramic Hyper D F (commercially available from Pall Corporation); Ultralink Immobilized protein A and Agarose protein A (both commercially available from PIERCE); and Protein A Cellthru 300 and Protein A Ultra-flow (both commercially available from Sterogen Biosepa-rations). In a particular embodiment, the Protein A affinity chromatography is MabSelect SuRe® Protein A affinity chromatography. In another embodiment, the Protein A affinity chromatography is not rmp Protein A chromatography.

In one embodiment, the Protein A affinity chromatography step includes the use of one or more (e.g., one, two, three, four, five, six, seven, eight or nine) buffers, including, but not limited to: (a) sodium hydroxide, (b) tris and sodium chloride, (c) sodium phosphate, sodium chloride, and arginine hydrochloride, (d) sodium acetate, (e) acetic acid, (f) Water For Injection (WFI), and (g) ethanol. In one embodiment, the Protein A affinity chromatography step includes 0.1 N sodium hydroxide for sanitization. In another embodiment, the Protein A affinity chromatography step includes 20 mM Tris (pH 7.6) and 65 mM sodium chloride for equilibration and post-load wash 1. In another embodiment, the Protein A affinity chromatography step includes 50 mM sodium phosphate (pH 6.0), 100 mM sodium chloride, and 300 mM arginine hydrochloride for post-load wash 2. In another embodiment, the Protein A affinity chromatography step includes 20 mM Tris (pH 7.6) and 65 mM sodium chloride for post-load wash 3. In another embodiment, the Protein A affinity chromatography step includes 25 mM sodium acetate (pH 3.75) for elution. In another embodiment, the Protein A affinity chromatography step includes 100 mM acetic acid for stripping. In another embodiment, the Protein A affinity chromatography step includes WFI for flushing. In another embodiment, the Protein A affinity chromatography step includes 20% ethanol for storage. In another embodiment, clarified harvest material from the recovery step is loaded onto a Protein A column through a filter (e.g., 0.5/0.2 μm filter).

In another embodiment, the processing conditions for the Protein A affinity chromatography include one or more (e.g., one, two, three, four, five, six, seven or eight) of the following: a pre-batch sanitization hold time of 30-60 minutes in the NOR and 30-75 minutes in the PAR; a post-batch sanitization hold time of 30-60 minutes in the NOR and 30-75 minutes in the PAR; column cycles of ≤100 in the NOR and ≤100 in the PAR; an elution hold time (end of filtration through start of low pH acidification) of ≤7 days in the NOR and ≤10 days in the PAR; a step yield of ≥70%; an eluate pre-filtration bioburden of <50 CFU/10 mL; an eluate post-filtration bioburden of <3 CFU/10 mL; and/or an eluate post-filtration endotoxin concentration of <5 EU/mL.

Low pH Viral Inactivation Step

Source materials (e.g., cell lines, cellular debris) and viruses introduced during antibody production can present viral contamination risks, which can have potential consequences with serious clinical and economic implications. Direct exposure of process intermediates to pH extremes has been used for viral clearance in biopharmaceutical manufacturing. Studies have proven that low pH treatment (e.g., pH 3.0-3.75) of monoclonal antibodies following affinity chromatography, for example, is effective against enveloped viruses (Brorson, K. et al., *Biotechnol. Bioeng.*, 82:321-9, 2003). In general, exposure to pH extremes during manufacture of monoclonal antibodies can provide effective and robust viral reduction (e.g., >4.0 log 10 reduction). Accordingly, the methods described herein can also include a low pH viral inactivation step.

In one embodiment, the method includes subjecting the material from the previous step (e.g., an eluted pool from the Protein A affinity chromatography purification; a "pool" is the combined fractions from a chromatography step, e.g., the fractions that contain the elution fractions) to low pH conditions. In one embodiment, the low pH is a pH of 3.0, 3.1, 3.2, 3.25, 3.3, 3.4, 3.5, 3.6, 3.7 or 3.75). In another embodiment, the low pH is within a range of 3.0-3.75. In another embodiment, the low pH is within a range of 3.60 to 3.75. In another embodiment, the method includes treating the material from the previous step with acetic acid. In another embodiment, the method includes increasing the pH after a low pH has been confirmed and then filtering out neutralized viral inactivated material.

In another embodiment, the low pH viral inactivation step comprises (a) treating material from the previous step (e.g., an eluted pool from the Protein A affinity chromatography purification) with acetic acid (e.g., 1 M acetic acid at a pH range of 3.60-3.70), (b) transferring it to a second vessel and incubating it at ambient temperature (e.g., 20° C., 21° C., 23° C., 24° C. or 25° C.) for a minimum of 60 minutes (e.g., at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 minutes) without mixing and confirming the pH range to be within 3.60 to 3.75; (c) increasing to pH 5.0 (e.g., using 1 M Tris) and incubating at ambient temperature for a minimum of 60 minutes (e.g., at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 minutes) without mixing; (d) pre-filtering (e.g., 0.5/0.2 μm filter) neutralized viral inactivated material, and storing the filtered product.

In another embodiment, the processing conditions for the low pH viral inactivation step include one or more (e.g., one, two, three, four, five, six, seven, eight, nine or ten) of the following: an acidification pH immediately after titration of 3.60-3.70 in the NOR and 3.55-3.80 in the PAR; an acidification pH immediately after hold time of 3.60-3.75 in the NOR and 3.55-3.80 in the PAR; a hold time at low pH of 60-120 minutes in the NOR and ≥60-360 minutes in the PAR; a hold time at neutralized pH prior to 0.5/0.2 μm filtration of 60-120 minutes in the NOR and ≥60 minutes in the PAR; a filtered neutralized product hold time (end of filtration through end of CEX load) of ≤7 days in the NOR and ≤7 days in the PAR; a yield of ≥90%; a neutralized pre-filtration pool bioburden of <50 CFU/10 mL; a neutralized post-filtration pool bioburden of <3 CFU/10 mL; and/or a neutralized post-filtration pool endotoxin concentration of <5 EU/mL.

Cation Exchange Chromatography (CEX)

The methods described herein can also include a CEX step. CEX is a form of ion exchange chromatography (IEX), which is used to separate molecules based on their net surface charge. CEX, more specifically, uses a resin modified with negatively charged functional groups. They can be strong acidic ligands such as sulphopropyl, sulfoethyl and sulfoisobutyl groups or weak acidic ligand, such as carboxyl group. CEX has been applied for purification processes for many monoclonal antibodies with pI values ranging from neutral to basic. Most humanized IgG1 and IgG2 subclasses are perfect candidates for CEX, in which the antibody is bound to the resin during the loading step and eluted through either increasing conductivity or increasing pH in the elution buffer. The most negatively charged, process-related impurities such as DNA, some host cell protein, leached Protein A and endotoxin are removed in the load and wash fractions. CEX can provide separation power to reduce antibody variants from the target antibody product such as deamidated products, oxidized species and N-terminal truncated forms, as well as high molecular weight species.

A "cation exchange resin" or "CEX resin" refers to a solid phase that is negatively charged and has free cations for exchange with cations in an aqueous solution passed over or through the solid phase. Any negatively charged ligand attached to the solid phase suitable to form the CEX resin can be used, e.g., a carboxylate, sulfonate and others. Commercially available CEX resins include, but are not limited to, for example, those having a sulfonate based group (e.g., MonoS, MiniS, Source 15S and 30S, SP Sepharose® Fast Flow, SP Sepharose® High Performance from GE Healthcare, Toyopearl® SP-650S and SP-650M from Tosoh, Macro-Prep® High S from BioRad, Ceramic HyperD® S, Trisacryl M and LS SP and Spherodex LS SP from Pall Technologies); a sulfoethyl based group (e.g., Fractogel® SE, from EMD, Poros® S-10 and S-20 from Applied Biosystems); a sulphopropyl based group (e.g., TSK Gel SP 5PW and SP-5PW-HR from Tosoh, Poros® HS-20 and HS 50 from Applied Biosystems); a sulfoisobutyl based group (e.g., Fractogel® EMD SO.sub.3.sup.—from EMD); a sulfoxyethyl based group (e.g., SE52, SE53 and Express-Ion S from Whatman), a carboxymethyl based group (e.g., CM Sepharose® Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrex® Cellufine® C500 and C200 from Millipore, CM52, CM32, CM23 and Express-Ion C from Whatman, Toyopearl® CM-650S, CM-650M and CM-650C from Tosoh); sulfonic and carboxylic acid based groups (e.g., BAKERBOND® Carboxy-Sulfon from J. T. Baker); a carboxylic acid based group (e.g., WP CBX from J. T. Baker, DOWEX® MAC-3 from Dow Liquid Separations, Amberlite Weak Cation Exchangers, DOWEX® Weak Cation Exchanger, and Diaion® Weak Cation Exchangers from Sigma-Aldrich and Fractogel® EMD COO from EMD); a sulfonic acid based group (e.g., Hydrocell SP from Biochrom Labs Inc., DOWEX® Fine Mesh Strong Acid Cation Resin from Dow Liquid Separations, UNOsphere S, WP Sulfonic from J. T. Baker, Sartobind® S membrane from Sartorius, Amberlite Strong Cation Exchangers, DOWEX® Strong Cation and Diaion® Strong Cation Exchanger from Sigma-Aldrich); and a orthophosphate based group (e.g., P11 from Whatman). In a particular embodiment POROS® HS50 cation exchange column is used.

In one embodiment, material from a previous step (e.g., neutralized filtrate from the low pH viral inactivation step) is loaded onto a cation exchange column (e.g., a POROS® HS50 cation exchange column), for example, through a 0.5/0.2 μm filter. In one embodiment, the CEX step includes the use of one or more (e.g., one, two, three, four, five, six, seven, eight or nine) buffers, including, but not limited to: (a) sodium acetate, (b) sodium chloride, (c) sodium hydroxide, (d) sodium acetate and sodium chloride, and (e) sodium acetate, sodium chloride, and arginine hydrochloride. In another embodiment, the CEX buffer comprises 50 mM sodium acetate (pH 5.0) for equilibration and post-load wash 1. In another embodiment, the CEX buffer comprises 50 mM sodium acetate (pH 4.9) and 60 mM sodium chloride for post-load wash 2. In another embodiment, the CEX buffer comprises 50 mM sodium acetate (pH 5.0), 90 mM arginine hydrochloride, and 30 mM sodium chloride for elution. In another embodiment, the CEX buffer comprises 2.0 M sodium chloride for stripping. In another embodiment, the CEX buffer comprises 1.0 N sodium hydroxide for sanitization. In another embodiment, the CEX buffer comprises 0.1 N sodium hydroxide for storage.

In another embodiment, the processing conditions for the CEX include one or more (e.g., one, two, three, four, five, six, seven, eight, nine, ten or 11) of the following: a load capacity of 22-45 g/L in the NOR and 15-50 g/L in the PAR; a temperature of 15-25° C. in the NOR and 13-27° C. in the PAR; an elution buffer pH of 4.90-5.10 in the NOR and 4.90-5.10 in the PAR; an elution buffer conductivity of 11.1-13.6 mS/cm in the NOR and 11.1-13.6 mS/cm in the PAR; an elution flow rate of 150-300 cm/hr in the NOR and 120-330 cm/hr in the PAR; an eluate hold time (start of eluate collection through end of AEX load adjustment) of ≤7 days in the NOR and ≤10 days in the PAR; column cycles of ≤100 in the NOR and ≤100 in the PAR; an eluate post-filtration bioburden of <3 CFU/10 mL; an eluate post-filtration endotoxin of <5 EU/mL; a step yield of ≥58%; and/or an elution volume of 2.3-5.0 column volumes.

Anion Exchange Chromatography (AEX)

The methods described herein can also include an AEX step. AEX uses a positively charged group (weakly basic such as diethylamino ethyl, DEAE or dimethylamino ethyl, DMAE; or strongly basic such as quaternary amino ethyl, Q or trimethylammonium ethyl, TMAE or quaternary aminoethyl, QAE) immobilized to the resin. It is a powerful tool to remove process-related impurities such as host cell proteins, DNA, endotoxins and leached Protein A, product-related impurities such as dimer/aggregate, endogenous retrovirus and adventitious viruses such as parvovirus, pseudorabies virus (Curtis, S. et al., Biotechnol. Bioeng., 84:179-86, 2003; Norling, L. et al., J. Chromatogr. A, 1069:79-89, 2005; and Zhou, J. et al., J. Chromatogr. A, 1134:66-73, 2006). AEX can be used either in flow-through mode or in bind and elute mode, depending on the pI of the antibody and impurities to be removed. For antibodies having a pI above 7.5, which includes most humanized IgG1 and IgG2 antibodies, flow-through mode can be a better choice to remove impurities. In flow-through mode, the impurities bind to the resin and the product of interest flows through. The column loading capacity can be quite high since the binding sites on the resin are occupied only by the impurities. For antibodies having a pI in the acidic to neutral range, which includes most humanized IgG4 antibodies, bind and elute modes can be used to remove process-related and product-related impurities from the product of interest.

AEX in flow-through mode has been widely used as a polishing step in monoclonal antibody purification processes designed with two or three unit operations to remove residual impurities such as host cell protein, DNA, leached Protein A and a variety of viruses. The operating pH is normally 8 to 8.2, with a conductivity of up to 10 mS/cm in the product load and equilibration and wash buffers. Conditions are chosen such that the product does not bind to the column, while acidic impurities such as nucleic acid and host cell proteins do. Depending on the resin, loading conditions and charge variant profile of the antibody product, the amount of product loaded can reach one hundred grams per liter of resin without compromising product quality (Fahrner, R. et al., Biotechnol. Genet. Eng. Rev., 18:301-27, 2001). In general, the amount of product loaded in a flow-through mode depends on the impurity species and levels to be removed. A lower level of impurity in the product results in a higher amount of product loaded.

Exemplary anion exchange resins include, but are not limited to, quaternary amine resins or "Q-resins" (e.g., Q-Sepharose®, QAE Sephadex®); diethylaminoethane (DEAE) resins (e.g., DEAE-Trisacryl®, DEAE Sepharose®, benzoylated naphthoylated DEAE, diethylaminoethyl Sephacel®); Amberjet® resins; Amberlyst® resins; Amberlite® resins (e.g., Amberlite® IRA-67, Amberlite® strongly basic, Amberlite® weakly basic), cholestyramine resin, ProPac® resins (e.g., ProPac® SAX-10, ProPac® WAX-10, ProPac® WCX-10); TSK-GEL resins (e.g., TSKgel® DEAE-NPR; TSKgel® DEAE-5PW); and Acclaim® resins. In one embodiment, the AEX column is a POROS® HQ50 AEX column operated, for example, in flow-through mode.

In one embodiment, material from a previous step (e.g., an eluted pool from the CEX step) is pH adjusted prior to loading on to an AEX column. In another embodiment, material from the previous step (e.g., an eluted pool from the CEX step) is pH adjusted using Tris, arginine and WFI. In another embodiment, material from the previous step (e.g., an eluted pool from the CEX step) is adjusted to a pH of approximately 8.0. In another embodiment, material from the previous step (e.g., an eluted pool from the CEX step) is adjusted to a conductivity of 8.5 mS/cm. In another embodiment, material from the previous step (e.g., an eluted pool from the CEX step) is adjusted to a pH of 8.00 and a conductivity of 8.5 mS/cm with 100 mM Tris (pH 9.0), 180 mM arginine and WFI. In another embodiment, material from the previous step (e.g., an eluted pool from the CEX step) is loaded on to an AEX column within 24 hours (e.g., within 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours or 23 hours) of the adjustment. In another embodiment, material from the previous step (e.g., an eluted pool from the CEX step) is loaded on to an AEX column through a filter (e.g., 0.5/0.2 μm filter) and the resulting product is chased (e.g., flushed) from the AEX column, e.g., using buffer filtered through an filter (e.g., 0.5/0.2 μm filter) into a filtrate vessel.

In another embodiment, the AEX step includes the use of one or more (e.g., one, two, three, four, five, six, seven, eight or nine) buffers, including, but not limited to: (a) Tris and arginine, (b) WFI, (c) sodium chloride, (d) Tris and sodium chloride, and (e) sodium hydroxide. In another embodiment, the AEX step includes the use of 100 mM Tris (pH 9.0) and 180 mM arginine for load pH adjustment. In another embodiment, the AEX step includes the use of WFI for load conductivity adjustment and flush. In another embodiment, the AEX step includes the use of 2 M sodium chloride for conditioning. In another embodiment, the AEX step includes the use of 20 mM Tris (pH 7.6) and 65 mM sodium chloride for equilibration and post-load chase. In another embodiment, the AEX step includes the use of 2 M sodium chloride for post-load elution stripping. In another embodiment, the AEX step includes the use of 1.0 N sodium hydroxide for sanitization. In another embodiment, the AEX step includes the use of 0.1 N sodium hydroxide for storage.

In another embodiment, the processing conditions for the AEX include one or more (e.g., one, two, three, four, five, six, seven, eight, nine, ten or 11) of the following: a load pH of 7.90-8.10 in the NOR and 7.80-8.20 in the PAR; a load conductivity of 8.0-9.0 mS/cm in the NOR and 7.0-10.0 mS/cm in the PAR; a load capacity pH of 25-90 g/L in the NOR and 25-100 g/L in the PAR; a hold time (AEX load adjustment through start of AEX Load) of ≤1 day in the NOR and ≤4 days in the PAR; a product hold time (end of AEX load adjustment through end of UF/DF) of ≤4 days in the NOR and ≤6 days in the PAR; column cycles of ≤100 in the NOR and ≤100 in the PAR; an eluate bioburden (post-filtration) of <3 CFU/10 mL; and/or an eluate endotoxin concentration (post-filtration) of <5 EU/mL; and a yield of ≥67%.

Viral Filtration

Many purification processes for biopharmaceuticals use virus-reduction filtration as an part of an overall strategy for viral clearance (Caballero, S. et al., *Biologicals*, 42:79-85, 2014; and Marques, B. et al., *Biotechnol. Prog.*, 25:483-91, 2009). Virus-reduction filters can provide robust and effective removal of large and medium sized viruses. Such filters also can effectively remove very small viruses (e.g., parvoviruses) with pore sizes ≤20 nm.

Typical virus filtration membranes are made from hydrophilic polyethersulfone (PES), hydrophilic polyvinylidene (PVDF) and regenerated cellulose. According to the size distribution of viruses that are removed, virus filters can be categorized into retrovirus filters and parvovirus filters. Exemplary virus filters include, but are not limited to, Planova® 15N, Planova® 20N, Planova® 35N, Planova BioEX®, Viresolve® NFP, Viresolve® NFR, Viresolve® Pro, Ultipor® DV 20, Ultipor® DV 50, and Virosart® CPV. Parvoviruses have a diameter of 18-26 nm, and a typical mAb has a hydrodynamic diameter of 8 12 nm.

The methods described herein can also include a filtration step to remove viruses or virus-like particles. In one embodiment, the filters are flushed prior to use (e.g., using WFI and buffer). In another embodiment, flow-through filtrate from the AEX, for example, is filtered through a Viresolve® Pro Shield H pre-filter (e.g., 0.5/0.2 μm), followed by filtration through a Viresolve® Pro filter (e.g., 20 nm).

In another embodiment, the filtration step to remove viruses or virus-like particles includes the use of one or more (e.g., one, two, three, four, five, six, seven, eight or nine) buffers, including, but not limited to: (a) Tris and sodium chloride and (b) WFI. In another embodiment, the filtration step to remove viruses or virus-like particles includes the use WFI as a pre-use flush. In another embodiment, the filtration step to remove viruses or virus-like particles includes the use of 20 mM Tris (pH 7.6) and 65 mM sodium chloride for equilibration and post-loading chase.

In another embodiment, the filtration step to remove viruses or virus-like particles includes one or more (e.g., one, two, three, four, five, six, seven, eight, nine, ten, eleven or twelve) of the following: a VIRESOLVE® Pro filter differential pressure during load and chase of 21-32 psid in the NOR and 21-35 psid in the PAR; a Total Pause Time during load and chase of 0 minutes in the NOR and ≤120 minutes in the PAR; a chase volume of ≤15 L/m² in the NOR and ≤20 L/m² in the PAR; pass a post-use integrity test; a load concentration of 3.0-6.0 g/L in the NOR and ≤6.7 g/L in the PAR; a shield H pre-filter load of ≤700 L/m² in the NOR and ≤1200 L/m² in the PAR; a VIRESOLVE® Pro filter load of ≤700 L/m² in the NOR and ≤700 L/m² in the PAR; a product hold time (end of AEX load adjustment through end of UF/DF) of ≤4 days in the NOR and ≤6 days in the PAR; a bioburden (pre-filtration viral filter load) of <3 CFU/10 mL; an endotoxin concentration (viral filtrate) of <2 EU/mL; pass a pre-use integrity test; and/or a processing time (start of load to end of load) of ≤12 hours; and/or a step yield of ≥90%.

Concentration and Diafiltration

The methods described herein can also include a concentration and diafiltration step. In one embodiment, material from the previous step (e.g., a pool from the virus filtration step) is ultrafiltrated and concentrated.

Diafiltration is a technique that uses ultrafiltration membranes to completely remove, replace, or lower the concentration of salts or solvents from solutions containing proteins, peptides, nucleic acids, and other biomolecules. The process selectively utilizes permeable (porous) membrane filters to separate the components of solutions and suspensions based on their molecular size. An ultrafiltration membrane retains molecules that are larger than the pores of the membrane while smaller molecules such as salts, solvents and water, which are 100% permeable, freely pass through the membrane.

Ultrafiltration is a pressure-driven membrane process that is widely used for protein concentration and buffer exchange. Ultrafiltration is a size-based separation where species larger than the membrane pores are retained and smaller species pass through freely. Separation is achieved through differences in the filtration rates of different components across the membrane under a given pressure driving force (van Reis, R. & Zydney, A. Protein ultrafiltration. In: Flickinger M C, Drew S W, editors. Encyclopedia of Bioprocess Technology-Fermentation, Biocatalysis and Bioseparation. John Wiley & Sons; 1999. pp. 2197-2214). Buffer exchange is achieved using a diafiltration mode in which buffer of the final desired composition is added to the retentate system at the same rate in which filtrate is removed, thus maintaining a constant retentate volume.

In one embodiment, material from the previous step (e.g., a pool from the virus filtration step) is diafiltered. In another embodiment, the resulting concentrated product is measured and diluted (e.g., to 10.0 g/L). In another embodiment, material from the previous step (e.g., a pool from the virus filtration step) is (a) ultrafiltrated and concentrated, e.g., to 55 g/L using a 30 kD molecular weight cut-off (MWCO) UF membrane, (b) diafiltered (e.g., with 6× diafiltration volumes) into a formulation buffer and the resulting concentrated product is measured and diluted (e.g., to 10.0 g/L). In another embodiment, the formulation buffer comprises 10 mM sodium phosphate (pH 7.0) and 150 mM sodium chloride. In another embodiment, the diluted product is filtered (e.g., through a 0.5/0.2 μm filter) and Polysorbate 80 is added to a diluted product pool to achieve a final concentration of 0.02% (w/v) Polysorbate 80.

In another embodiment, the concentration and diafiltration step includes the use of one or more (e.g., one, two, three, four, five, six, seven, eight or nine) buffers, including, but not limited to: (a) WFI, (b) sodium hydroxide, (c) sodium phosphate and 150 mM sodium chloride, and (d)

polysorbate 80. In another embodiment, the concentration and diafiltration step includes the use of WFI as a flush. In another embodiment, the concentration and diafiltration step includes the use of 0.5 M sodium hydroxide for sanitization. In another embodiment, the concentration and diafiltration step includes the use of 10 mM sodium phosphate (pH 7.0) and 150 mM sodium chloride for equilibration, diafiltration, chase and/or pool dilution. In another embodiment, the concentration and diafiltration step includes the use of 0.1 M sodium hydroxide for storage. In another embodiment, the concentration and diafiltration step includes the use of 10% (w/v) Polysorbate 80 for excipient.

In another embodiment, the concentration and diafiltration step includes one or more (e.g., one, two, three, four, five, six, seven, eight, nine, ten, eleven, twelve, thirteen, fourteen, fifteen, sixteen, seventeen, eighteen or nineteen) of the following: a dilution of within 1% of calculated volume in the NOR and within 3% of calculated volume in the PAR; 10% (w/v) Polysorbate 80 is 0.19-0.21% (w/v) of diluted UF/DF product in the NOR and 0.17-0.23% (w/v) of diluted UF/DF product in the PAR; an un-formulated drug substance pH of 6.5-7.5; a diluted UF/DF product concentration of 9.0-11.0 mg/mL; passing a pre-use integrity test; a membrane loading of 100-500 g/m$^2$ in the NOR and within 50-600 g/m$^2$ in the PAR; a feed flux of 240-420 LMH in the NOR and within 180-440 LMH in the PAR; a transmembrane pressure of 10-30 psi in the NOR and within 8-35 psi in the PAR; a pressure of 15-25° C. in the NOR and within 12-30° C. in the PAR; a fed batch ratio of 1-3 in the NOR and within 1-5 in the PAR; a concentration at end of ultrafiltration target of 13-17 g/L in the NOR and within 12-20 g/L in the PAR; a diavolume of 5.5-7.0 in the NOR and within 4.5-7.0 in the PAR; an unformulated UF/DF retentate hold of ≤4 days in the NOR and within ≤6 days in the PAR; a product hold (diluted UF/DF product) of ≤7 days in the NOR and within ≤14 days in the PAR; a step yield of ≥90%; a processing time (start of initial concentration through end of diafiltration) of ≤11.1 hours; a post-use normalized water permeability (NWP) flux of 75-125% of initial; a diluted UF/DF pre-filtration pool bioburden of <10 CFU/10 mL; and/or a diluted UF/DF post-filtration pool bioburden of <3 CFU/10 mL; and/or a diluted UF/DF post-filtration pool endotoxin concentration of <2 EU/mL.

In another embodiment, the concentration and/or diafiltration steps include one or more (e.g., one, two, three, four, five, six, seven, eight, nine, ten, eleven, twelve, thirteen, fourteen, fifteen, sixteen, seventeen, eighteen, nineteen, or twenty) of the following: an initial concentration target of 40-60 g/L; a final concentration target (140-160 g/L) (includes 1.07 recovery factor); a diavolume of 4.5-7.5, with a target of 6.0; an undiluted ultrafiltrated/diafiltrated product hold of ≤24 hours); a diluted ultrafiltrated/diafiltrated product hold of ≤24 hours); use of a Millipore Pellicon 3 Ultracel C screen 30 kDa MWCO filter; a flush WFI≥20 L/m$^2$; an equilibrium of 50 mM NaPO$_4$ (pH 7.4), 25 mM L-Arg (≥20 L/m$^2$); a membrane load of ≤600 L/m$^2$; a target feed flow rate for all product steps of 360 LMH; a target transmembrane pressure for all product steps of 15 psi; a feed pressure or ≤50 psi (can be increased); a diafiltration buffer that is the same as equilibrium; a final concentration that can be controlled by feed pressure (not TMP or Feed Flow Rate); a temperature of 15-35° C.; a recovery with ≤1× system hold-up volume (calculation required per CSD); a dilution to target 120 g/L with DF/equilibrium buffer; 0.1919-0.2393 kg/kg addition of excipient addition buffer (EAB—50 mM NaPO$_4$ (pH 7.4), 25 mM L-Arg, 30% Sucrose 0.30% (w/v), PS 80) to 120 g/L UF/DF product for final formulation; membrane re-use up to 20 cycles; sanitization with 0.5 M NaOH, storage with 0.1 M NaOH; a yield of >60% (expected over 90%); express SHC filterability 120 g/L UF/DF product: ≤40 L/m$^2$; and express SHC filterability BDS of ≤3045 L/m$^2$.

Bulk Filtration

The methods described herein can also include a bulk filtration step. In one embodiment, material from a previous step (e.g., from the ultrafiltration and diafiltration step) is bulk filtered.

Anti-C5 Antibodies

The term "antibody" describes a polypeptide comprising at least one antigen binding site (e.g., VH/VL region or Fv, or CDR). Antibodies include known forms of antibodies, including, but not limited to, monoclonal antibodies (including full length monoclonal antibodies), polyclonal antibodies, monospecific antibodies, multispecific antibodies (e.g., bispecific antibodies), immunoadhesins, antibody-immunoadhesin chimeras, humanized, human, chimeric, single-chain, camelid, synthetic, recombinant, hybrid, mutated, grafted, or in vitro generated antibodies. The antibody can be a full-length antibody or an antibody fragment. The antibody can be a human antibody, a humanized antibody, a bispecific antibody, or a chimeric antibody. The antibody also can be a Fab, Fab'2, ScFv, SMIP, Affibody®, nanobody, or a single domain antibody. The antibody also can be of any of the following isotypes: IgG1, IgG2, IgG3, IgG4, IgM, IgA1, IgA2, IgAsec, IgD, IgE or chimeric versions thereof. The antibody can be a naturally occurring antibody or an antibody that has been altered by a protein engineering technique (e.g., by mutation, deletion, substitution, conjugation to a non-antibody moiety). An antibody can include, for example, one or more variant amino acids (compared to a naturally occurring antibody), which changes a property (e.g., a functional property) of the antibody. Numerous such alterations are known in the art that affect, e.g., half-life, effector function, and/or immune responses to the antibody in a patient. The term antibody also includes artificial or engineered polypeptide constructs that comprise at least one antibody-derived antigen binding site.

An exemplary anti-C5 antibody is ravulizumab comprising heavy and light chains having the sequences shown in SEQ ID NOs:14 and 11, respectively, or antigen binding fragments and variants thereof. Ravulizumab is described in PCT/US2015/019225 and U.S. Pat. No. 9,079,949, the teachings of which are hereby incorporated by reference. Ravulizumab selectively binds to human complement protein C5, inhibiting its cleavage to C5a and C5b during complement activation. This inhibition prevents the release of the pro-inflammatory mediator C5a and the formation of the cytolytic pore-forming membrane attack complex (MAC) C5b-9 while preserving the proximal or early components of complement activation (e.g., C3 and C3b) essential for the opsonization of microorganisms and clearance of immune complexes.

In other embodiments, the antibody comprises the heavy and light chain CDRs or variable regions of ravulizumab. Accordingly, in one embodiment, the antibody comprises the CDR1, CDR2 and CDR3 domains of the VH region of ravulizumab having the sequence set forth in SEQ ID NO:12, and the CDR1, CDR2 and CDR3 domains of the VL region of ravulizumab having the sequence set forth in SEQ ID NO:8. In another embodiment, the antibody comprises heavy chain CDR1, CDR2 and CDR3 domains having the sequences set forth in SEQ ID NOs:19, 18 and 3, respectively, and light chain CDR1, CDR2 and CDR3 domains having the sequences set forth in SEQ ID NOs:4, 5 and 6, respectively. In another embodiment, the antibody comprises VH and VL regions having the amino acid sequences set forth in SEQ ID NO:12 and SEQ ID NO:8, respectively.

In other embodiments, the anti-C5 antibody produced according to the methods disclosed herein is formulated in a 10 mg/mL solution. In another embodiment, the anti-C5 antibody is formulated in a sterile, preservative-free 10 mg/mL solution e.g., which is suitable for IV administration. In another embodiment, the anti-C5 antibody is supplied in 20 mL single-use vials. In another embodiment, each vial contains 150 mg of ravulizumab in 10 mM sodium phosphate, 150 mM sodium chloride, 0.02% polysorbate 80, and water for injection at a pH of 7.0.

In other embodiments, the anti-C5 antibody produced according to the methods disclosed herein is formulated in a 100 mg/mL solution. In another embodiment, the anti-C5 antibody is formulated in a sterile, preservative-free 100 mg/mL solution e.g., which is suitable for subcutaneous administration. In another embodiment, the anti-C5 antibody is supplied in 2 mL single-use vials. In another embodiment, each vial contains 100 mg/mL of ravulizumab in 50 mM sodium phosphate, 25 mM arginine, 5% sucrose, and 0.05% polysorbate 80, and water for injection at a pH of 7.4.

The exact boundaries of CDRs have been defined differently according to different methods. In some embodiments, the positions of the CDRs or framework regions within a light or heavy chain variable domain can be as defined by Kabat et al. [(1991) "Sequences of Proteins of Immunological Interest." NIH Publication No. 91-3242, U.S. Department of Health and Human Services, Bethesda, Md.]. In such cases, the CDRs can be referred to as "Kabat CDRs" (e.g., "Kabat LCDR2" or "Kabat HCDR1"). In some embodiments, the positions of the CDRs of a light or heavy chain variable region can be as defined by Chothia, C. et al. (*Nature*, 342:877-83, 1989). Accordingly, these regions can be referred to as "Chothia CDRs" (e.g., "Chothia LCDR2" or "Chothia HCDR3"). In some embodiments, the positions of the CDRs of the light and heavy chain variable regions can be as defined by a Kabat-Chothia combined definition. In such embodiments, these regions can be referred to as "combined Kabat-Chothia CDRs" (Thomas, T. et al., *Mol. Immunol.*, 33:1389-401, 1996) exemplifies the identification of CDR boundaries according to Kabat and Chothia definitions.

In some embodiments, an anti-C5 antibody described herein comprises a heavy chain CDR1 comprising or consisting of GHIFSNYWIQ (SEQ ID NO:19). In some embodiments, an anti-C5 antibody described herein comprises a heavy chain CDR2 comprising or consisting of EILPGSGHTEYTENFKD (SEQ ID NO:18). In some embodiments, an anti-C5 antibody described herein comprises a heavy chain variable region comprising (SEQ ID NO: 12)
QVQLVQSGAEVKKPGASVKVSCKASGHIFSNYWIQWVRQAPGQGLEWMGE

ILPGSGHTEYTENFKDRVTMTRDTSTSTVYMELSSLRSEDTAVYYCARYF

FGSSPNWYFDVWGQGTLVTVSS.

In some embodiments, an anti-C5 antibody described herein comprises a light chain variable region comprising (SEQ ID NO: 8)
DIQMTQSPSSLSASVGDRVTITCGASENIYGALNWYQQKPGKAPKLLIYG

ATNLADGVPSRFSGSGSGTDFTLTISSLQPEDFATYYCQNVLNTPLTFGQ

GTKVEIK.

Another exemplary anti-C5 antibody is antibody BNJ421 comprising heavy and light chains having the sequences shown in SEQ ID NOs:20 and 11, respectively, or antigen binding fragments and variants thereof. BNJ421 is described in PCT/US2015/019225 and U.S. Pat. No. 9,079,949, the teachings of which are hereby incorporated by reference. In other embodiments, the antibody comprises the heavy and light chain CDRs or variable regions of BNJ421. Accordingly, in one embodiment, the antibody comprises the CDR1, CDR2 and CDR3 domains of the VH region of BNJ421 having the sequence set forth in SEQ ID NO:12, and the CDR1, CDR2 and CDR3 domains of the VL region of BNJ421 having the sequence set forth in SEQ ID NO:8. In another embodiment, the antibody comprises heavy chain CDR1, CDR2 and CDR3 domains having the sequences set forth in SEQ ID NOs:19, 18 and 3, respectively, and light chain CDR1, CDR2 and CDR3 domains having the sequences set forth in SEQ ID NOs:4, 5 and 6, respectively. In another embodiment, the antibody comprises VH and VL regions having the amino acid sequences set forth in SEQ ID NO:12 and SEQ ID NO:8, respectively.

Another exemplary anti-C5 antibody is the 7086 antibody described in U.S. Pat. Nos. 8,241,628 and 8,883,158. In one embodiment, the antibody comprises the heavy and light chain CDRs or variable regions of the 7086 antibody. In another embodiment, the antibody or antigen binding fragment thereof comprises heavy chain CDR1, CDR2 and CDR3 domains having the sequences set forth in SEQ ID NOs: 21, 22 and 23, respectively, and light chain CDR1, CDR2 and CDR3 domains having the sequences set forth in SEQ ID NOs: 24, 25 and 26, respectively. In another embodiment, the antibody or antigen binding fragment thereof comprises the VH region of the 7086 antibody having the sequence set forth in SEQ ID NO:27, and the VL region of the 7086 antibody having the sequence set forth in SEQ ID NO:28.

Another exemplary anti-C5 antibody is the 8110 antibody also described in U.S. Pat. Nos. 8,241,628 and 8,883,158. In one embodiment, the antibody comprises the heavy and light chain CDRs or variable regions of the 8110 antibody. In another embodiment, the antibody, or antigen binding fragment thereof, comprises heavy chain CDR1, CDR2 and CDR3 domains having the sequences set forth in SEQ ID NOs: 29, 30 and 31, respectively, and light chain CDR1, CDR2 and CDR3 domains having the sequences set forth in SEQ ID NOs: 32, 33 and 34, respectively. In another embodiment, the antibody comprises the VH region of the 8110 antibody having the sequence set forth in SEQ ID NO:35, and the VL region of the 8110 antibody having the sequence set forth in SEQ ID NO:36.

Another exemplary anti-C5 antibody is the 305LO5 antibody described in US2016/0176954A1. In one embodiment, the antibody comprises the heavy and light chain CDRs or variable regions of the 305LO5 antibody. In another embodiment, the antibody, or antigen binding fragment thereof, comprises heavy chain CDR1, CDR2 and CDR3 domains having the sequences set forth in SEQ ID NOs:37, 38 and 39, respectively, and light chain CDR1, CDR2 and CDR3 domains having the sequences set forth in SEQ ID NOs:40, 41 and 42, respectively. In another embodiment, the antibody comprises the VH region of the 305LO5 antibody having the sequence set forth in SEQ ID NO:43, and the VL region of the 305LO5 antibody having the sequence set forth in SEQ ID NO:44.

Another exemplary anti-C5 antibody is the SKY59 antibody (Fukuzawa, T. et al., *Sci. Rep.,* 7:1080, 2017). In one embodiment, the antibody comprises the heavy and light chain CDRs or variable regions of the SKY59 antibody. In another embodiment, the antibody, or antigen binding fragment thereof, comprises a heavy chain comprising SEQ ID NO:45 and a light chain comprising SEQ ID NO:46.

Another exemplary anti-C5 antibody is the REGN3918 antibody (also known as H4H12166PP) described in US20170355757. In one embodiment, the antibody comprises a heavy chain variable region comprising SEQ ID NO:47 and a light chain variable region comprising SEQ ID NO:48. In another embodiment, the antibody comprises a heavy chain comprising SEQ ID NO:49 and a light chain comprising SEQ ID NO:50.

An anti-C5 antibody described herein can, in some embodiments, comprise a variant human Fc constant region that binds to human neonatal Fc receptor (FcRn) with greater affinity than that of the native human Fc constant region from which the variant human Fc constant region was derived. The Fc constant region can comprise, for example, one or more (e.g., two, three, four, five, six, seven, or eight or more) amino acid substitutions relative to the native human Fc constant region from which the variant human Fc constant region was derived. The substitutions, for example, can increase the binding affinity of an IgG antibody containing the variant Fc constant region to FcRn at pH 6.0, while maintaining the pH dependence of the interaction. Methods for testing whether one or more substitutions in the Fc constant region of an antibody increase the affinity of the Fc constant region for FcRn at pH 6.0 (while maintaining pH dependence of the interaction) are known in the art and exemplified in the working examples (PCT/US2015/019225 and U.S. Pat. No. 9,079,949 the disclosures of each of which are incorporated herein by reference in their entirety).

Substitutions that enhance the binding affinity of an antibody Fc constant region for FcRn are known in the art and include, e.g., (1) the M252Y/S254T/T256E triple substitution (Dall'Acqua, W. et al., *J. Biol. Chem.,* 281: 23514-24, 2006); (2) the M428L or T250Q/M428L substitutions (Hinton, P. et al., *J. Biol. Chem.,* 279:6213-6, 2004; Hinton, P. et al., *J. Immunol.,* 176:346-56, 2006); and (3) the N434A or T307/E380A/N434A substitutions (Petkova, S. et al., *Int. Immunol.,* 18:1759-69, 2006). Additional substitution pairings, e.g., P257I/Q311I, P257I/N434H, and D376V/N434H, have also been described (Datta-Mannan, A. et al., *J. Biol. Chem.,* 282:1709-17, 2007). The entire teachings of each of the cited references are hereby incorporated by reference.

In some embodiments, the variant constant region has a substitution at EU amino acid residue 255 for valine. In some embodiments, the variant constant region has a substitution at EU amino acid residue 309 for asparagine. In some embodiments, the variant constant region has a substitution at EU amino acid residue 312 for isoleucine. In some embodiments, the variant constant region has a substitution at EU amino acid residue 386.

In some embodiments, the variant Fc constant region comprises no more than 30 (e.g., no more than 29, 28, 27, 26, 25, 24, 23, 22, 21, 20, 19, 18, 17, 16, 15, 14, 13, 12, 11, 10, nine, eight, seven, six, five, four, three or two) amino acid substitutions, insertions or deletions relative to the native constant region from which it was derived. In some embodiments, the variant Fc constant region comprises one or more amino acid substitutions selected from the group consisting of: M252Y, S254T, T256E, N434S, M428L, V259I, T250I and V308F. In some embodiments, the variant human Fc constant region comprises a methionine at position 428 and an asparagine at position 434, each in EU numbering. In some embodiments, the variant Fc constant region comprises a 428L/434S double substitution as described in, e.g., U.S. Pat. No. 8,088,376 the disclosure of which is incorporated herein by reference in its entirety.

In some embodiments the precise location of these mutations may be shifted from the native human Fc constant region position due to antibody engineering. The 428L/434S double substitution when used in a IgG2/4 chimeric Fc, for example, may correspond to 429L and 435S as in the M429L and N435S variants found in ravulizumab and described in U.S. Pat. No. 9,079,949 the disclosure of which is incorporated herein by reference in its entirety.

In some embodiments, the variant constant region comprises a substitution at amino acid position 237, 238, 239, 248, 250, 252, 254, 255, 256, 257, 258, 265, 270, 286, 289, 297, 298, 303, 305, 307, 308, 309, 311, 312, 314, 315, 317, 325, 332, 334, 360, 376, 380, 382, 384, 385, 386, 387, 389, 424, 428, 433, 434 or 436 (EU numbering) relative to the native human Fc constant region. In some embodiments, the substitution is selected from the group consisting of: methionine for glycine at position 237; alanine for proline at position 238; lysine for serine at position 239; isoleucine for lysine at position 248; alanine, phenylalanine, isoleucine, methionine, glutamine, serine, valine, tryptophan or tyrosine for threonine at position 250; phenylalanine, tryptophan or tyrosine for methionine at position 252; threonine for serine at position 254; glutamic acid for arginine at position 255; aspartic acid, glutamic acid or glutamine for threonine at position 256; alanine, glycine, isoleucine, leucine, methionine, asparagine, serine, threonine or valine for proline at position 257; histidine for glutamic acid at position 258; alanine for aspartic acid at position 265; phenylalanine for aspartic acid at position 270; alanine or glutamic acid for asparagine at position 286; histidine for threonine at position 289; alanine for asparagine at position 297; glycine for serine at position 298; alanine for valine at position 303; alanine for valine at position 305; alanine, aspartic acid, phenylalanine, glycine, histidine, isoleucine, lysine, leucine, methionine, asparagine, proline, glutamine, arginine, serine, valine, tryptophan or tyrosine for threonine at position 307; alanine, phenylalanine, isoleucine, leucine, methionine, proline, glutamine or threonine for valine at position 308; alanine, aspartic acid, glutamic acid, proline or arginine for leucine or valine at position 309; alanine, histidine or isoleucine for glutamine at position 311; alanine or histidine for aspartic acid at position 312; lysine or arginine for leucine at position 314; alanine or histidine for asparagine at position 315; alanine for lysine at position 317; glycine for asparagine at position 325; valine for isoleucine at position 332; leucine for lysine at position 334; histidine for lysine at position 360; alanine for aspartic acid at position 376; alanine for glutamic acid at position 380; alanine for glutamic acid at position 382; alanine for asparagine or serine at position 384; aspartic acid or histidine for glycine at position 385; proline for glutamine at position 386; glutamic acid for proline at position 387; alanine or serine for asparagine at position 389; alanine for serine at position 424; alanine, aspartic acid, phenylalanine, glycine, histidine, isoleucine, lysine, leucine, asparagine, proline, glutamine, serine, threonine, valine, tryptophan or tyrosine for methionine at position 428; lysine for histidine at position 433; alanine, phenylalanine, histidine, serine, tryptophan or tyrosine for asparagine at position 434; and histidine for tyrosine or phenylalanine at position 436, all in EU numbering.

Exemplary anti-C5 antibodies comprise a heavy chain polypeptide comprising the amino acid sequence set forth in SEQ ID NO:14 and/or a light chain polypeptide comprising the amino acid sequence set forth in SEQ ID NO:11. Alternatively, the anti-C5 antibodies can comprise a heavy chain polypeptide comprising the amino acid sequence set forth in SEQ ID NO:20 and/or a light chain polypeptide comprising the amino acid sequence set forth in SEQ ID NO:11.

In one embodiment, the antibody binds to C5 at pH 7.4 and 25° C. (and, otherwise, under physiologic conditions) with an affinity dissociation constant ($K_D$) that is at least 0.1 (e.g., at least 0.15, 0.175, 0.2, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95 or 0.975) nM. In some embodiments, the $K_D$ of the anti-C5 antibody, or antigen binding fragment thereof, is no greater than 1 (e.g., no greater than 0.9, 0.8, 0.7, 0.6, 0.5, 0.4, 0.3 or 0.2) nM.

In other embodiments, the [($K_D$ of the antibody for C5 at pH 6.0 at 25° C.)/($K_D$ of the antibody for C5 at pH 7.4 at 25° C.)] is greater than 21 (e.g., greater than 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1500, 2000, 2500, 3000, 3500, 4000, 4500, 5000, 5500, 6000, 6500, 7000, 7500 or 8000).

The following examples are merely illustrative and should not be construed as limiting the scope of this disclosure in any way as many variations and equivalents will become apparent to those skilled in the art upon reading the present disclosure. The contents of all references, Genbank entries, patents and published patent applications cited throughout this application are expressly incorporated herein by reference.

Examples

Example 1: Ravulizumab Manufacturing Process

A vial of the Working Cell Bank (WCB) containing 3A5-50D6 cells of Chinese hamster ovary (CHO) origin was thawed and cultures were progressively expanded using growth medium through a series of cell culture steps using shake flasks, rocker bioreactors, and seed expansion bioreactors prior to inoculation into the production bioreactor. Upon completion of the cell culture steps, cells and cell debris were removed by a series of depth filters. The clarified harvest was filtered through a 0.5/0.2 μm filter prior to purification.

The downstream ravulizumab drug substance manufacturing process includes three chromatography steps (MabSelect SuRe™ Protein A affinity chromatography, POROS® HS50 cation exchange (CEX) chromatography, and POROS® HQ50 anion exchange (AEX) chromatography), a low pH virus inactivation step, and a virus filtration (20 nm) step. Following the final concentration/diafiltration and formulation step, the formulated diluted ultrafiltration/diafiltration (UF/DF) pool was 0.5/0.2 μm filtered into containers and ravulizumab drug substance was stored at 2-8° C. pending batch disposition, long term storage and shipment to the drug product manufacturing facility. A flow diagram of the manufacturing process for ravulizumab drug substance is set forth in FIG. 1. Throughout the manufacturing process, single use consumables including bioreactor bags, intermediate hold vessels and filters were utilized.

The criticality of all parameters and attributes of the drug substance manufacturing process has been determined to employ a comprehensive control strategy for ravulizumab that ensures consistent potency and safety of the drug substance. Upon transfer to the manufacturing site, a facility specific risk assessment was completed to align with site policy/definitions. There was no change in the criticality assigned to any parameter or attribute from the control strategy.

Process characterization studies, driven by risk assessments, were completed to determine a proven acceptable range (PAR) for each parameter identified within the manufacturing process that has the potential to impact product quality. A normal operating range (NOR) that is within or equal to the PAR was specified for routine operation within the manufacturing process description. During routine processing, any excursion outside of the NOR would have prompted the initiation of a deviation and subsequent investigation. Following investigation, material would have been dispositioned accordingly.

Ravulizumab was manufactured in CHO cells at the 2,000 L bioreactor scale. The cells used to inoculate the 2,000 L production bioreactor originated from a single WCB vial. Multiple drug substance batches, however, could have been produced from a single vial of WCB by utilizing rollback cultures. Each drug substance batch yielded approximately 300 L at a concentration of 10 g/L ravulizumab. Antibody expression and step yields are factors in the ravulizumab drug substance manufacturing process that affect the individual batch yield. A unique identifying batch number was assigned for each unit operation. In the event of reprocessing at the viral filtration or bulk filtration steps, a new unique identifying batch number was assigned.

1. Cell Culture and Primary Recovery

This section describes the cell culture and primary recovery (harvesting) process for the manufacture of ravulizumab drug substance. The cell culture and harvesting process comprised three discrete steps (inoculum expansion, cell culture in production bioreactor, and primary recovery) as summarized in FIG. 1 and detailed further in FIGS. 2-4.

a. Step 1: Inoculum Expansion

Figure 2:
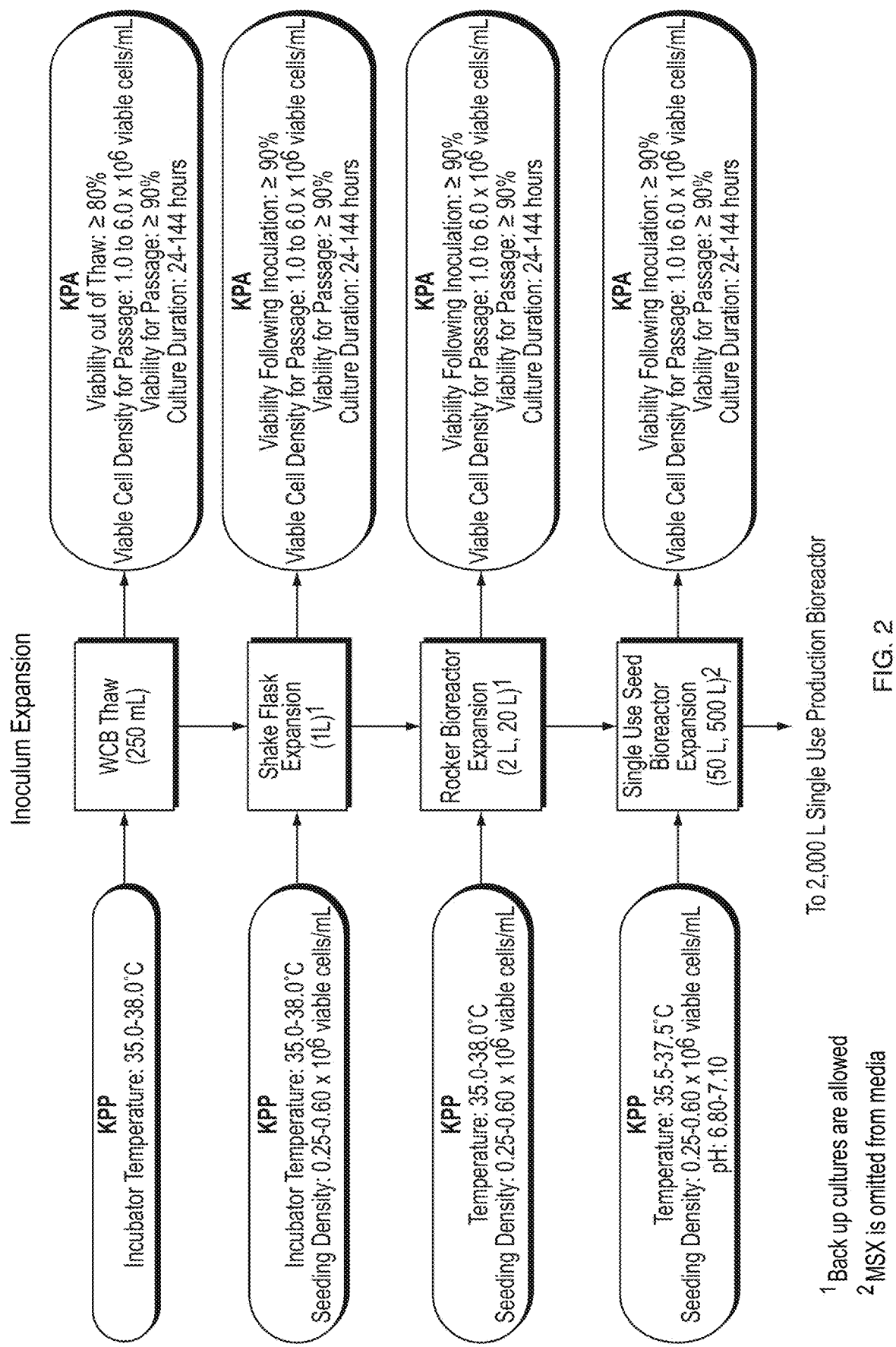
FIG. 2 depicts the process flow and key process parameters (KPP) and key process attributes (KPA) for the inoculum expansion manufacturing process.

The purpose of the inoculum expansion process step was to expand the WCB to a sufficient cell mass to inoculate the 2,000 L production bioreactor. The temperature of the culture conditions during the inoculum expansion step was maintained at a set point of 36.5° C. FIG. 2 outlines the process flow and key process parameters (KPP) and key process attributes (KPA) for the inoculum expansion manufacturing process. Table 1 includes the KPP and KPA for the inoculum expansion.

A vial of the WCB was removed from vapor phase of liquid nitrogen storage and transferred to a biosafety cabinet in the production suite. The cells were thawed, washed to remove the cryopreservation medium, and re-suspended and cultured in a 250 mL shake flask with inoculum media (CD-CHO AGT medium supplemented with 25 μM L-methionine sulfoximine (MSX)). The flask culture was incubated under 10% $CO_2$ and agitation for up to 6 days until the criteria described in Table 1 were met prior to seeding into a 1 L shake flask. This initiates the shake flask phase of the inoculum expansion.

The cells were expanded in inoculum media incubated under 10% $CO_2$ and agitation for up to 6 days until the criteria described in Table 1 were met prior to seeding into the rocker bioreactor phase of inoculum expansion. The 1 L shake flask culture could have been used to inoculate a backup culture. If the backup culture was not needed, it was discarded at the 20 L rocker bioreactor expansion.

The cells were further expanded in inoculum media in rocker bioreactors with increasing volumes (2 L to 20 L) prior to transitioning from rocker bioreactors to a 50 L seed bioreactor. Each rocker bioreactor was incubated with 5% $CO_2$ and rocked for up to 6 days until the criteria described in Table 1 were met prior to proceeding into the next rocker bioreactor of increased size or seeding into the seed bioreactor phase of inoculum expansion. If required, the 20 L rocker bioreactor culture could have been used to inoculate a rollback 2 L culture.

The cells were expanded in expansion media (CD-CHO AGT medium without MSX supplementation) in single use bioreactors (SUB) with increasing volumes (50 L to 500 L) prior to transitioning to Step 2 of the process. Following inoculation, each SUB was sparged with air and oxygen as required with agitation for up to 6 days until the criteria described in Table 1 was met prior to proceeding to the next SUB of increased size or proceeding to Step 2 of the process. A dissolved oxygen set point of 30% and pH of set point of 6.95 was maintained. pH was controlled using sodium carbonate as base and $CO_2$ as acid. Antifoam (animal-origin free) could have been added to the seed bioreactor if necessary to control foaming.

TABLE 1

Processing Conditions for Inoculum Expansion

| Parameter/Attribute | Acceptance Limits NOR | PAR | Designation |
|---|---|---|---|
| Vial Thaw | | | |
| Incubator Temperature | 35.0-38.0° C. | 34.5-38.5° C. [1] | KPP |
| Viability Out of Thaw | ≥80% | | KPA |
| Viable Cell Density for Passage | 1.0 to 6.0 × 10⁶ viable cells/mL | | KPA |
| Viability for Passage | ≥90% | | KPA |
| Cell Culture Duration | 24-144 hours | | KPA |
| Shake Flask Expansion | | | |
| Incubator Temperature | 35.0-38.0° C. | 34.5-38.5° C. [1] | KPP |
| Seeding Density | 0.25-0.60 × 10⁶ viable cells/mL | 0.20-0.80 × 10⁶ viable cells/mL | KPP |
| Viability Following Inoculation | ≥90% | | KPA |
| Viable Cell Density for Passage | 1.0 to 6.0 × 10⁶ viable cells/mL | | KPA |
| Viability for Passage | ≥90% | | KPA |
| Cell Culture Duration | 24-144 hours | | KPA |
| Rocker Bioreactor Expansion | | | |
| Temperature | 35.0-38.0° C. | 34.5-38.5° C. | KPP |
| Seeding Density | 0.25-0.60 × 10⁶ viable cells/mL | 0.20-0.80 × 10⁶ viable cells/mL | KPP |
| Viability Following Inoculation | ≥90% | | KPA |
| Viable Cell Density for Passage | 1.0 to 6.0 × 10⁶ viable cells/mL | | KPA |
| Viability for Passage | ≥90% | | KPA |
| Cell Culture Duration | 24-144 hours | | KPA |
| Seed Bioreactor Expansion | | | |
| Temperature | 35.5-37.5° C. | 35.0-38.0° C. | KPP |
| Seeding Density | 0.25-0.60 × 10⁶ viable cells/mL | 0.20-0.80 × 10⁶ viable cells/mL | KPP |
| pH | 6.80-7.10 | 6.70-7.20 | KPP |
| Viability Following Inoculation | ≥90% | | KPA |
| Viable Cell Density for Passage | 1.0 to 6.0 × 10⁶ viable cells/mL | | KPA |
| Viability for Passage | ≥90% | | KPA |
| Cell Culture Duration | 24-144 hours | | KPA |

Figure 3:
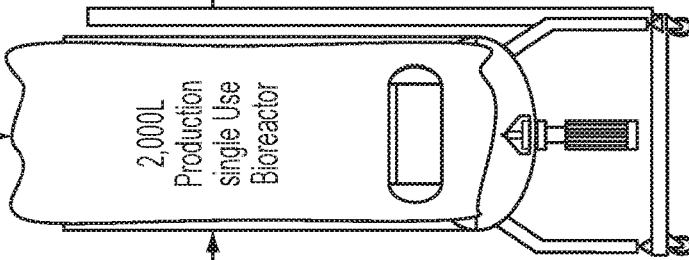
FIG. 3 depicts the process flow and critical and key process parameters (CPP, KPP), in process controls (IPC) and key process attributes for the cell culture process in the production bioreactor.

[1] Transient temperature fluctuation of ≤15 minutes outside the PAR due to flask sampling are allowed and do not constitute an excursion b. Step 2: Cell Culture in Production Bioreactor The purpose of this step was to produce the ravulizumab antibody. FIG. 3 outlines the process flow and critical process parameters (CPPs) and KPPs, in process controls (IPC) and KPAs for the cell culture process in the production bioreactor.

Copper sulfate pentahydrate was added to the 2,000 L production bioreactor at a concentration of 20 μM. The 500 L SUB cell culture was inoculated into production media (CD-CHO AGT medium supplemented with 0.34 g/kg L-cysteine hydrochloride monohydrate and 0.27 g/kg L-tyrosine). The pH of the bioreactor was controlled by use of $CO_2$ for acidic control and 1 M sodium carbonate for base control. The pH was maintained at a target of 6.95 and the temperature was maintained at a target of 36.5° C. To minimize foaming, antifoam could have been added when there was excessive foam. The dissolved oxygen was controlled at a set point of 30% by sparging air and oxygen as required. The culture was supplemented with glucose as needed. Efficient Feed C+ was added to the production bioreactor on Day 4, Day 6 and Day 8.

The production bioreactor phase of the process continued until the harvest criteria specified in Table 3 was met prior to proceeding to Step 3 of the process. Samples were taken for bioburden, *mycoplasma*, in vitro virus assay, and murine minute virus assay by quantitative polymerase chain reaction (q-PCR).

TABLE 2

Critical Processing Conditions for Cell Culture in Production Bioreactor

| Parameter/Attribute | Acceptable Limit NOR | Acceptable Limit PAR | Designation |
|---|---|---|---|
| Seeding Density | 0.30-0.70 × $10^6$ viable cells/mL | 0.20-0.80 × $10^6$ viable cells/mL | CPP |
| Dissolved Oxygen (DO) | 20-50% of air saturation | 10-60% of air saturation [1] | CPP |
| Efficient Feed C+ Feed Amount | Target of 5% (v/v) of initial working volume ± 5% (for each feed bolus) | Target of 5% (v/v) of initial working volume ± 10% (for each feed bolus) | CPP |
| Efficient Feed C+ Schedule (days post-inoculation) | 4.0, 6.0 and 8.0 days (±8 hours) | 4.0, 6.0 and 8.0 days (±24 hours) | CPP |
| Duration | 13.0 to 16.0 days post-inoculation | 12.0 to 18.0 days post-inoculation | CPP |
| Mycoplasma | Negative | | IPC |
| In vitro virus assay (3 cell lines: MRC-5, VERO and CHO-K1) | Not Detected | | IPC |
| Murine minute virus assay by q-PCR | Not Detected | | IPC |

[1] Range applicable after DO drops to set point in the first few days of the culture (typically 0-3 days). DO excursions down to 0% or up to 100% for up to 1 hour is acceptable. In addition, DO excursions to ≤5% for up to 24 hours during growth phase (days 0-6) was acceptable.

TABLE 3

Key Processing Conditions for Cell Culture in Production Bioreactor

| Parameter/Attribute | Acceptable Limit NOR | Acceptable Limit PAR | Designation |
|---|---|---|---|
| Temperature | 35.5-37.5° C. | 35.0-38.0° C. | KPP |
| pH | 6.80-7.10 | 6.75-7.20 [1] | KPP |
| $pCO_2$ | ≤200 mmHg | ≤250 mmHg [2] | KPP |
| Maximum Cell Generations at Inoculation | ≤50.0 | ≤52.6 | KPP |
| Viability Following Inoculation | ≥80% | | KPA |
| Peak/Maximum Viable Cell Density | ≥12.0 × $10^6$ viable cells/mL | | KPA |
| Day of Harvest Bioburden | <3 CFU/2 mL | | KPA |
| Viability at Harvest | ≥30% | | KPA |
| Titer | ≥2.5g/L | | KPA |

[1] pH excursions up to 7.60 for a maximum of 3 hours were acceptable during stationary phase (days 7-10), pH excursions for a maximum of 3 hours were acceptable during stationary phase (days 7-10) and death phase of the cell culture (day 11-14).
[2] $pCO_2$ excursions over 250 mmHg for purpose of pH control were acceptable.

c. Step 3: Primary Recovery: Clarification and Post-Harvest 0.5/0.2 μm Filtration The primary recovery step separates the ravulizumab antibody in the cell culture broth from the cells and cellular debris. The depth filtration train was flushed and equilibrated prior to use. The cell culture broth was filtered and chased through a two-step depth filtration train in series immediately followed by filtration through two 0.5/0.2 μm filters in series into a jacketed 2,000 L single-use mixing bioprocess container.

Figure 4:
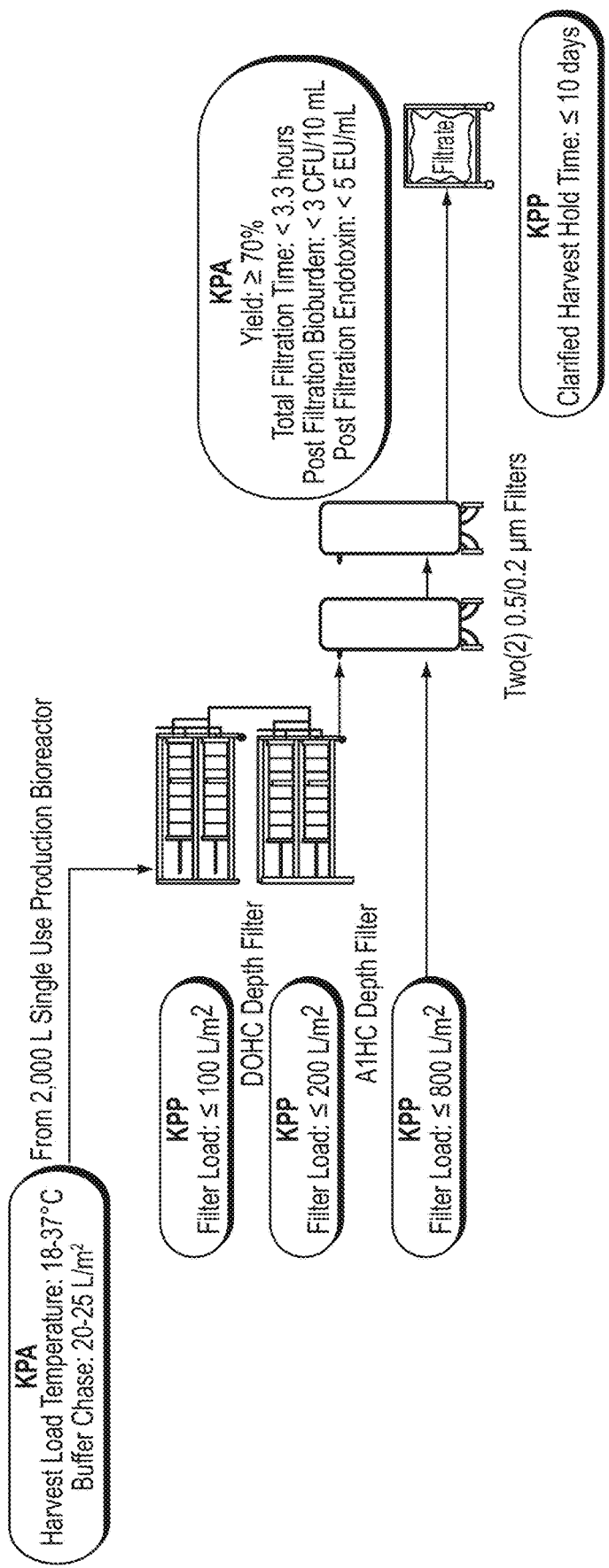
FIG. 4 depicts the process flow and KPPs and KPAs for step 3 of the ravulizumab manufacturing process.

FIG. 4 outlines the process flow and KPPs and KPAs for the ravulizumab Step 3 of the manufacturing process. Buffers used in the primary recovery step are presented in Table 4. Table 5 includes the KPPs and KPAs for the primary recovery step.

TABLE 4

Buffers used for Primary Recovery

| Process Step | Buffer |
|---|---|
| Flush | WFI |
| Equilibration/Chase | 20 mM Tris, 65 mM Sodium Chloride, pH 7.6 |

TABLE 5

Key Processing Conditions for Primary Recovery

| | Acceptable Limit | | |
|---|---|---|---|
| Parameter/Attribute | NOR | PAR | Designation |
| D0HC Depth Filter Load | ≤100 L/m² | ≤100 L/m² | KPP |
| A1HC Depth Filter Load | ≤200 L/m² | ≤200 L/m² | KPP |
| 0.5/0.2 pm Filter Load | ≤800 L/m² | ≤800 L/m² | KPP |
| Harvest Load Temperature | 18-37° C. | 15-37° C. | KPP |
| Buffer Chase Volume | 20-25 L/m² | 0-30 L/m² | KPP |
| Clarified Harvest Hold Time (start of harvest filtration through end of final Pro A cycle load) | ≤10 Days | ≤16 Days | KPP |
| Yield | | ≥70% | KPA |
| Total Filtration Time (start through end of harvest filtration ¹) | | <3.3 hours | KPA |
| Bioburden | | <3 CFU/10 mL | KPA |
| Endotoxin | | <5 EU/mL | KPA |

¹ Excluding flush and equilibration

2. Purification and Modification Reactions

Figure 5:
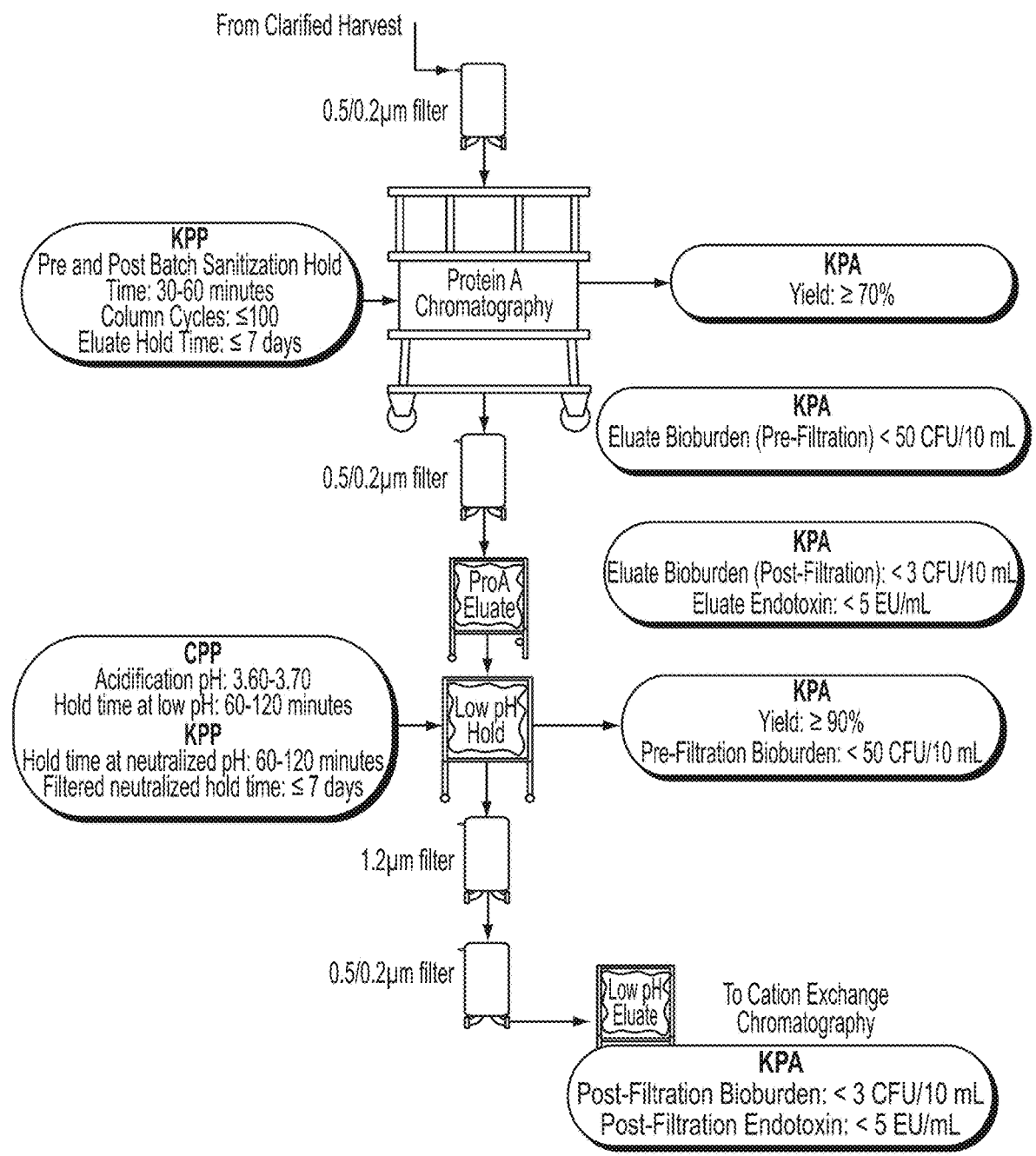
FIG. 5 sets forth an overview of the ravulizumab purification process.
Figure 5:
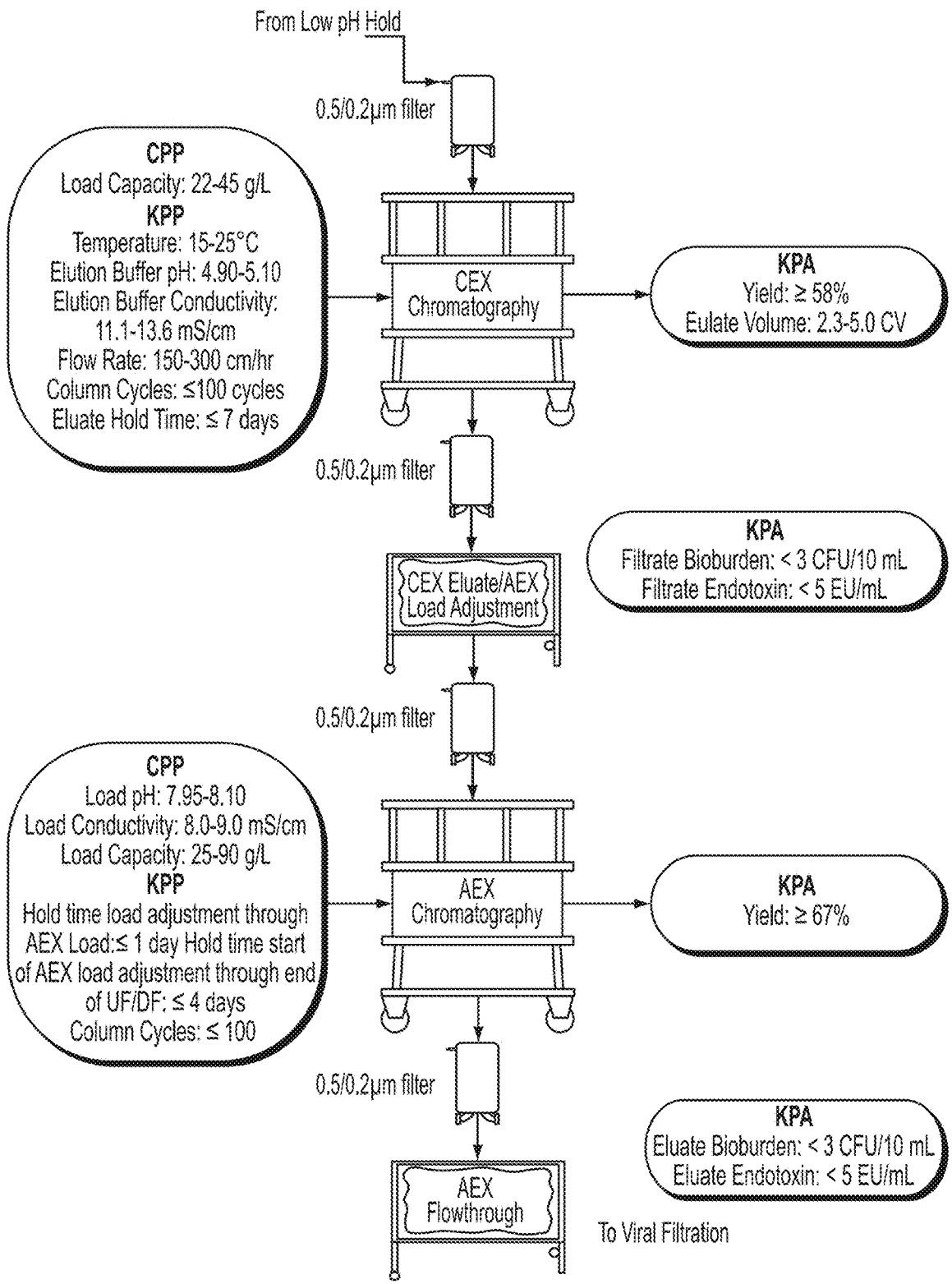
Figure 5:
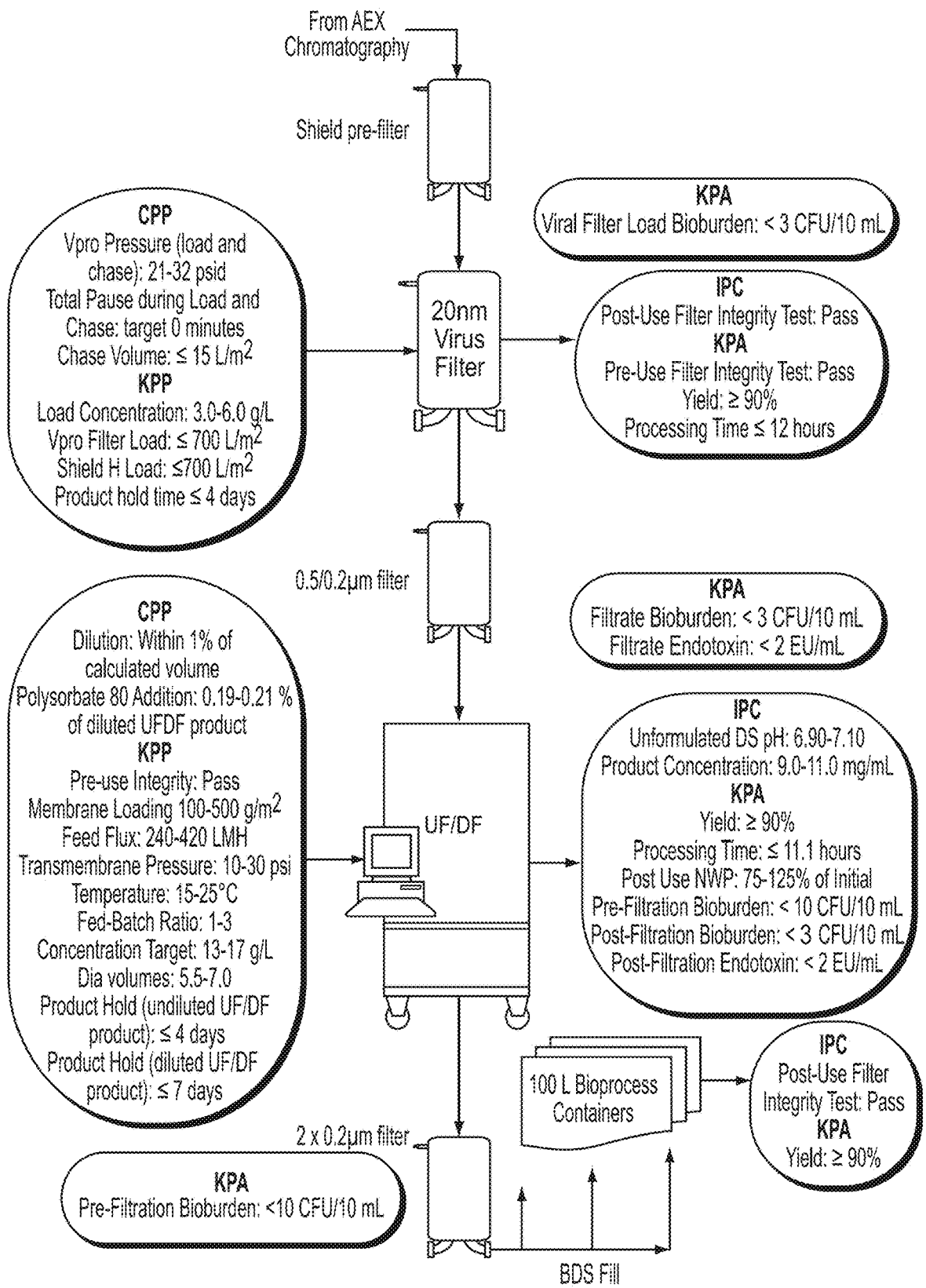

The purification process was designed to purify ravulizumab by removal of process and product related impurities from the clarified harvest using orthogonal purification steps, followed by concentration and formulation into bulk drug substance (BDS). FIG. 5 provides an overview of the ravulizumab purification process. The temperature during the entire purification process was maintained at ambient temperature.

The purification process started with the capture of the ravulizumab antibody by MabSelect SuRe Protein A affinity chromatography. This pool was then treated with a low pH viral inactivation hold, followed by further purification by POROS HS50 CEX chromatography and POROS HQ50 AEX chromatography steps. This pool was then filtered through a VIRESOLVE® 20 nm virus reduction filtration step. This filtrate was concentrated and diafiltered into the drug product formulation buffer. Finally, polysorbate 80 was added to complete formulation of the product. The resulting material was 0.5/0.2 µm filtered into bags for storage at 2-8° C. prior to shipment for drug product manufacturing.

Throughout the process 0.5/0.2 µm filtration was used as described in FIG. 5. Process intermediates were sampled for bioburden and endotoxin at the end of their respective in process holds, just prior to filtration. Limits for microbial monitoring were included in Table 7, Table 9, Table 12, Table 15, Table 18, Table 21 and Table 23.

a. Step 4: MabSelect SuRe Protein A Affinity Chromatography

The purpose of this step was the primary capture of the ravulizumab antibody. Protein A chromatography is an affinity chromatography step in which the resin selectively binds to the FC portion of ravulizumab, allowing impurities to flow through the packed column. The bound product is then eluted from the resin by decreasing the pH with the elution buffer. Buffers used for this step are listed in Table 6.

Before first use of each batch and after every cycle, the column is cleaned/sanitized and equilibrated. Following column packing, the column performance was verified to achieve number of theoretical plates ≥1000 N/m (KPA) and an asymmetry factor of 0.8-1.6 (KPA).

The clarified harvest material from Step 3 served as the load for the MabSelect SuRe column. The material was loaded onto the column through a 0.5/0.2 µm filter. Impurities were removed with wash buffers. The product was eluted from the column using elution buffer. This step was normally operated in three cycles per batch and the eluates were pooled for further processing. The pool was stored at ambient temperature prior to the start of the next process step.

Table 7 summarizes the KPPs and KPAs for the MabSelect SuRe chromatography step. The column load was calculated based on titer by Protein A HPLC of the clarified harvest. The step yield was based on the concentration measurement (based on ProA titer) from the clarified harvest and the concentration measured by $A_{280}$ from the MabSelect SuRe Protein A Affinity pool. After each cycle, the column was stripped, flushed, and cleaned/sanitized.

TABLE 6

Buffers used for the MabSelect SuRe
Protein A Affinity Chromatography

| Process Step | Buffer |
|---|---|
| Sanitization | 0.1N Sodium Hydroxide |
| Equilibration | 20 mM Tris, 65 mM Sodium Chloride, pH 7.6 |
| Post-Load Wash 1 | |
| Post-Load Wash 2 | 50 mM Sodium Phosphate, 100 mM Sodium Chloride, 300 mM Arginine Hydrochloride, pH 6.0 |
| Post-Load Wash 3 | 20 mM Tris, 65 mM Sodium Chloride, pH 7.6 |
| Elution | 25 mM Sodium Acetate, pH 3.75 |
| Strip | 100 mM Acetic Acid |
| Flush | WFI |
| Storage | 20% Ethanol |

TABLE 7

Key Processing Conditions for the MabSelect SuRe Protein A Affinity Chromatography

| Parameter/Attributes | Acceptable Limit NOR | Acceptable Limit PAR | Designation |
|---|---|---|---|
| Pre-Batch Sanitization Hold Time | 30-60 minutes | 30-75 minutes | KPP |
| Post-Batch Sanitization Hold Time | 30-60 minutes | 30-75 minutes | KPP |
| Column Cycles | ≤100 | ≤100 | KPP |
| Eluate Hold Time (end of filtration through start of low pH acidification) | ≤7 days | ≤10 days | KPP |
| Step Yield | ≥70% | | KPA |
| Eluate Bioburden (pre-filtration) | <50 CFU/10 mL | | KPA |
| Eluate Bioburden (Post-Filtration) | <3 CFU/10 mL | | KPA |
| Eluate Endotoxin (Post-Filtration) | <5 EU/mL | | KPA | b. Step 5: Low pH Hold Viral Inactivation

The purpose of this step was to inactivate potential enveloped viruses in the process stream by low pH treatment. The Protein A pool was treated with 1 M acetic acid to a pH range of 3.60 to 3.70. Following the pH adjustment, the pool was transferred to a second vessel and incubated at ambient temperature for a minimum of 60 minutes without mixing during hold. At the completion of the incubation, the pH was measured again following the incubation to be within 3.60 to 3.75. Following the hold, the pH was increased to pH 5.0 using 1 M Tris and incubated at ambient temperature for a minimum of 60 minutes without mixing during the hold to allow consistent precipitate formation that is subsequently removed by filtration. The neutralized viral inactivated material was pre-filtered and then 0.5/0.2 μm filtered and stored at ambient temperature until the initiation of Step 6.

Table 8 summarizes the CPPs and acceptance criteria. Table 9 summarizes the KPPs and KPAs for the low pH virus inactivation step. The step yield was based on the concentration measurement ($A_{280}$) from the MabSelect SuRe Protein A Affinity pool and the concentration measure by $A_{280}$ from the neutralized viral inactivated material.

TABLE 8

Critical Processing Conditions for the Low pH Virus Inactivation

| Parameter | Acceptable Limit NOR | Acceptable Limit PAR | Designation |
|---|---|---|---|
| Acidification pH Immediately After Titration | 3.60-3.70 | 3.55-3.80 | CPP |
| Acidification pH After Hold Time | 3.60-3.75 | 3.55-3.80 | CPP |
| Hold Time at Low pH | 60-120 minutes | 60-360 minutes | CPP |

TABLE 9

Key Processing Conditions for the Low pH Virus Inactivation

| Parameter | Acceptable Limit NOR | Acceptable Limit PAR | Designation |
|---|---|---|---|
| Hold Time at Neutralized pH Prior to 0.5/0.2 μm Filtration | 60-120 minutes | ≥60 minutes | KPP |
| Filtered Neutralized Product Hold Time (end of filtration) through end of CEX load) | ≤7 days | ≤10 days | KPP |
| Yield | ≥90% | | KPA |
| Neutralized Pool Bioburden (Pre-Filtration) | <50 CFU/10 mL | | KPA |
| Neutralized Pool Bioburden (Post-Filtration) | <3 CFU/10 mL | | KPA |
| Neutralized Pool Endotoxin (Post-Filtration) | <5 EU/mL | | KPA | c. Step 6: POROS HS50 Cation Exchange Chromatography (CEX)

The purpose of this step is to remove high-molecular-weight impurities as well as other process-related impurities and potential viruses from the process stream. The in-process material from the viral inactivation step was purified using a chromatography column in which the product binds to POROS HS50 CEX resin. The bound product was then eluted from the resin by increasing ionic strength with the elution buffer. This step was normally operated in one cycle.

Before use and after every batch the column was sanitized. Buffers used for this step are listed in Table 10. Following column packing, the column performance was verified to achieve number of theoretical plates ≥1000 N/m (KPA) and an asymmetry factor of 0.8-1.6 (KPA).

For each cycle load, the neutralized filtrate from the low pH hold, served as the load for the cation exchange column. The material was loaded onto the column through a 0.5/0.2 μm filter. The product was eluted from the column using elution buffer. The single eluate was collected through an inline 0.5/0.2 μm filter and stored at ambient temperature until the initiation of Step 7.

Table 11 summarizes the CPP and acceptance criteria and Table 12 summarizes the KPPs and KPAs for the CEX step. The column load was calculated based on the $A_{280}$ of the filtrate from Step 5. The step yield was based on the $A_{280}$ measurement from the Low pH filtrate and CEX filtered eluate. After each cycle, the column was stripped, cleaned/sanitized, flushed and stored in final storage solution.

TABLE 10

Buffers used for the POROS HS50 CEX Chromatography

| Process Step | Buffer |
|---|---|
| Equilibration | 50 mM Sodium Acetate, pH 5.0 |
| Post-Load Wash 1 | |
| Post-Load Wash 2 | 50 mM Sodium Acetate, 60 mM Sodium Chloride, pH 4.9 |
| Elution | 50 mM Sodium Acetate, 90 mM Arginine Hydrochloride, 30 mM Sodium Chloride, pH 5.0 |
| Strip | 2.0M Sodium Chloride |
| Sanitization | 1.0N Sodium Hydroxide |
| Storage | 0.1N Sodium Hydroxide |

TABLE 11

Critical Processing Conditions for the POROS HS50 CEX Chromatography

| | Acceptable Limit | | |
|---|---|---|---|
| Parameter | NOR | PAR | Designation |
| Load Capacity | 22-45 g/L | 15-50 g/L | CPP |

TABLE 12

Key Processing Conditions for the POROS HS50 CEX Chromatography

| | Acceptable Limit | | |
|---|---|---|---|
| Parameter/Attributes | NOR | PAR | Designation |
| Temperature | 15-25° C. | 13-27° C. | KPP |
| Elution Buffer pH | 4.90-5.10 | 4.90-5.10 | KPP |
| Elution Buffer Conductivity | 11.1-13.6 mS/cm | 11.1-13.6 mS/cm | KPP |
| Elution Flow Rate | 150-300 cm/hr | 120-330 cm/hr | KPP |
| Eluate Hold Time (start of eluate collection through end of AEX load adjustment) | ≤7 days | ≤10 days | KPP |
| Column Cycles | ≤100 | ≤100 | KPP |
| Eluate Bioburden (post-filtration) | <3 CFU/10 mL | | KPA |
| Eluate Endotoxin (post-filtration) | <5 EU/mL | | KPA |
| Step Yield | ≥58% | | KPA |
| Eluate Volume | 2.3-5.0 column volumes | | KPA | d. Step 7: POROS HQ50 Anion Exchange Chromatography (AEX)

The purpose of this step was to further remove high-molecular-weight impurities, as well as other process related impurities and potential viruses from the process stream. The adjusted CEX eluate was further purified using a chromatography column packed with POROS HQ50 anion exchange resin and operated in flow-through mode. The step is normally operated in one cycle.

The CEX pool was adjusted to a pH of 8.00 and conductivity of 8.5 mS/cm with 100 mM Tris (pH 9.0), 180 mM arginine and WFL. Processing over the chromatography column was initiated within 24 hours of the load adjustment.

Before use, the column was sanitized, conditioned and equilibrated. Buffers used for this step are listed in Table 13. Following column packing, the column performance was verified to achieve number of theoretical plates ≥1000 N/m (KPA) and an asymmetry factor of 0.8-1.6 (KPA). The adjusted material was loaded onto the column through a 0.5/0.2 μm filter. The product was chased from the column using buffer filtered through an inline 0.5/0.2 μm into the filtrate vessel.

Table 14 summarizes the CPP and acceptance criteria and Table 15 summarizes the KPPs and KPAs for the AEX step. The adjusted material column load was calculated based on the $A_{280}$ of the filtrate from the CEX step. The expected step yield was based on the $A_{280}$ measurement from the CEX and AEX pools. After each cycle, the column was stripped, sanitized and stored.

TABLE 13

Buffers used for the POROS HQ50 AEX Chromatography

| Process Step | Buffer |
|---|---|
| Load pH Adjustment | 100 mM Tris, 180 mM Arginine, pH 9.0 |
| Load Conductivity Adjustment Flush | WFI |
| Conditioning | 2M Sodium Chloride |
| Equilibration | 20 mM Tris, 65 mM Sodium Chloride, pH 7.6 |

TABLE 13-continued

Buffers used for the POROS HQ50 AEX Chromatography

| Process Step | Buffer |
| --- | --- |
| Post-Load Chase | |
| Post-Elution Strip | 2M Sodium Chloride |
| Sanitization | 1.0N Sodium Hydroxide |
| Storage | 0.1N Sodium Hydroxide |

TABLE 14

Critical Processing Conditions for the POROS HQ50 AEX Chromatography

| | Acceptable Limit | | |
| --- | --- | --- | --- |
| Parameter | NOR | PAR | Designation |
| Load pH | 7.90-8.10 | 7.80-8.20 | CPP |
| Load Conductivity | 8.0-9.0 mS/cm | 7.0-10.0 mS/cm | CPP |
| Load Capacity | 25-90 g/L | 25-100 g/L | CPP |

TABLE 15

Key Processing Conditions for the POROS HQ50 AEX Chromatography

| | Acceptable Limit | | |
| --- | --- | --- | --- |
| Parameter/Attribute | NOR | PAR | Designation |
| Hold Time (AEX load adjustment through start of AEX Load) | ≤1 day | ≤4 days | KPP |
| Product Hold Time (end of AEX load adjustment through end of UF/DF) | ≤4 days | ≤6 days | KPP |
| Column Cycles | ≤100 | ≤100 | KPP |
| Eluate Bioburden (post-filtration) | <3 CFU/10 mL | | KPA |
| Eluate Endotoxin (post-filtration) | <5 EU/mL | | KPA |
| Yield | ≥67% | | KPA | e. Step 8: Viral Filtration (20 nm)

The purpose of this step was to remove potential viruses or virus-like particles from the process stream on the basis of size. Viral reduction was accomplished by filtration of the AEX flow-through filtrate through a VIRESOLVE® Pro Shield H pre-filter followed by filtration through a VIRESOLVE® Pro filter (20 nm).

Prior to use, the 20 nm filters were integrity tested and were flushed using WFI and buffer. The material was loaded onto the filter followed by a flush with 20 mM Tris (pH 7.6), 65 mM sodium chloride to minimize product loss. The VIRESOLVE® filtrate was 0.5/0.2 µm filtered. The virus reduction filter was post-use integrity tested.

Table 16 includes the buffers used at this step. The filters were integrity tested. In the event that it was determined reprocessing was justified, the material could have been reprocessed once. Reprocessing was not conducted due to bioburden above the action limits. Table 17 summarizes the CPPs and the acceptance criteria and Table 18 summarizes the KPPs and KPAs for this virus filtration step. The step yield was based on the A280 measurements from the AEX filtrate and VIRESOLVE® filtrate and was stored at ambient conditions.

TABLE 1

Buffers used for the Virus Filtration

| Process Step | Buffer |
| --- | --- |
| Pre-use Flush | WFI |
| Equilibration | 20 mM Tris, 65 mM |
| Post-Loading Chase | Sodium Chloride, pH 7.6 |

TABLE 2

Critical Processing Conditions for the Virus Filtration

| | Acceptable Limit | | |
| --- | --- | --- | --- |
| Parameter | NOR | PAR | Designation |
| VIRESOLVE ® Filter Differential Pressure During Load and Chase | 21-32 psid | 21-35 psid | CPP |
| Total Pause Time during Load and Chase | 0 minutes | ≤120 minutes | CPP |
| Chase Volume | ≤15 L/m² | ≤20 L/m² | CPP |
| Post-Use Integrity Test | Pass | | IPC |

TABLE 18

Key Processing Conditions for the Virus Filtration

| | Acceptable Limit | | |
| --- | --- | --- | --- |
| Parameter/Attribute | NOR | PAR | Designation |
| Load Concentration | 3.0-6.0 g/L | ≤6.7 g/L | KPP |
| Shield H Pre-Filter Load | ≤700 L/m² | ≤1200 L/m² | KPP |
| Viresolve Pro Filter Load | ≤700 L/m² | ≤700 L/m² | KPP |
| Product Hold Time (end of AEX load adjustment through end of UFDF) | ≤4 days | ≤6 days | KPP |
| Bioburden (pre-filtration viral filter load) | <3 CFU/10 mL | | KPA |
| Bioburden (viral filtrate) | <3 CFU/10 mL | | KPA |
| Endotoxin (viral filtrate) | <2 EU/mL | | KPA |
| Pre-Use Integrity Test | Pass | | KPA |
| Processing Time (start of load to end of load) | ≤12 hours | | KPA |
| Step Yield | ≥90% | | KPA | f. Step 9: Ultrafiltration/Diafiltration (30 kDa) and Formulation

The purpose of this UF/DF step was to concentrate the process stream to its specified concentration and to exchange the in process buffer with the formulation buffer (10 mM sodium phosphate (pH 7.0), 150 mM sodium chloride) and then complete formulation by the addition of polysorbate 80.

Before use, product dedicated UF membranes were flushed, integrity tested and sanitized. The membranes were then equilibrated prior to loading of the viral filtrate. The buffers used in this step are outlined in Table 19.

The pool from the virus reduction filtration step was concentrated to a target of 15 g/L using 30 kDa MWCO UF membranes. The concentrated pool was then diafiltered with 6 diafiltration volumes into formulation buffer (10 mM sodium phosphate (pH 7.0), 150 mM sodium chloride). The UF membranes were flushed with formulation buffer to enhance product recovery. The product concentration was measured and diluted to 10.0 g/L. The diluted material was 0.5/0.2 µm filtered. Polysorbate 80 was added to the diluted pool to achieve a final concentration of 0.02% (w/v) Polysorbate 80.

Table 20 summarizes the critical processing conditions and acceptance criteria and Table 21 summarizes the KPPs and KPAs for the UF/DF step. The step yield was based on $A_{280}$ measurements post-UF/DF and the viral filtration filtrate.

TABLE 19

Buffers used for the UF/DF Formulation

| Process Step | Buffer |
| --- | --- |
| Flush | WFI |
| Sanitization | 0.5M Sodium Hydroxide |
| Equilibration | 10 mM Sodium Phosphate, 150 mM Sodium Chloride, pH 7.0 |
| Diafiltration | |
| Chase | |
| Pool Dilution | |
| Storage | 0.1M Sodium Hydroxide |
| Excipient | 10% (w/v) Polysorbate 80 |

TABLE 20

Critical Processing Conditions for the UF/DF Formulation

| Parameter | NOR | PAR | Designation |
| --- | --- | --- | --- |
| Dilution | Within 1% of calculated volume | Within 3% of calculated volume | CPP |
| 10% (w/v) Polysorbate 80 | 0.19-0.21% (w/v) of diluted UF/DF product | 0.17-0.23% (w/v) of diluted UF/DF product | CPP |
| Un-formulated Drug Substance pH | 6.5-7.5 | | IPC |
| Diluted UF/DF Product Concentration | 9.0-11.0 mg/mL | | IPC |

TABLE 21

Key Processing Conditions for the UF/DF Formulation

| Parameter/Attribute | NOR | PAR | Designation |
| --- | --- | --- | --- |
| Pre-Use Integrity Test | Pass | Pass | KPP |
| Membrane Loading | 100-500 g/m² | 50-600 g/m² | KPP |
| Feed Flux | 240-420 LMH | 180-440 LMH | KPP |
| Transmembrane Pressure | 10-30 psi | 8-35 psi | KPP |
| Temperature | 15-25° C. | 12-30° C. | KPP |
| Fed-Batch Ratio | 1-3 | 1-5 | KPP |
| Concentration At End of UF Target | 13-17 g/L | 12-20 g/L | KPP |
| Diavolumes | 5.5-7.0 | 4.5-7.0 | KPP |
| Unformulated UF/DF Retentate Hold | ≤4 days | ≤6 days | KPP |
| Product Hold (diluted UF/DF product) | ≤7 days | ≤14 days | KPP |
| Step Yield | ≥90% | | KPA |
| Processing Time (start of initial concentration through end of diafiltration) | ≤11.1 hours | | KPA |
| Post-Use NWP | 75-125% of initial | | KPA |
| Diluted UF/DF Pool Bioburden (Pre-filtration) | <10 CFU/10 mL | | KPA |
| Diluted UF/DF Pool Bioburden (Post-filtration) | <3 CFU/10 mL | | KPA |
| Diluted UF/DF Pool Endotoxin (Post-filtration) | <2 EU/mL | | KPA | g. Step 10: Final Filtration, BDS Fill, Storage, and Transportation

The formulated BDS from Step 9 was filtered through 0.5/0.2 μm filter into bioprocess bags. The expected percent yield was ≥90% based on protein mass post-UF/DF and post-fill. After filling was complete, the final filter must have passed filter integrity testing. In the event that that it was determined reprocessing was required, the product could have been pooled into an identical UF/DF retentate vessel and the product could have been reprocessed once into BDS. Reprocessing was not conducted due to bioburden overaction limits. Table 22 summarizes the IPC and acceptance criteria and Table 23 summarizes the KPAs for the drug substance fill step.

TABLE 22

Critical Processing Conditions for the BDS Fill

| Parameter | Acceptable Limit | Designation |
| --- | --- | --- |
| Post-Use Filter Integrity Test | Pass | IPC |

TABLE 23

Key Processing Conditions for the BDS Fill

| Parameter/Attribute | Acceptable Limit | Designation |
| --- | --- | --- |
| Pre-Filtration Bioburden | <10 CFU/10 mL | KPA |
| Yield | ≥90% | KPA |

The BDS was labeled and stored at 2-8° C., and protected from light. The bioprocess containers were securely wrapped and stored in a sealed secondary plastic containment to add protection for the bioprocess container and minimize environmental variations in humidity. Following BDS release for forward processing, the BDS was shipped at 2-8° C. for drug product manufacturing using an active temperature controlled shipper via a combination of surface road transport and air freight shipping.

3. Drug Product Manufacturing

Figure 6:
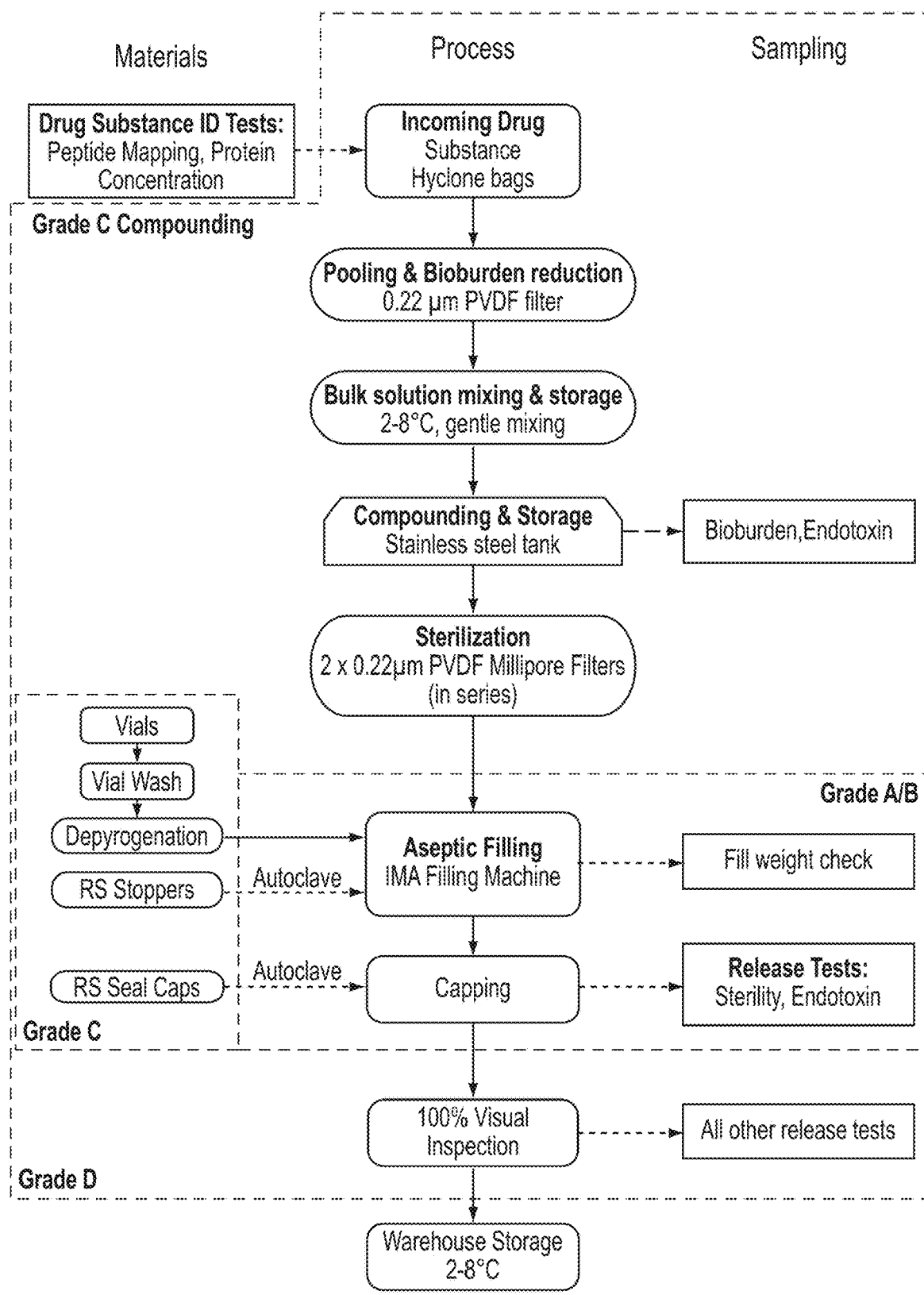
FIG. 6 is a flow diagram of the manufacturing process and controls for ravulizumab drug product.

Ravulizumab drug substance is supplied as an aseptically filled liquid product at a concentration of 10 mg/mL in 100 L disposable bags. The drug product manufacturing begins with pooling of the drug substance through a single 0.22 μm bioburden reduction filter into the compounding vessel. Once the pooling process is complete, the drug substance is sterile filtered and aseptically filled into sterile, depyrogenated vials using an automated filling machine (Filling Line 1). The aseptically filled vials are then stoppered and capped. There are no reprocessing steps or procedures allowed in the ravulizumab drug product manufacturing process. A flow diagram of the manufacturing process and controls for ravulizumab drug product is set forth in FIG. 6.

a. Step 1: Equipment and Component Preparation

Wet component preparation activities were carried out in an ISO 8 (Grade D, Class 100,000) classified area. Dry preparation component activities, including the autoclaving of components, were conducted in an ISO 7 (Grade C, Class 10,000) classified area. Following preparation, sterile wrapped components were stored in ISO 6 (Grade B, Class 1,000) classified area.

Prior to each drug product manufacturing campaign, the stoppering bowl, tracks, pick/place heads, pusher pins and the surge vessel were cleaned out of place (COP) and sterilized in the autoclave.

The Bioburden Filtration and Sterile Filtration Manifold with incorporated filters and the Pooling Manifold were supplied pre-sterilized (gamma irradiated) and were disposable (single use). The sterilizing filters were integrity tested both pre- and post-use, and post-usage testing was carried out on the second filter. The first filter could have been tested post-use if there was a test issue with the second filter. The transfer line between the sterilizing filters was in an ISO 7 (Grade C, Class 10,000) classified area and the surge tank in ISO 5 (Grade A, Class 100) was composed of single use disposable tubing manifold supplied pre-sterilized.

The primary product-contact packaging components include the 30 mL glass vial and the rubber stopper. Prior to the start of filling operations, drug product container closure system components were processed and prepared for use as described below. Cleaning, sterilization and depyrogenation parameters are summarized in Table 24.

Vials were washed in an inverted state through a series of rinsing stations in the vial washer (ISO 7 (Grade C, Class 10,000)). Stations include internal and external rinses with recycled WFI, followed by internal and external rinses with fresh WFI. Filtered clean dry air was used to dry the internal and external vial surfaces prior to reversion and placement on the infeed belt of the depyrogenation tunnel. Vials were transferred to the heating zone, where electrically heated laminar air flowed continuously to depyrogenate the vials. Downstream of the heating zone, the vials entered a cooling zone where the glass temperature was progressively lowered to less than 25° C. Depyrogenated vials were discharged into an ISO 5 (Grade A, Class 100) environment onto an accumulation table that feeds the filling machine.

Bags of stoppers were supplied ready for sterilization and autoclaved on site. The sterilized stoppers were transferred to the filling machine through a transfer port into the stoppering bowl.

The seals were supplied ready for sterilization, autoclaved, brought into the capping and crimping area and loaded into the capping machine. The filling assembly, needle connectors, needles and surge tank were autoclaved and transferred into the ISO 5 (Grade A, Class 100) fill cabinet.

TABLE 24

Cleaning, Sterilization and Depyrogenation Apparatus and Parameters Monitored in Equipment and Component Preparation

| Type | Parameter |
| --- | --- |
| Compounding vessel CIP | Final Rinse Conductivity <2.5 µS/cm @ 80° C. ± 8° C. (Meets EP/USP <645> Water Conductivity Requirements) |
| Compounding vessel SIP | 1.78 Bar @ 123.5 ± 2° C. with an $F_o$ of 30 min |
| Filling and sampling materials autoclave sterilization | 121-124° C. for 35 min (55 min for stoppers) |
| Vial depyrogenation | Temperature Set-Point 290° C. ± 10° C. with an $F_h$ of 30 min Conveyor belt speed of 0 to 85.0 mm/min + 3 mm/min. | b. Step 2: Pooling and Stirring

The drug substance was removed from 2-8° C. storage and transferred to the pooling room (ISO 7, Grade C, Class 10,000). Up to two drug substance batches could have been pooled up to the validated maximum batch size into a single drug product batch.

Each bag was connected to a single use pooling manifold, and the drug substance was pumped one bag at a time by a peristaltic pump through a single 0.22 µm bioburden reduction filter into the 1,000 L stainless steel (316 grade) temperature controlled jacketed compounding tank. The transfer of the drug substance into the tank via peristaltic pump must have been completed within 12 hours of the removal of the drug substance from 2-8° C. storage. The pooled drug substance was mixed at 60 RPM for 30 to 90 minutes and verified that temperature is 2-8° C. before the mixer was turned off.

The drug substance could have been held in the compounding tank for up to 24 hours, at 2-8° C., before beginning sterile filtration and transfer to the filling machine. The process parameters and in-process control for the Pooling and Stirring step are presented in Table 25.

TABLE 25

In-Process Controls for the Pooling/Stirring Step

| Process Control | Test or Operating Parameter | Set-Point or Limit |
| --- | --- | --- |
| Flow rate during pooling | Flow rate | 5 L/min based on peristaltic pump |
| Compounding tank agitation and temperature control | Agitation speed | 60 RPM |
| | Agitation time to reach 2-8° C. | 30 min minimum, up to a maximum of 90 min at 2-8° C. |
| | Temperature of drug substance | |
| Maximum time to transfer from BDS containers into compounding tank | Transfer time limit | ≤12 hours |
| Maximum hold time of drug substance in the compounding tank at 2-8° C. | Hold time limit | ≤24 hours | c. Step 3: Sterile Filtration

Sterile filtration occurred under a closed system in an ISO 7 (Grade C, Class 10,000) classified area. When filling was ready to begin, a sample of the pooled drug substance was taken from the vessel for pre-filtration bioburden and endotoxin testing.

The drug substance was sterile filtered through two sequential hydrophilic 10" absolute 0.22 µm Durapore polyvinylidene fluoride (PVDF) (KVGLG1TTT1) sterilizing grade filters each with a filtration area of 0.73 m². Pressure transfer (Nitrogen vessel set-point target pressure of 0.5 (range 0.2-1.3 Bar)) moved the product from the compounding tank, through the two 0.22 µm filters arranged in series in the compounding room, through irradiated tubing in the ISO 6 (Grade B, Class 1,000) area and into the aseptic filling room (Grade A (RABS)/B (Room)). Both filters were integrity tested wetted with WFI pre-filtration. The second filter, closest to the filling line, was considered the final sterile product filter. This filter was bubble point tested, wetted with WFI, post-filtration. If the second filter failed to meet the integrity test criteria, the first filter was integrity tested with WFI post-use. The process parameters and in-process control for the Sterile Filtration step are presented in Table 26.

The post-use flushing procedure was as follows: Post-sterile filtration, a blowdown with process nitrogen was performed post each filter on the sterile filtration manifold until product was visually removed through to the manifold and onto the Filling Line surge tank. Following this product blowdown, a WFI flush was performed on both filters. Sterilizing filter 1 was initially flushed with 10 L of WFI and then both filters were flushed with 36 L of WFI resulting in a total flush volume of 46 L of WFI. A post-use filter integrity test was then performed on the second filter.

TABLE 26

In-Process Controls for the Sterile Filtration Step

| Process Control | Test or Operating Parameter | Set-Point or Limit |
|---|---|---|
| Pre-Filtration Bioburden | In-Process bioburden | ≤1 CFU/10 mL or ≤10 CFU/100 mL |
| Pre-Filling Endotoxin | In-Process endotoxin | <0.1 EU/mg $A_{280}$ Protein |
| Pre-use Filter Integrity | Bubble Point Test | 3450-4140 mbar |
| Post-use Filter Integrity | Bubble Point Test | 3040-4140 mbar | d. Step 4: Aseptic Filling

All product contact equipment used in the filling process was single use disposable. The sterile filtered drug substance was aseptically filled into sterile, depyrogenated vials using an automated filling machine (Grade A RABS LAF in a Grade B room). Each vial was filled to 32.00±0.96 g based on weight (1.008 g=1.00 mL). Stoppers were then aseptically inserted into the filled vials by the filling machine. 100% in-process monitoring of fill weight was performed throughout the filling step to ensure that the vial fill weight was effectively monitored and controlled. In the event a vial was found outside of the fill weight limits, it was rejected.

During the filling operations, particulates and microbiological monitoring was performed for the ISO 5 environment (Grade A, Class 100 LAF) along with the system controls (e.g., temperature, differential pressure). Additional environmental and personnel monitoring were performed during filling as appropriate as per established procedures. The process parameters and in-process control for the Aseptic Filling step are presented in Table 27.

TABLE 27

In-Process Controls for the Aseptic Filling Step

| Process Control | Fill Volume (mL) | Fill Weight (g) |
|---|---|---|
| Upper Action Limit (+3%) | 32.70 | 32.96 |
| Target | 31.75 | 32.00 |
| Lower Action Limit (−3%) | 30.79 | 31.04 |
| Density | 1.008 g/mL | |
| Filling Speed | ≤40 vials per min | |
| Stopper presence sensor | Pass/Fail | | e. Step 5: Capping

The filled and stoppered vials were conveyed to the capping machine for capping in an ISO 5 (Grade A, Class 100) environment. Vials exited the capping machine into the ISO 8 (Grade D, Class 100,000) environment. The vials had a batch number printed on the seal by the ink jet printer. Filled, sealed and coded vials were loaded into polypropylene boxes. The process parameters and in-process control for the Capping step were presented in Table 28.

TABLE 28

In-Process Controls for the Capping Step

| Process Control | Set-Point or Range |
|---|---|
| Capping Pressure | 0.8-1.2 bar |

The entire Aseptic Filling step, including capping, must have been completed within 24 hours of the start of sterile filtration. The sealed vials were 100% visually inspected for particulates, seal defects, glass and minor defects. Defective vials were removed.

4. Storage and Shipping

The ravulizumab drug product was stored at 2-8° C. The drug product unlabeled vials were packed in a secondary container and transported under temperature controlled conditions for packaging and labeling.

5. Labeling and Secondary Packaging

Vials were labeled using a fully automated labeling machine in a dedicated production room. Prior to secondary packaging, labels, cartons and package inserts (PI) were inspected. Unlabeled vials were removed from 2-8° C. storage and allowed to warm to ambient temperature for the remainder of the labeling and secondary packaging process.

During labeling, a label was applied to the vial and the labeled vial was inserted into a unit carton along with a PI and the carton was closed. Finished unit cartons were sampled at regular intervals and visually and/or electronically inspected. Finished unit cartons were packed into corrugated shippers for subsequent storage at 2-8° C. and shipment to distributors.

6. Ravulizumab Drug Product

Ravulizumab is supplied as a sterile aqueous solution for intravenous administration containing at a concentration of 10 mg/mL in 10 mM sodium phosphate, 150 mM sodium chloride, 0.02% (w/v) Polysorbate 80 in a stoppered 30 mL glass vial.

The quantitative and qualitative composition of the ravulizumab drug product are presented in Table 29. Excipients are tested to the United States Pharmacopeia (USP), European Pharmacopoeia (Ph. Eur.), and/or Japanese Pharmacopeia (JP). The ravulizumab vial content is based on the extractable volume.

TABLE 29

Ravulizumab Drug Product (10 mg/mL) Composition

| Component (Formulation Concentration) | Quality Standard | Function | Amount/vial |
|---|---|---|---|
| Total Fill Volume (mL) | | | 32.0 mL |
| Overfill (mL) | | | 2.0 mL |
| Extractable Volume (mL) | | | 30.0 mL |
| ravulizumab (10 mg/mL) | In-house | Active ingredient | 300 mg |
| 3.34 mM Monobasic sodium phosphate (0.46 mg/mL) | USP, Ph. Eur. | pH buffer | 13.8 mg |
| 6.63 mM Dibasic sodium phosphate (1.78 mg/mL) | USP, Ph. Eur. | pH buffer | 53.4 mg |
| 150 mM Sodium chloride (8.77 mg/mL) | USP, Ph. Eur., JP | Tonicity modifier | 263.1 mg |
| Polysorbate 80 0.02% (w/v) | NF, Ph. Eur., JP | Surfactant | 6.0 mg |
| Water for injection | USP, Ph. Eur., JP | Solvent | Q.S. |

The release and stability specification for ravulizumab drug product is presented in Table 30.

TABLE 30

Ravulizumab Drug Product Specification

| Test | Release and Shelf-Life Acceptance Criteria |
|---|---|
| Appearance | Clear to translucent, slight whitish color, Practically free from particles |
| Osmolality [1] | 273-327 mOsm/kg |
| pH [1] | 6.7-7.3 |

TABLE 30-continued

Ravulizumab Drug Product Specification

| Test | Release and Shelf-Life Acceptance Criteria |
|---|---|
| Protein Concentration ($A_{280}$) | 9.0-11.0 mg/mL |
| Reduced Microchip Capillary Electrophoresis (rCE) | ≥95.0% heavy and light chains, ≤5.0% total impurities |
| Non-Reduced Microchip Capillary Electrophoresis (nrCE) | ≥90.0% IgG main band, ≤10.0% total impurities |
| Imaged Capillary Electrophoresis (iCE) | Comparable to reference standard; all pI bands resolved between 5.5 to 6.8. Main peak ≥50.0%, Acidic group ≤35.0%, Basic group ≤25.0% |
| Peptide Mapping LC | Comparable to reference standard; No new non-reference peaks |
| Size Exclusion Chromatography (SEC-HPLC) | ≥95.0% Monomer ≤5.0% Aggregates |
| C5 Binding [1] | 100 ± 35% Relative Activity |
| Hemolytic Assay | 100 ± 50% Relative Potency to Reference Standard |
| Endotoxin (LAL) | <0.1 EU/mg |
| Sterility | Meets Requirements |
| Container Closure Integrity [2] | Meets Requirements |
| Particulates | ≤6000 per vials for particulates ≥10 μm ≤600 per vials for particulates ≥25 μm |
| Extractable Volume [1] | Not Less Than 30.0 mL/vial |

[1] Release testing only
[2] Stability testing only; to be performed in lieu of sterility testing

Example 2: UF/DF Recovery Strategy for High Concentration Monoclonal Antibody at Manufacturing Scale Ultrafiltration/Diafiltration (UF/DF) is a rapid and efficient method for separation and purification of biomolecules. For the production of highly concentrated monoclonal antibody intermediate solutions in the course of downstream processing, UF is the industry standard in manufacturing scale. UF/DF can be used to concentrate and desalt sample solutions ranging in volume from 10 mL to thousands of liters.

Key challenges associated with UFDF are achieving high end concentrations and reducing both process time and aggregate formation, particularly for therapeutic proteins intended for subcutaneous administration. UF process yields are affected by the system design and the recovery procedure.

The parameters affecting UF/DF recovery were identified by way of the present experiments as (1) recovery chase volume, (2) target bulk concentration, and (3) a ratio referred to herein as "F-factor". F-factor is defined as ratio of system hold-up volume to total retentate volume. Recovery chase is defined as the volume of buffer added to chase remaining product held up in system. System hold-up volumes vary at different manufacturing facilities. This may end up with a more diluted or concentrated product if hold up volume is not considered in the final formulation UF/DF. Table 31 defines key nomenclature.

TABLE 31

Nomenclature

| Abbreviation | Acronym | Definition |
|---|---|---|
| F-Factor | Recovery Factor | Ratio of system hold-up volume to otal retentate volume. |
| $C_a$ | Combined Concentration | Combined concentration of retentate and chase product. |
| $C_c$ | Chase Concentration | Concentration of the recovered chase product. |
| $C_t$ | Target Concentration | Target concentration of the combined retentate and chase product. |
| $V_c$ | Recovery Chase Volume | Volume of buffer added to recover remaining product held-up in system. |

Figure 7:
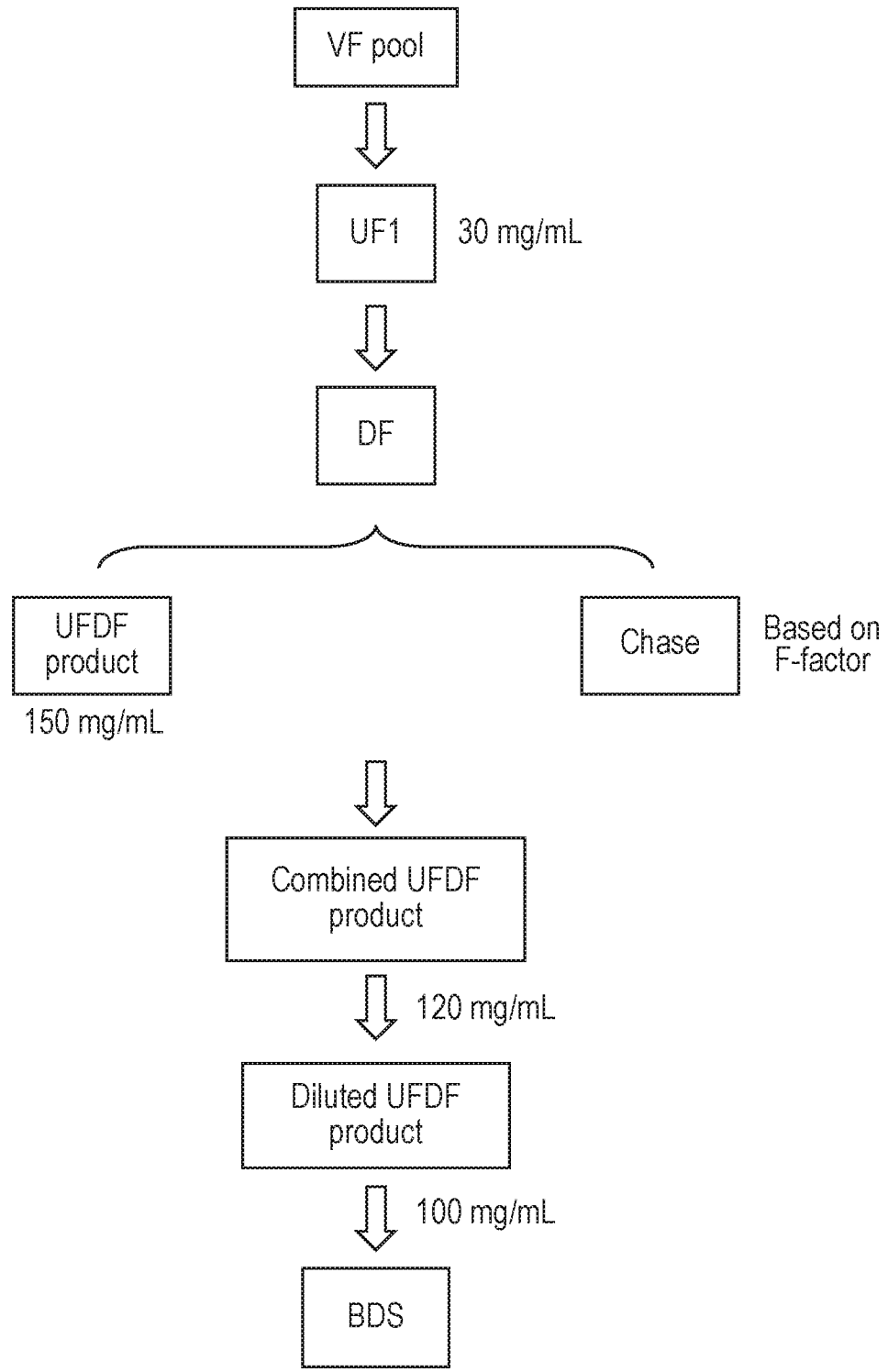
FIG. 7 is schematic of the high concentration ultrafiltration/diafiltration (UF/DF) process used in Example 2.

A full factorial design of experiment (DOE) study was designed using JMP software around these three parameters. From this study specific chase volume for a range of F-factors was defined which can be transferred to any manufacturing facility irrespective of the hold-up volume. The objectives of this study were to: (1) determine a specific chase volume for a range of F-factors that can be transferred to any manufacturing facility, irrespective of the hold-up volume and (2) decrease process time by minimizing the number of in-process $A_{280}$ measurements by developing a robust recovery method. FIG. 7 shows the UF/DF schematic used for this study. 12UF/DF runs were generated in a random order, which included two center point runs as shown in Table 32. The recovery chase was performed as dictated by the DOE design using DF buffer and recirculated for 10 minutes. Weights and concentrations were used to calculate the volume of chase to add to retentate product to target 120 g/L. If the combined product concentration was >125 g/L, dilution was performed using DF buffer to target 120 g/L. A target concentration of 100 g/L was achieved by final excipient addition buffer (EAB).

TABLE 32

UF/DF Recovery DOE Design

| Run No. | Pattern | F factor | Recovery Chase Volume | Target Bulk Concentration (mg/mL) |
|---|---|---|---|---|
| 1 | −++ | 0.2 | 1.1X | 160 |
| 2 | −−− | 0.2 | 0.4X | 140 |
| 3 | −+− | 0.2 | 1.1X | 140 |
| 4 | −−+ | 0.2 | 0.4X | 160 |
| 5 | 000 | 0.5 | 0.75X | 150 |
| 6 | +−− | 0.8 | 0.4X | 140 |
| 7 | ++− | 0.8 | 1.1X | 140 |
| 8 | 000 | 0.5 | 0.75X | 160 |
| 9 | +−+ | 0.8 | 0.4X | 160 |
| 10 | +++ | 0.8 | 1.1X | 150 |
| 11 | +00 | 0.8 | 0.75X | 150 |
| 12 | +−− | 0.8 | 0.1X | 140 |

The critical processing parameters (CPPs) for the 100 mg/mL final UF/DF and formulation were as follows: UFDF product time until excipient addition buffer (EAB) addition (end of final concentration until start of EAB addition)≤16 hours; and EAB addition: 0.1919-0.2393 kg EAB/kg diluted UFDF product.

The key processing parameters (KPP) were as follows:
Pre-use membrane integrity test;
Membrane load (g/m$^2$);
Feed flow rate (LMH);
TMP (psi);

Temperature (C);
Fed-batch ratio;
Initial concentration target (40-60 g/L);
Final concentration target (140-160 g/L);
Diavolumes (4.5-7.5);
Undiluted UF/DF product hold (≤24 hours); and
Diluted UF/DF product hold (≤24 hours).
The specific unit operation details were as follows:
Filter: Millipore Pellicon 3 Ultracel C screen 30 kDa MWCO;
Flush: WFI≥20 L/m$^2$;
Equilibrium: 50 mM NaPO$_4$ (pH 7.4), 25 mM L-Arg (≥20 L/m$^2$);
Membrane load: ≤600 L/m$^2$;
Initial concentration: 40-60 g/L;
Feed flow rate (all product steps): target 360 LMH;
Transmembrane pressure (all product steps): target 15 psi;
Feed pressure: ≤50 psi (can be increased);
DF Buffer: same as equilibrium;
Diavolumes: 4.5-7.5 (Target 6.0);
Final concentration to 140-160 g/L (includes 1.07 recovery factor);
Final concentration may be controlled by feed pressure (not TMP or Feed Flow Rate);
Temperature: 15-35° C.;
Recovery with ≤1× system hold-up volume (calculation required per CSD);
Dilution to target 120 g/L with DF/equilibrium buffer;
0.1919-0.2393 kg/kg addition of excipient addition buffer (EAB—50 mM NaPO$_4$ (pH 7.4), 25 mM L-Arg, 30% Sucrose 0.30% (w/v), PS 80) to 120 g/L UF/DF product for final formulation;
Membrane re-use: Up to 20 cycles;
Sanitization: 0.5 M NaOH;
Storage: 0.1 M NaOH;
Yield: >60% (expected over 90%);
Express SHC filterability 120 g/L UF/DF product: ≤40 L/m$^2$; and
Express SHC filterability BDS: ≤3045 L/m$^2$ (please "right-size" filter to minimize product loss).

Additional experiments were performed to determine the change in buffer chase concentration with incremental buffer volume additions for an UF/DF evaluation at 0.2 F-factor and target bulk concentration of 150 g/L. The buffer volume and concentration data is shown in Table 33 and FIG. 8. A linear regression was fit to the data and the slope and y-intercept was calculated.

TABLE 33

Buffer Chase Volume/Concentration Data (0.2 F Factor)

| Target Bulk Concentration (C$_t$) [g/L] | Target F Factor (F) | Target Buffer Chase Volume (V$_c$) | Buffer Chase Conc. (C$_c$) [g/L] |
|---|---|---|---|
| 150 | 0.2 | 0.4X | 120.3 |
| 150 | 0.2 | 0.6X | 112.5 |
| 150 | 0.2 | 0.8X | 91.5 |
| 150 | 0.2 | 1.0X | 90.0 |

The target concentration for multivariate runs with 0.8 F-factor and buffer chase volumes 0.4 and 1.1× were 140 and 160 g/L. An average of buffer chase concentration (C$_c$) and combined retentate and chase concentration (C$_a$) was performed to provide the theoretical concentrations at 150 g/L. The individual data points and averaged data used to calculate are shown in Table 34 and Table 35. The averaged 0.8 F-factor and DOE Experiment 11 data was used to construct a cohesive data set of buffer chase volumes related to buffer chase concentration as shown in Table 36 and FIG. 9.

TABLE 34

Concentration Data for 0.8 F Factor and 0.4X Chase

| Target Bulk Concentration (C$_t$) [g/L] | Target F Factor (F) | Target Buffer Chase Volume (V$_c$) | Buffer Chase Conc. (C$_c$) [g/L] |
|---|---|---|---|
| 140 | 0.8 | 0.4 | 99.5 |
| 160 | 0.8 | 0.4 | 121.7 |
| Average Buffer Chase Conc. (C$_c$) @ 150 g/L | | | 110.6 |

TABLE 35

Concentration Data for 0.8 F Factor and 1.1X Chase

| Target Bulk Concentration (C$_t$) [g/L] | Target F Factor (F) | Target Buffer Chase Volume (V$_c$) | Buffer Chase Conc. (C$_c$) [g/L] |
|---|---|---|---|
| 140 | 0.8 | 1.1 | 74.0 |
| 160 | 0.8 | 1.1 | 84.4 |
| Average Buffer Chase Conc. (C$_c$) @ 150 g/L | | | 79.2 |

TABLE 36

Buffer Chase Volume/Concentration Data (0.8 F Factor)

| Target Bulk Concentration (C$_t$) [g/L] | Target F Factor (F) | Target Buffer Chase Volume (V$_c$) | Buffer Chase Conc. (C$_c$) [g/L] |
|---|---|---|---|
| 150 | 0.8 | 0.4 | 110.6 |
| 150 | 0.8 | 0.75 | 93.7 |
| 150 | 0.8 | 1.1 | 79.2 |

Figure 8:
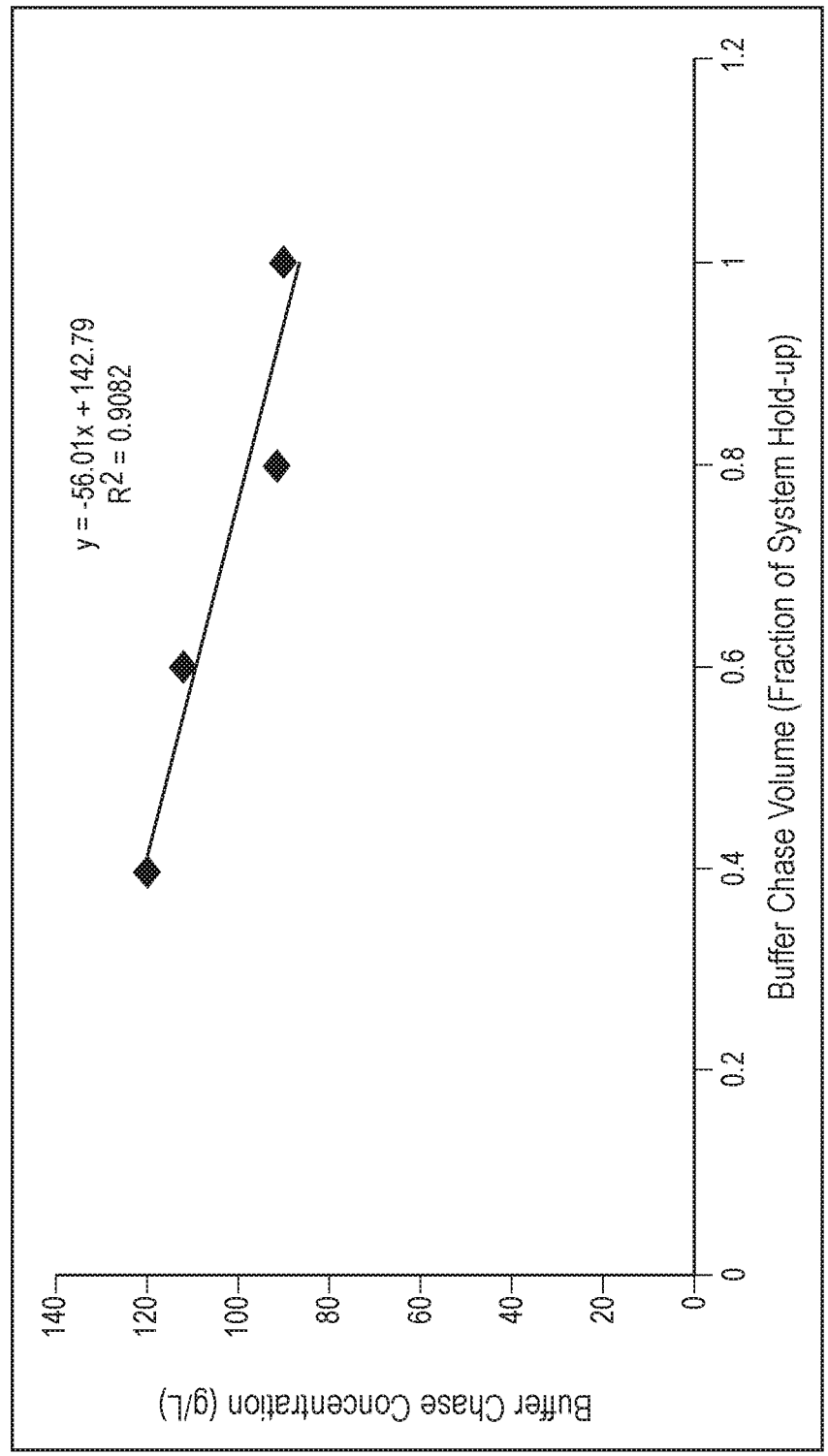
FIG. 8 is a plot of the Buffer Chase Volume vs. Concentration (0.2 F Factor).
Figure 9:
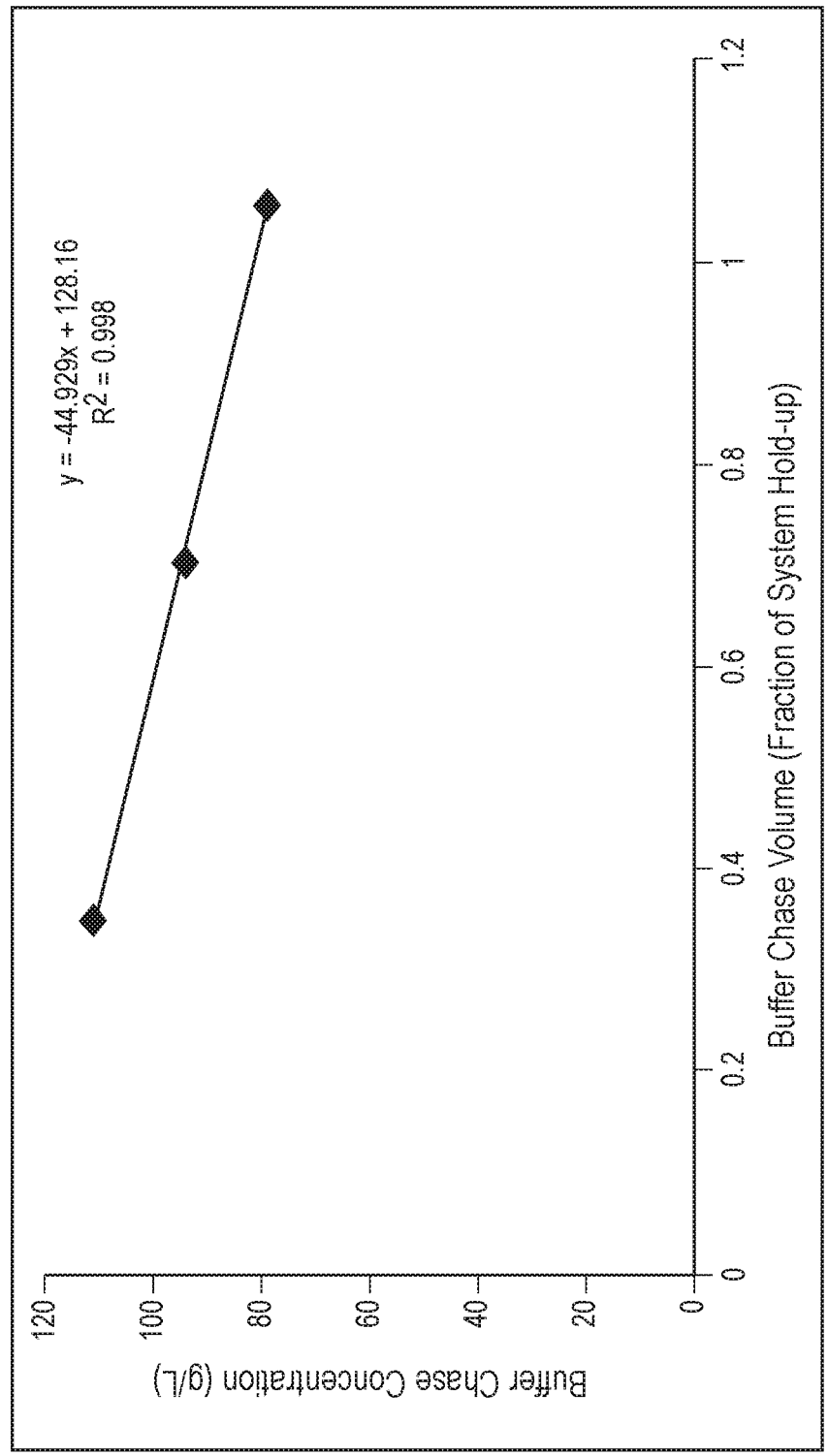
FIG. 9 is a plot of the Buffer Chase Volume vs. Concentration (0.8 F Factor).
Figure 10:
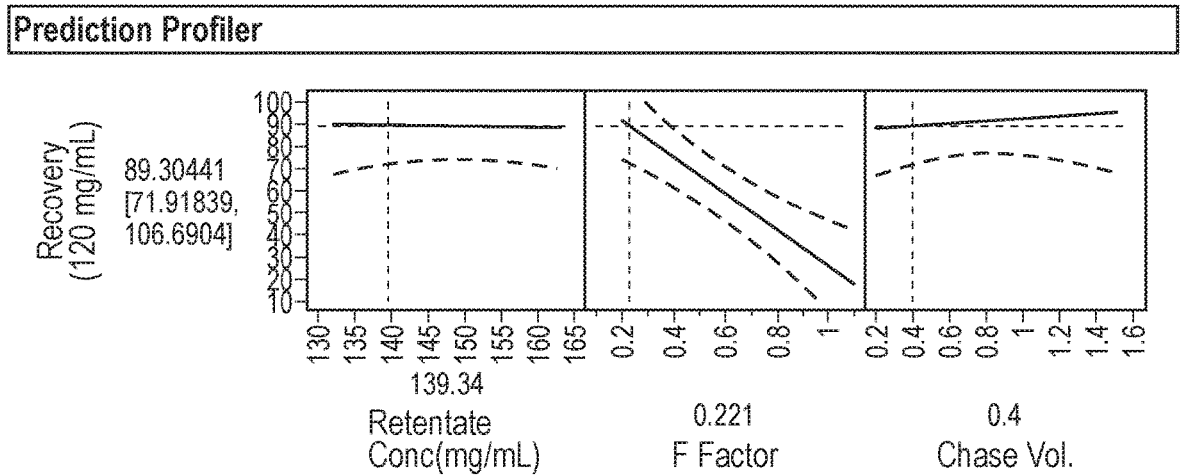
FIG. 10 sets for the prediction profiled for design of experiment (DOE) 2 using JMP software.
Figure 10:
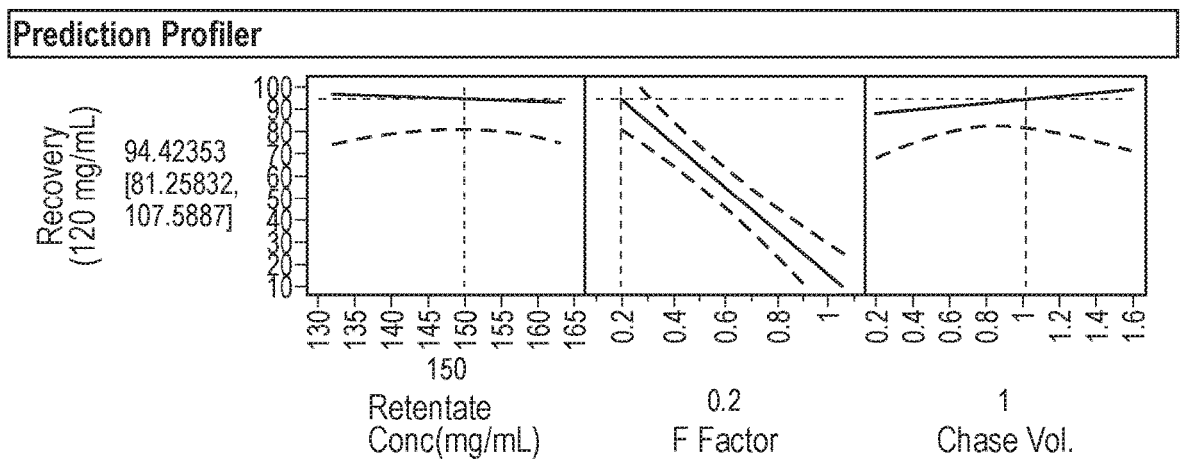

The Slopes and y-intercepts from FIG. 8 and FIG. 9 were averaged to provide a linear expression that could be applied across an F Factor range of 0.2-0.8 (see Table 37).

TABLE 37

Averaged Slopes and Y-Intercepts

| F-factor (F) | Slope | Y-Intercept |
|---|---|---|
| 0.2 | −56.01 | 142.79 |
| 0.8 | −44.93 | 128.16 |
| Average | −50.47 | 135.48 |

The process recovery was defined as the yield after combining the retentate and buffer chase products. The recovery data from the multivariate study is provided in Table 32. These data indicate that the F-factor and the chase volume are significant factors impacting process recovery. FIG. 9 shows the prediction profiler where DOE Experiment 02 was used an example. F-factors evaluated at 0.2-0.3 with a target bulk concentration of 140 and 160 g/L, and chase volumes 0.4-1.1× provided 87.2-91.7% yield. These data indicate that F-factors within 0.2-0.3 allow for a broader recovery chase strategy irrespective of the retentate product concentration. As the F-factor increases to ~0.9, however, the retentate concentration and buffer chase volume become significant to process recovery (Table 38).

TABLE 38

Recovery DOE Data

| DOE Pattern | TFF Run ID | Retentate Product Conc. (g/L) | F Factor | Buffer Chase Vol. | Process Recovery [120 g/L product] (%) |
|---|---|---|---|---|---|
| −++ | DOE 01 | 163.0 | 0.28 | 1.1X | 89.7 |
| −−− | DOE 02 | 139.3 | 0.22 | 0.4X | 90.3 |
| −+− | DOE 03 | 139.9 | 0.22 | 1.1X | 91.7 |
| −−+ | DOE 04 | 160.7 | 0.27 | 0.4X | 87.2 |
| 000 | DOE 05 | 152.0 | 0.58 | 0.75X | 70.8 |
| +−− | DOE 06 | 130.4 | 0.83 | 0.4X | 22.0 |
| ++− | DOE 07 | 144.2 | 0.89 | 1.1X | 12.9 |
| 000 | DOE 08 | 159.0 | 0.58 | 0.75X | 78.2 |
| +−+ | DOE 09 | 161.7 | 0.90 | 0.4X | 92.0 |
| +++ | DOE 10 | 150.1 | 0.89 | 1.1X | 12.5 |
| +00 | DOE 11 | 152.7 | 0.91 | 0.75X | 14.0 |
| +−− | DOE 12 | 139.2 | 0.78 | 0.1X | 90.8 |

A model was developed using this data set and Equation 1 for predicting the acceptable chase volume range for a given F-factor to ensure ≥120 g/L and 90% process recovery. F-factors were evaluated from 0.1-0.9, buffer chase volumes from 0.1-1.6×, and retentate concentration maintained at 140 g/L to account for the worst case concentration result. The theoretical diluted UF/DF product concentrations for each F-factor and buffer chase volume is provided in Table 38. F factor and buffer chase volume conditions that resulted in ≥120 g/L are in bold and values <120 g/L are underlined to clearly identify acceptable and non-acceptable conditions. Results from the study were used to group the F-factors into three levels and provide corresponding buffer chase volume ranges for ease of batch record implementation. Manufacturing control strategy was implemented from this study.

TABLE 39

Theoretical Diluted UF/DF Product Concentrations

| F Factor | 0.1X | 0.2X | 0.3X | 0.4X | 0.5X | 0.6X | 0.7X | 0.8X | 0.9X | 1X | 1.1X |
|---|---|---|---|---|---|---|---|---|---|---|---|
| 0.1 | 139.0 | 138.3 | 137.5 | 136.7 | 135.7 | 134.7 | 133.7 | 132.5 | 131.3 | 130.0 | 128.6 |
| 0.2 | 137.9 | 136.6 | 135.2 | 133.6 | 131.9 | 130.1 | 128.1 | 126.1 | 123.9 | 121.7 | 119.3 |
| 0.3 | 136.9 | 135.0 | 133.0 | 130.7 | 128.4 | 125.8 | 123.2 | 120.4 | 117.6 | 114.6 | 111.6 |
| 0.4 | 136.0 | 133.5 | 130.9 | 128.1 | 125.1 | 122.0 | 118.8 | 115.5 | 112.1 | 108.6 | 105.0 |
| 0.5 | 135.0 | 132.0 | 128.9 | 125.6 | 122.1 | 118.6 | 114.9 | 111.1 | 107.3 | 103.3 | 99.3 |
| 0.6 | 134.0 | 130.6 | 127.0 | 123.3 | 119.4 | 115.4 | 111.4 | 107.2 | 103.0 | 98.8 | 94.4 |
| 0.7 | 133.1 | 129.2 | 125.2 | 121.1 | 116.9 | 112.6 | 108.2 | 103.7 | 99.2 | 94.7 | 90.1 |
| 0.8 | 132.2 | 127.9 | 123.5 | 119.0 | 114.5 | 109.9 | 105.3 | 100.6 | 95.9 | 91.1 | 86.3 |
| 0.9 | 131.3 | 126.6 | 121.9 | 117.1 | 112.3 | 107.5 | 102.6 | 97.7 | 92.8 | 87.9 | 83.0 |

In conclusion, the F Factor and buffer chase volume UF/DF parameters were classified as KPPs. Table 35 was used to group the F-factors into three levels and provide corresponding buffer chase volume ranges for ease of batch record implementation at CMOs. This eliminated the $A_{280}$ measurements of individual UF/DF product and Chase. Eliminating the $A_{280}$ measurements at these two steps decreased the total UF/DF processing time, which helps in maintaining the product stability.

SEQUENCE SUMMARY

SEQ ID NO: 1
GYIFSNYWIQ

SEQ ID NO: 2
EILPGSGSTEYTENFKD

SEQ ID NO: 3
YFFGSSPNWYFDV

SEQ ID NO: 4
GASENIYGALN

SEQ ID NO: 5
GATNLAD

SEQUENCE SUMMARY

SEQ ID NO: 6
QNVLNTPLT

SEQ ID NO: 7
QVQLVQSGAE VKKPGASVKV SCKASGYIFS NYWIQWVRQA PGQGLEWMGE ILPGSGSTEY
TENFKDRVTM TRDTSTSTVY MELSSLRSED TAVYYCARYF FGSSPNWYFD VWGQGTLVTV
SS

SEQ ID NO: 8
DIQMTQSPSS LSASVGDRVT ITCGASENIY GALNWYQQKP GKAPKLLIYG ATNLADGVPS
RFSGSGSGTD FTLTISSLQP EDFATYYCQN VLNTPLTFGQ GTKVEIK

SEQ ID NO: 9
ASTKGPSVFP LAPCSRSTSE STAALGCLVK DYFPEPVTVS WNSGALTSGV HTFPAVLQSS
GLYSLSSVVT VPSSNFGTQT YTCNVDHKPS NTKVDKTVER KCCVECPPCP APPVAGPSVF
LFPPKPKDTL MISRTPEVTC VVVDVSQEDP EVQFNWYVDG VEVHNAKTKP REEQFNSTYR
VVSVLTVLHQ DWLNGKEYKC KVSNKGLPSS IEKTISKAKG QPREPQVYTL PPSQEEMTKN
QVSLTCLVKG FYPSDIAVEW ESNGQPENNY KTTPPVLDSD GSFFLYSRLT VDKSRWQEGN
VFSCSVMHEA LHNHYTQKSL SLSLGK

SEQ ID NO: 10
QVQLVQSGAE VKKPGASVKV SCKASGYIFS NYWIQWVRQA PGQGLEWMGE ILPGSGSTEY
TENFKDRVTM TRDTSTSTVY MELSSLRSED TAVYYCAR YFFGSSPNWY FDVWGQGTLV
TVSSASTKGP SVFPLAPCSR STSESTAALG CLVKDYFPEP VTVSWNSGAL TSGVHTFPAV
LQSSGLYSLS SVVTVPSSNF GTQTYTCNVD HKPSNTKVDK TVERKCCVEC PPCPAPPVAG
PSVFLFPPKP KDTLMISRTP EVTCVVVDVS QEDPEVQFNW YVDGVEVHNA KTKPREEQFN
STYRVVSVLT VLHQDWLNGK EYKCKVSNKG LPSSIEKTIS KAKGQPREPQ VYTLPPSQEE
MTKNQVSLTC LVKGFYPSDI AVEWESNGQP ENNYKTTPPV LDSDGSFFLY SRLTVDKSRW
QEGNVFSCSV MHEALHNHYT QKSLSLSLGK

SEQ ID NO: 11
DIQMTQSPSS LSASVGDRVT ITCGASENIY GALNWYQQKP GKAPKLLIYG ATNLADGVPS
RFSGSGSGTD FTLTISSLQP EDFATYYCQN VLNTPLTFGQ GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC

SEQ ID NO: 12
QVQLVQSGAE VKKPGASVKV SCKASGHIFS NYWIQWVRQA PGQGLEWMGE ILPGSGHTEY
TENFKDRVTM TRDTSTSTVY MELSSLRSED TAVYYCARYF FGSSPNWYFD VWGQGTLVTV
SS

SEQ ID NO: 13
ASTKGPSVFP LAPCSRSTSE STAALGCLVK DYFPEPVTVS WNSGALTSGV HTFPAVLQSS
GLYSLSSVVT VPSSNFGTQT YTCNVDHKPS NTKVDKTVER KCCVECPPCP APPVAGPSVF
LFPPKPKDTL MISRTPEVTC VVVDVSQEDP EVQFNWYVDG VEVHNAKTKP REEQFNSTYR
VVSVLTVLHQ DWLNGKEYKC KVSNKGLPSS IEKTISKAKG QPREPQVYTL PPSQEEMTKN
QVSLTCLVKG FYPSDIAVEW ESNGQPENNY KTTPPVLDSD GSFFLYSRLT VDKSRWQEGN
VFSCSVLHEA LHSHYTQKSL SLSLGK

SEQ ID NO: 14
QVQLVQSGAE VKKPGASVKV SCKASGHIFS NYWIQWVRQA PGQGLEWMGE ILPGSGHTEY
TENFKDRVTM TRDTSTSTVY MELSSLRSED TAVYYCARYF FGSSPNWYFD VWGQGTLVTV
SSASTKGPSV FPLAPCSRST SESTAALGCL VKDYFPEPVT VSWNSGALTS GVHTFPAVLQ
SSGLYSLSSV VTVPSSNFGT QTYTCNVDHK PSNTKVDKTV ERKCCVECPP CPAPPVAGPS
VFLFPPKPKD TLMISRTPEV TCVVVDVSQE DPEVQFNWYV DGVEVHNAKT KPREEQFNST
YRVVSVLTVL HQDWLNGKEY KCKVSNKGLP SSIEKTISKA KGQPREPQVY TLPPSQEEMT
KNQVSLTCLV KGFYPSDIAV EWESNGQPEN NYKTTPPVLD SDGSFFLYSR LTVDKSRWQE
GNVFSCSVLH EALHSHYTQK SLSLSLGK

SEQ ID NO: 15
ASTKGPSVFP LAPCSRSTSE STAALGCLVK DYFPEPVTVS WNSGALTSGV HTFPAVLQSS
GLYSLSSVVT VTSSNFGTQT YTCNVDHKPS NTKVDKTVER KCCVECPPCP APPVAGPSVF
LFPPKPKDTL YITREPEVTC VVVDVSHEDP EVQFNWYVDG MEVHNAKTKP REEQFNSTFR
VVSVLTVVHQ DWLNGKEYKC KVSNKGLPAP IEKTISKTKG QPREPQVYTL PPSREEMTKN
QVSLTCLVKG FYPSDIAVEW ESNGQPENNY KTTPPMLDSD GSFFLYSKLT VDKSRWQQGN
VFSCSVMHEA LHNHYTQKSL SLSPGK

SEQ ID NO: 16
QVQLVQSGAE VKKPGASVKV SCKASGYIFS NYWIQWVRQA PGQGLEWMGE ILPGSGSTEY
TENFKDRVTM TRDTSTSTVY MELSSLRSED TAVYYCARYF FGSSPNWYFD VWGQGTLVTV
SSASTKGPSV FPLAPCSRST SESTAALGCL VKDYFPEPVT VSWNSGALTS GVHTFPAVLQ
SSGLYSLSSV VTVTSSNFGT QTYTCNVDHK PSNTKVDKTV ERKCCVECPP CPAPPVAGPS
VFLFPPKPKD TLYITREPEV TCVVVDVSHE DPEVQFNWYV DGMEVHNAKT KPREEQFNST
FRVVSVLTVV HQDWLNGKEY KCKVSNKGLP APIEKTISKT KGQPREPQVY TLPPSREEMT
KNQVSLTCLV KGFYPSDIAV EWESNGQPEN NYKTTPPMLD SDGSFFLYSK LTVDKSRWQQ
GNVFSCSVMH EALHNHYTQK SLSLSPGK

SEQUENCE SUMMARY

SEQ ID NO: 17
GASENIYHALN

SEQ ID NO: 18
EILPGSGHTEYTENFKD

SEQ ID NO: 19
GHIFSNYWIQ

SEQ ID NO: 20
QVQLVQSGAE VKKPGASVKV SCKASGHIFS NYWIQWVRQA PGQGLEWMGE ILPGSGHTEY
TENFKDRVTM TRDTSTSTVY MELSSLRSED TAVYYCARYF FGSSPNWYFD VWGQGTLVTV
SSASTKGPSV FPLAPCSRST SESTAALGCL VKDYFPEPVT VSWNSGALTS GVHTFPAVLQ
SSGLYSLSSV VTVPSSNFGT QTYTCNVDHK PSNTKVDKTV ERKCCVECPP CPAPPVAGPS
VFLFPPKPKD TLMISRTPEV TCVVVDVSQE DPEVQFNWYV DGVEVHNAKT KPREEQFNST
YRVVSVLTVL HQDWLNGKEY KCKVSNKGLP SSIEKTISKA KGQPREPQVY TLPPSQEEMT
KNQVSLTCLV KGFYPSDIAV EWESNGQPEN NYKTTPPVLD SDGSFFLYSR LTVDKSRWQE
GNVFSCSVMH EALHNHYTQK SLSLSLGK

SEQ ID NO: 21
SYAIS

SEQ ID NO: 22
GIGPFFGTANYAQKFQG

SEQ ID NO: 23
DTPYFDY

SEQ ID NO: 24
SGDSIPNYYVY

SEQ ID NO: 25
DDSNRPS

SEQ ID NO: 26
QSFDSSLNAEV

SEQ ID NO: 27
QVQLVQSGAE VKKPGSSVKV SCKASGGTFS SYAISVWRQA PGQGLEWMGG IGPFFGTANY
AQKFQGRVTI TADESTSTAY MELSSLRSED TAVYYCARDT PYFDYWGQGT LVTVSS

SEQ ID NO: 28
DIELTQPPSV SVAPGQTARI SCSGDSIPNY YVYWYQQKPG QAPVLVIYDD SNRPSGIPER
FSGSNSGNTA TLTISGTQAE DEADYYCQSF DSSLNAEVFG GGTKLTVL

SEQ ID NO: 29
NYIS

SEQ ID NO: 30
IIDPDDSYTEYSPSFQG

SEQ ID NO: 31
YEYGGFDI

SEQ ID NO: 32
SGDNIGNSYVH

SEQ ID NO: 33
KDNDRPS

SEQ ID NO: 34
GTYDIESYV

SEQ ID NO: 35
EVQLVQSGAE VKKPGESLKI SCKGSGYSFT NYISWVRQMP GKGLEWMGII DPDDSYTEYS
PSFQGQVTIS ADKSISTAYL QWSSLKASDT AMYYCARYEY GGFDIWGQGT LVTVSS

SEQ ID NO: 36
SYELTQPPSV SVAPGQTARI SCSGDNIGNS YVHWYQQKPG QAPVLVIYKD NDRPSGIPER
FSGSNSGNTA TLTISGTQAE DEADYYCGTY DIESYVFGGG TKLTVL

SEQ ID NO: 37
SSYYVA

SEQ ID NO: 38
AIYTGSGATYKASWAKG

SEQUENCE SUMMARY

SEQ ID NO: 39
DGGYDYPTHAMHY

SEQ ID NO: 40
QASQNIGSSLA

SEQ ID NO: 41
GASKTHS

SEQ ID NO: 42
QSTKVGSSYGNH

SEQ ID NO: 43
QVQLVESGGG LVQPGGSLRL SCAASGFTSH SSYYVAWVRQ APGKGLEWVG AIYTGSGATY
KASWAKGRFT ISKDTSKNQV VLTMTNMDPV DTATYYCASD GGYDYPTHAM HYWGQGTLVT
VSS

SEQ ID NO: 44
DVVMTQSPSS LSASVGDRVT ITCQASQNIG SSLAWYQQKP GQAPRLLIYG ASKTHSGVPS
RFSGSGSGTD FTLTISSLQP EDVATYYCQS TKVGSSYGNH FGGGTKVEIK

SEQ ID NO: 45
QVQLVESGGG LVQPGRSLRL SCAASGFTVH SSYYMAWVRQ APGKGLEWVG AIFTGSGAEY
KAEWAKGRVT ISKDTSKNQV VLTMTNMDPV DTATYYCASD AGYDYPTHAM HYWGQGTLVT
VSSASTKGPS VFPLAPSSKS TSGGTAALGC LVKDYFPEPV TVSWNSGALT SGVHTFPAVL
QSSGLYSLSS VVTVPSSSLG TQTYICNVNH KPSNTKVDKK VEPKSCDKTH TCPPCPAPEL
RRGPKVFLFP PKPKDTLMIS RTPEVTCVVV DVSHEDPEVK FNWYVDGVEV HNAKTKPREE
QYNSTYRVVS VLTVLHQDWL NGKEYKCKVS NKGLPSSIEK TISKAKGQPR EPQVYTLPPS
REEMTKNQVS LTCLVKGFYP SDIAVEWESN GQPENNYKTT PPVLDSDGSF FLYSKLTVDK
SRWQQGNVFS CSVLHEALHA HYTRKELSLS P

SEQ ID NO: 46
DIQMTQSPSS LSASVGDRVT ITCRASQGIS SSLAWYQQKP GKAPKLLIYG ASETESGVPS
RFSGSGSGTD FTLTISSLQP EDFATYYCQN TKVGSSYGNT FGGGTKVEIK RTVAAPSVFI
FPPSDEQLKS GTASVVCLLN NFYPREAKVQ WKVDNALQSG NSQESVTEQD SKDSTYSLSS
TLTLSKADYE KHKVYACEVT HQGLSSPVTK SFNRGEC

SEQ ID NO: 47
QVQLQESGPG LVKPSETLSL TCTVSGDSVS SSYWTWIRQP PGKGLEWIGY IYYSGSSNYN
PSLKSRATIS VDTSKNQFSL KLSSVTAADT AVYYCAREGN VDTTMIFDYW GQGTLVTVSS

SEQ ID NO: 48
AIQMTQSPSS LSASVGDRVT ITCRASQGIR NDLGWYQQKP GKAPKLLIYA ASSLQSGVPS
RFAGRGSGTD FTLTISSLQP EDFATYYCLQ DFNYPWTFGQ GTKVEIK

SEQ ID NO: 49
QVQLQESGPG LVKPSETLSL TCTVSGDSVS SSYWTWIRQP PGKGLEWIGY IYYSGSSNYN
PSLKSRATIS VDTSKNQFSL KLSSVTAADT AVYYCAREGN VDTTMIFDYW GQGTLVTVSS
ASTKGPSVFP LAPCSRSTSE STAALGCLVK DYFPEPVTVS WNSGALTSGV HTFPAVLSSS
GLYSLSSVVT VPSSSLGTKT YTCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTVLH QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK

SEQ ID NO: 50
AIQMTQSPSS LSASVGDRVT ITCRASQGIR NDLGWYQQKP GKAPKLLIYA ASSLQSGVPS
RFAGRGSGTD FTLTISSLQP EDFATYYCLQ DFNYPWTFGQ GTKVEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC

What is claimed is:

1. A method of producing an anti-C5 antibody, wherein the method comprises
   a. culturing mammalian cells comprising a nucleic acid encoding the anti-C5 antibody in a cell culture production medium, such that the anti-C5 antibody is produced in said cell culture production medium;
   b. a recovery step comprising filtering the cell culture production medium through a depth filter;
   c. purification by Protein A affinity chromatography;
   d. a low pH viral inactivation step;
   e. purification by cation exchange chromatography;
   f. purification by anion exchange chromatography;
   g. a virus reduction filtration step; and
   h. a concentration and diafiltration step, wherein the concentration and diafiltration step involves using a polysorbate 80 buffer,
   wherein the anti-C5 antibody comprises CDR1, CDR2 and CDR3 heavy chain sequences as set forth in SEQ ID NOs: 19, 18 and 3, respectively, and CDR1, CDR2 and CDR3 light chain sequences as set forth in SEQ ID NOs: 4, 5 and 6, respectively, and
   wherein steps a. to h. are performed sequentially in order.

2. The method of claim 1, wherein the anti-C5 antibody:
   (a) comprises the heavy chain variable region set forth in SEQ ID NO:12 and the light chain variable region set forth in SEQ ID NO:8;
   (b) comprises a heavy chain constant region set forth in SEQ ID NO:13;
   (c) comprises a heavy chain polypeptide comprising the amino acid sequence set forth in SEQ ID NO:14 and a light chain polypeptide comprising the amino acid sequence set forth in SEQ ID NO:11;
   (d) binds to human C5 at pH 7.4 and 25° C. with an affinity dissociation constant (KD) that is in the range 0.1 nM≤KD≤1 nM;
   (e) binds to human C5 at pH 6.0 and 25° C. with a $K_D \geq 10$ nM; and/or
   (f) is ravulizumab.

3. The method of claim 1, wherein the depth filter is a two-step depth filtration train.

4. The method of claim 1, wherein processing conditions for the recovery step include one or more of the following:
   a. a D0HC depth filter load of ≤100 L/m² in the Normal Operating Range and ≤100 L/m² in the Proven Acceptable Range;
   b. an A1HC depth filter load of ≤200 L/m² in the Normal Operating Range and ≤200 L/m² in the Proven Acceptable Range;
   c. a 0.5/0.2 µm filter load of ≤800 L/m² in the Normal Operating Range and ≤800 L/m² in the Proven Acceptable Range;
   d. a harvest load temperature of 18°-37° C. in the Normal Operating Range and 15-37° C. in the Proven Acceptable Range;
   e. a buffer chase volume of 20-25 L/m² in the Normal Operating Range and 0-30 L/m² in the Proven Acceptable Range;
   f. a clarified harvest hold time of ≤10 Days in the Normal Operating Range and ≤16 Days in the Proven Acceptable Range;
   g. a yield of ≥70%;
   h. a total filtration time of <3.3 hours;
   i. a bioburden of <3 CFU/10 mL; and/or
   j. an endotoxin of <5 EU/mL.

5. The method of claim 1, wherein the Protein A affinity chromatography is Protein A affinity chromatography with modified resin, and wherein the Protein A affinity chromatography with modified resin comprises one or more buffers selected from the group consisting of:
   a. 0.1 N sodium hydroxide for sanitization;
   b. 20 mM Tris and 65 mM sodium chloride at a pH of 7.6 for equilibration and Post-Load Wash 1;
   c. 50 mM sodium phosphate, 100 mM sodium chloride, and 300 mM arginine hydrochloride at a pH of 6.0 for Post-Load Wash 2;
   d. 20 mM Tris and 65 mM sodium chloride at a pH of 7.6 for Post-Load Wash 3;
   e. 25 mM sodium acetate at a pH of 3.75 for elution;
   f. 100 mM acetic acid for stripping;
   g. Water For Injection (WFI) for flushing; and/or
   h. 20% ethanol for storage.

6. The method of claim 1, wherein processing conditions for the Protein A affinity chromatography include one or more of the following:
   a. a pre-batch sanitization hold time of 30-60 minutes in the Normal Operating Range and 30-75 minutes in the Proven Acceptable Range;
   b. a post-batch sanitization hold time of 30-60 minutes in the Normal Operating Range and 30-75 minutes in the Proven Acceptable Range;
   c. column cycles of ≤100 in the Normal Operating Range and ≤100 in the Proven Acceptable Range;
   d. an eluate hold time of ≤7 days in the Normal Operating Range and ≤10 days in the Proven Acceptable Range;
   e. a step yield of ≥70%;
   f. an eluate pre-filtration bioburden of <50 CFU/10 mL;
   g. an eluate post-filtration bioburden of <3 CFU/10 mL; and/or
   h. an eluate post-filtration endotoxin of <5 EU/mL.

7. The method of claim 1, wherein the low pH viral inactivation step comprises subjecting an eluated pool from the Protein A affinity chromatography purification step to low pH conditions.

8. The method of claim 7, wherein the low pH is within a range of 3.60-3.70.

9. The method of claim 7, wherein the method includes treating the eluted pool with acetic acid.

10. The method of claim 1, wherein processing conditions for the low pH viral inactivation step include one or more of the following:
   a. an acidification pH immediately after titration of 3.60-3.70 in the Normal Operating Range and 3.55-3.80 in the Proven Acceptable Range;
   b. an acidification pH immediately after hold time of 3.60-3.75 in the Normal Operating Range and 3.55-3.80 in the Proven Acceptable Range;
   c. a hold time at low pH of 60-120 minutes in the Normal Operating Range and ≥60-360 minutes in the Proven Acceptable Range;
   d. a hold time at neutralized pH prior to 0.5/0.2 μm filtration of 60-120 minutes in the Normal Operating Range and ≥60 minutes in the Proven Acceptable Range;
   e. a filtered neutralized product hold time of ≤7 days in the Normal Operating Range and ≤7 days in the Proven Acceptable Range;
   f. a yield of ≥90%;
   g. a neutralized pre-filtration pool bioburden of <50 CFU/10 mL;
   h. a neutralized post-filtration pool bioburden of <3 CFU/10 mL; and/or
   i. a neutralized post-filtration pool endotoxin of <5 EU/mL.

11. The method of claim 1, wherein neutralized filtrate from the low pH viral inactivation step is loaded onto a cation exchange column.

12. The method of claim 11, wherein the cation exchange column is a POROS HS50 cation exchange column.

13. The method of claim 1, wherein the cation exchange step comprises using one or more buffers selected from the group consisting of:
   a. 50 mM sodium acetate at a pH of 5.0 for equilibration and Post-Load Wash 1;
   b. 50 mM sodium acetate and 60 mM sodium chloride at a pH of 4.9 for Post-Load Wash 2;
   c. 50 mM sodium acetate, 90 mM arginine hydrochloride, and 30 mM sodium chloride at a pH of 5.0 for elution;
   d. 2.0 M sodium chloride for stripping;
   e. 1.0 N sodium hydroxide for sanitization; and/or
   f. 0.1 N sodium hydroxide for storage.

14. The method of claim 1, wherein processing conditions for the cation exchange step include one or more of the following:
   a. a load capacity of 22-45 g/L in the Normal Operating Range and 15-50 g/L in the Proven Acceptable Range;
   b. a temperature of 15-25° C. in the Normal Operating Range 13-27° C. in the Proven Acceptable Range;
   c. an elution buffer pH of 4.90-5.10 in the Normal Operating Range and 4.90-5.10 in the Proven Acceptable Range;
   d. an elution buffer conductivity of 11.1-13.6 mS/cm in the Normal Operating Range and 11.1-13.6 mS/cm in the Proven Acceptable Range;
   e. an elution flow rate of 150-300 cm/hr in the Normal Operating Range and 120-330 cm/hr in the Proven Acceptable Range;
   f. an eluate hold time of ≤7 days in the Normal Operating Range and ≤10 days in the Proven Acceptable Range;
   g. column cycles of ≤100 in the Normal Operating Range and ≤100 in the Proven Acceptable Range;
   h. an eluate post-filtration bioburden of <3 CFU/10 mL;
   i. an eluate post-filtration endotoxin of <5 EU/mL;
   j. a step yield of ≥58%; and/or
   k. an elution volume of 2.3-5.0 column volumes.

15. The method of claim 13, wherein the pooled eluate from the cation exchange step is adjusted to a pH of 8.00 and a conductivity of 8.5 mS/cm with 100 mM Tris, 180 mM arginine at a pH of 9.0 and Water For Injection.

16. The method of claim 15, wherein the adjusted pooled eluate from the cation exchange step is loaded on an anion exchange column within 24 hours of the adjustment.

17. The method of claim 1, wherein the anion exchange step comprises one or more buffers selected from the group consisting of:
   a. 100 mM Tris and 180 mM arginine at a pH of 9.0 for load pH adjustment;
   b. Water For Injection for load conductivity adjustment and flush;
   c. 2 M sodium chloride for conditioning;
   d. 20 mM Tris and 65 mM sodium chloride at a pH of 7.6 for equilibration and post-load chase;
   e. 2 M sodium chloride for post-load elution stripping;
   f. 1.0 N sodium hydroxide for sanitization; and/or
   g. 0.1 N sodium hydroxide for storage.

18. The method of claim 1, wherein processing conditions for the anion exchange step include one or more of the following:
   a. a load pH of 7.90-8.10 in the Normal Operating Range and 7.80-8.20 in the Proven Acceptable Range;
   b. a load conductivity of 8.0-9.0 mS/cm in the Normal Operating Range and 7.0-10.0 mS/cm in the Proven Acceptable Range;
   c. a load capacity pH of 25-90 g/L in the Normal Operating Range and 25-100 g/L in the Proven Acceptable Range;
   d. a hold time of ≤1 day in the Normal Operating Range and ≤4 days in the Proven Acceptable Range;
   e. a product hold time of ≤4 days in the Normal Operating Range and ≤6 days in the Proven Acceptable Range;
   f. column cycles of ≤100 in the Normal Operating Range and ≤100 in the Proven Acceptable Range;
   g. a post-filtration eluate bioburden of <3 CFU/10 mL; and/or
   h. a post-filtration eluate endotoxin concentration of <5 EU/mL; and
   i. a product yield of ≥67%.

19. The method of claim 1, wherein flow-through filtrate from the anion exchange step is filtered to remove viruses or virus-like particles.

20. The method of claim 19, wherein the virus filtration step comprises a pre-flush with Water For Injection, and/or equilibration and a post-loading chase using 20 mM Tris (pH 7.6) and 65 mM sodium chloride.

21. The method of claim 1, wherein processing conditions for the virus filtration step include one or more of the following:
   a. a virus filter differential pressure during load and chase of 21-32 psid in the Normal Operating Range and 21-35 psid in the Proven Acceptable Range;
   b. a total pause time during load and chase of 0 minutes in the Normal Operating Range and ≤120 minutes in the Proven Acceptable Range;

c. a chase volume of ≤15 L/m² in the Normal Operating Range and ≤20 L/m² in the Proven Acceptable Range;
d. passing of a post-use integrity test;
e. a load concentration of 3.0-6.0 g/L in the Normal Operating Range and ≤6.7 g/L in the Proven Acceptable Range;
f. a virus filter load of ≤700 L/m² in the Normal Operating Range and ≤1200 L/m² in the Proven Acceptable Range;
g. a virus filter load of ≤700 L/m² in the Normal Operating Range and ≤700 L/m² in the Proven Acceptable Range;
h. a product hold time of ≤4 days in the Normal Operating Range and ≤6 days in the Proven Acceptable Range;
i. a pre-filtration bioburden of <3 CFU/10 mL;
j. an endotoxin concentration of <2 EU/mL;
k. passing of a pre-use integrity test; and/or
l. A processing time of ≤12 hours; and/or
m. a step yield of ≥90%.

22. The method of claim 1, wherein a pool from the virus filtration step is:
(a) concentrated and diafiltered; or
(b) ultrafiltrated and concentrated to 55 g/L using 30 kDa molecular weight cut-off ultrafiltration membranes; diafiltered with 6 diafiltration volumes into a formulation buffer comprising 10 mM sodium phosphate and 150 mM sodium chloride at a pH of 7.0; and measured and diluted to a product concentration of 10.0 g/L.

23. The method of claim 22, wherein the diluted product is 0.5/0.2 μm filtered and Polysorbate 80 is added to a diluted product pool to achieve a final concentration of 0.02% (w/v) Polysorbate 80.

24. The method of claim 1, wherein the ultrafiltration and diafiltration steps comprise the use of one or more buffers selected from the group consisting of:
a. Water For Injection as a flush;
b. 0.5 M sodium hydroxide for sanitization;
c. 10 mM sodium phosphate and 150 mM sodium chloride at a pH of 7.0 for equilibration, diafiltration, chase and pool dilution;
d. 0.1 M sodium hydroxide for storage; and/or
e. 10% (w/v) Polysorbate 80 for excipient.

25. The method of claim 1, wherein processing conditions for the ultrafiltration and diafiltration steps include one or more of the following:
a. a dilution of within 1% of calculated volume in the Normal Operating Range and within 3% of calculated volume in the Proven Acceptable Range;
b. 10% (w/v) Polysorbate 80 is 0.19-0.21% (w/v) of diluted ultrafiltration/diafiltration product in the Normal Operating Range and 0.17-0.23% (w/v) of diluted ultrafiltration/diafiltration product in the Proven Acceptable Range;
c. an un-formulated drug substance pH of 6.5-7.5;
d. a diluted ultrafiltration/diafiltration product concentration of 9.0-11.0 mg/ml;
e. passing of a pre-use integrity test;
f. a membrane loading of 100-500 g/m² in the Normal Operating Range and 50-600 g/m² in the Proven Acceptable Range;
g. a feed flux of 240-420 LMH in the Normal Operating Range and 180-440 LMH in the Proven Acceptable Range;
h. a transmembrane pressure of 10-30 psi in the Normal Operating Range and within 8-35 psi in the Proven Acceptable Range;
i. a pressure of 15-25° C. in the Normal Operating Range and 12-30° C. in the Proven Acceptable Range;
j. a fed batch ratio of 1-3 in the Normal Operating Range and 1-5 in the Proven Acceptable Range;
k. a concentration at end of ultrafilitration target of 13-17 g/L in the Normal Operating Range and 12-20 g/L in the Proven Acceptable Range;
l. A diavolume of 5.5-7.0 in the Normal Operating Range and 4.5-7.0 in the Proven Acceptable Range;
m. an unformulated ultrafiltration and diafiltration retentate hold of ≤4 days in the Normal Operating Range and ≤6 days in the Proven Acceptable Range;
n. a diluted ultrafiltrated/diafiltrated product hold of ≤7 days in the Normal Operating Range and ≤14 days in the Proven Acceptable Range;
o. a step yield of ≥90%;
p. a processing time from the start of initial concentration through end of diafiltration of ≤11.1 hours;
q. a post-use normalized water permeability (NWP) flux of 75-125% of initial;
r. a diluted ultrafiltrated/diafiltrated pre-filtration pool bioburden of <10 CFU/10 mL; and
S. a diluted ultrafiltrated/diafiltrated post-filtration pool bioburden of <3 CFU/10 mL; and/or a diluted ultrafiltrated/diafiltrated post-filtration pool endotoxin concentration of <2 EU/mL.

26. The method of claim 1, wherein processing conditions for the ultrafiltration and diafiltration steps include one or more of the following:
a. an initial concentration target of 40-60 g/L;
b. a final concentration target of 140-160 g/L, including a 1.07 recovery factor);
c. a diavolume of 4.5-7.5, with a target of 6.0;
d. an undiluted ultrafiltrated/diafiltrated product hold of ≤24 hours;
e. a diluted ultrafiltrated/diafiltrated product hold of ≤24 hours;
f. use of a Millipore Pellicon 3 Ultracel C screen 30 kDa MWCO filter;
g. a flush WFI≥20 L/m²;
h. an equilibrium of 50 mM NaPO$_4$ pH 7.4, 25 mM L-Arg;
i. a membrane load of ≤600 L/m²;
j. a target feed flow rate for all product steps of 360 LMH;
k. a target transmembrane pressure for all product steps of 15 psi;
l. A feed pressure of ≤50 psi;
m. a diafiltration buffer that is the same as equilibrium;
n. a final concentration that can be controlled by feed pressure;
o. a temperature of 15-35° C.;
p. a recovery with ≤1×system hold-up volume;
q. a dilution to target 120 g/L with DF/equilibrium buffer;
r. 0.1919-0.2393 kg/kg addition of excipient addition buffer, 25 mM L-Arg, 30% Sucrose 0.30% (w/v), PS 80) to 120 g/L UF/DF product for final formulation;
s. membrane re-use up to 20 cycles;
t. sanitization with 0.5 M NaOH;
u. storage with 0.1 M NaOH;
v. a yield of >60%;
w. express SHC filterability 120 g/L UF/DF product: ≤40 L/m²; and
x. express SHC filterability BDS of ≤3045 L/m².

27. The method of claim 1, wherein the mammalian cells are Chinese Hamster Ovary (CHO) cells.

* * * * *